US012611470B2

(12) United States Patent　　　　(10) Patent No.:　US 12,611,470 B2
Smolke et al.　　　　　　　　　　　(45) Date of Patent:　Apr. 28, 2026

(54) CHROMATIN-OPENING ELEMENT FOR STABLE LONG TERM GENE EXPRESSION

(71) Applicants:CZ Biohub SF, LLC, San Francisco, CA (US); The Board of Trustees of the Leland Stanford Junior University, Stanford, CA (US)

(72) Inventors: Christina Smolke, Stanford, CA (US); Shireen S. Rudina, Stanford, CA (US)

(73) Assignees: CZ Biohub SF, LLC, San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 1073 days.

(21) Appl. No.: 17/606,408

(22) PCT Filed: Apr. 27, 2020

(86) PCT No.: PCT/US2020/030093
　§ 371 (c)(1),
　(2) Date: Oct. 25, 2021

(87) PCT Pub. No.: WO2020/223160
　PCT Pub. Date: Nov. 5, 2020

(65) Prior Publication Data
US 2022/0193266 A1　Jun. 23, 2022

Related U.S. Application Data

(60) Provisional application No. 62/841,151, filed on Apr. 30, 2019.

(51) Int. Cl.
　A61K 48/00　　(2006.01)
　C12N 15/85　　(2006.01)

(52) U.S. Cl.
　CPC .......... A61K 48/0066 (2013.01); C12N 15/85 (2013.01); C12N 2830/46 (2013.01)

(58) Field of Classification Search
　CPC . A61K 48/0066; C12N 15/85; C12N 2830/46
　See application file for complete search history.

(56) References Cited

U.S. PATENT DOCUMENTS

| | | | |
|---|---|---|---|
| 6,949,361 | B2 | 9/2005 | Antoniou et al. |
| 7,442,787 | B2 | 10/2008 | Antoniou et al. |
| 7,632,661 | B2 | 12/2009 | Simpson et al. |
| 2009/0018031 | A1 | 1/2009 | Trinklein et al. |
| 2009/0111144 | A1 | 4/2009 | Bebbington |
| 2014/0186890 | A1* | 7/2014 | Otte ........................ C07K 16/30 |
| | | | 435/69.6 |

FOREIGN PATENT DOCUMENTS

| | | |
|---|---|---|
| EP | 2348118 A1 | 7/2011 |
| WO | 2000005393 A2 | 2/2000 |

| | | |
|---|---|---|
| WO | 2002024930 A2 | 3/2002 |
| WO | 2006123097 A1 | 11/2006 |
| WO | 2018204764 A1 | 11/2018 |

OTHER PUBLICATIONS

Huxley et al. "The mouse surfeit locus contains a cluster of six genes associated with four Gp G-rich islands in 32 kilobases of genomic DNA," Mol. Cell Biol., 1990, 10(2), 605-614 (Year: 1990).*
NCBI Blastn sequence alignment, NCBI Blast: Nucleotide Sequence, accessed Apr. 12, 2025, instant SEQ ID No. 1 aligned with SEQ ID No. 12129 of Trinklein et al. (US 2009/0018031 A1) (Year: 2025).*
NCBI Blastn sequence alignment, NCBI Blast: Nucleotide Sequence, accessed Apr. 12, 2025, instant SEQ ID No. 5 aligned with SEQ ID No. 12129 of Trinklein et al. (US 2009/0018031 A1) (Year: 2025).*
PCT/US2020/030093 , "International Search Report and Written Opinion", Aug. 17, 2020, 10 pages.
ENCODE Project Consortium, An Integrated Encyclopedia of DNA Elements in the Human Genome, Nature, vol. 489, No. 7414, Sep. 9, 2012.
Adamson et al., A Multiplexed Single-cell CRISPR Screening Platform Enables Systematic Dissection of the Unfolded Protein Response, Cell, vol. 167, No. 7, Dec. 15, 2016, pp. 1867-1882.
Alhaji et al., Silencing of Transgene Expression in Mammalian Cells by DNA Methylation and Histone Modifications in Gene Therapy Perspective, Biotechnology and Genetic Engineering Reviews, vol. 35, No. 1, Apr. 2019, pp. 1-25.
Allen et al., Correlation of DNA Methylation with Histone Modifications Across the HNRPA2B1-CBX3 Ubiquitously-Acting Chromatin Open Element (UCOE), Epigenetics, vol. 2, No. 4, Oct.-Dec. 2007, pp. 227-236.
Altschul et al., Basic Local Alignment Search Tool, Journal of Molecular Biology, vol. 215, No. 3, Oct. 5, 1990, pp. 403-410.

(Continued)

*Primary Examiner* — Emily A Cordas
(74) *Attorney, Agent, or Firm* — Kilpatrick Townsend & Stockton LLP

(57)　　　　ABSTRACT

A novel ubiquitous chromatin opening element (UCOE) named SRF-UCOE and methods for its use are provided. Compositions including recombinant and synthetic SRF-UCOE nucleic acid molecules, DNA constructs and vectors comprising the SRF-UCOE nucleic acid molecules, host cells comprising the DNA constructs or vectors, and cell culture systems comprising such host cells. SRF-UCOE polynucleotide sequences can be used in DNA constructs or expression cassettes for transformation and expression in cells or organisms of interest. The compositions and methods provided are useful for increasing and/or maintaining expression of a gene of interest. Transgenic cells, tissues, and animals comprising a SRF-UCOE nucleotide sequence are also provided. Methods are provided for increasing and/or maintaining expression of a gene of interest and for treating a subject via gene therapy.

19 Claims, 15 Drawing Sheets

Specification includes a Sequence Listing.

(56) References Cited

OTHER PUBLICATIONS

Altschul et al., Gapped BLAST and PSI-BLAST: A New Generation of Protein Database Search Programs, Nucleic Acids Research, vol. 25, No. 17, Sep. 1, 1997, pp. 3389-3402.

Anderson, Human Gene Therapy, Nature, vol. 392, Apr. 30, 1998, pp. 25-30.

Antoniou et al., Transgenes Encompassing Dual-Promoter CpG Islands from the Human TBP and HNRPA2B1 Loci are Resistant to Heterochromatin-Mediated Silencing, Genomics, vol. 82, No. 3, Sep. 2003, pp. 269-279.

Bannister et al., Regulation of Chromatin by Histone Modifications, Cell Research, vol. 21, No. 3, Mar. 2011, pp. 381-395.

Benton et al., The Use of UCOE Vectors in Combination with a Preadapted Serum Free, Suspension Cell Line Allows for Rapid Production of Large Quantities of Protein, Cytotechnology, vol. 38, Jan. 2002, pp. 43-46.

Brendel et al., Physiological Regulation of Transgene Expression by a Lentiviral Vector Containing the A2UCOE Linked to a Myeloid Promoter, Gene Therapy, vol. 19, No. 10, Oct. 2012, pp. 1018-1029.

Chen et al., Genome-Wide CRISPR Screen in a Mouse Model of Tumor Growth and Metastasis, Cell, vol. 160, No. 6, Mar. 12, 2015, pp. 1246-1260.

Chen et al., Reactivation of Silenced, Virally Transduced Genes by Inhibitors of Histone Deacetylase, Proceedings of the National Academy of Sciences, vol. 94, No. 11, May 27, 1997, pp. 5798-5803.

Chowdhury et al., Long-term Improvement of Hypercholesterolemia After Ex Vivo Gene Therapy in LDLR-deficient Rabbits, Science, vol. 254, No. 5039, Dec. 20, 1991, pp. 1802-1805.

Crane-Robinson et al., Chromosomal Mapping of Core Histone Acetylation by Immunoselection, Methods, vol. 12, No. 1, May 1, 1997, pp. 48-56.

Dighe et al., Long-term Reproducible Expression in Human Fetal Liver Hematopoietic Stem Cells with a UCOE-based Lentiviral Vector, Public Library of Science One, vol. 9, No. 8, Aug. 12, 2014, pp. 1-8.

Duhig et al., The Human Surfeit Locus, Genomics, vol. 52, No. 1, Aug. 1998, pp. 72-78.

Ehrhardt et al., Episomal Vectors for Gene Therapy, Current Gene Therapy, vol. 8, No. 3, Jun. 2008, pp. 147-161.

Ellis et al., Silencing and Variegation of Gammaretrovirus and Lentivirus Vectors, Human Gene Therapy, vol. 16, No. 11, Nov. 1, 2005, pp. 1241-1246.

Emerson, Ex Vivo Expansion of Hematopoietic Precursors, Progenitors, and Stem Cells: The Next Generation of Cellular Therapeutics, Blood, vol. 87, No. 8, Apr. 15, 1996, pp. 3082-3088.

Ernst et al., Mapping and Analysis of Chromatin State Dynamics in Nine Human Cell Types, Nature, vol. 473, No. 7345, Mar. 2011, 7 pages.

Flotte et al., Stable in Vivo Expression of the Cystic Fibrosis Transmembrane Conductance Regulator with an Adeno-Associated Virus Vector, Proceedings of the National Academy of Sciences, vol. 90, No. 22, Nov. 15, 1993, pp. 10613-10617.

Gill et al., Increased Persistence of Lung Gene Expression Using Plasmids Containing the Ubiquitin C or Elongation Factor1α Promoter, Gene Therapy, vol. 8, No. 20, Nov. 2001, pp. 1539-1546.

Guttman et al., Ab Initio Reconstruction of Cell Type-specific Transcriptomes in Mouse Reveals the Conserved Multi-Exonic Structure of lincRNAs, Nature Biotechnology, vol. 28, No. 5, May 2, 2010, pp. 503-510.

Haenseler et al., Lentiviral Gene Therapy Vector with UCOE Stably Restores Function in iPSC-Derived Neutrophils of a CDG Patient, Matters, vol. 2018, May 2018, pp. 1-11.

Hitt et al., Human Adenovirus Vectors for Gene Transfer Into Mammalian Cells, Advances in Pharmacology, vol. 40, 1997, pp. 137-206.

Hsu et al., The UCSC Known Genes, Bioinformatics, vol. 22, No. 9, May 2006, pp. 1036-1046.

Jost et al., Combined CRISPRi/a-Based Chemical Genetic Screens Reveal that Rigosertib Is a Microtubule-Destabilizing Agent, Molecular Cell, vol. 68, No. 1, Oct. 5, 2017, pp. 210-223.

Jostock et al., Mammalian Stable Expression of Biotherapeutics, Chapter 15, Therapeutic Proteins: Methods and Protocols, vol. 899, Jan. 2012, pp. 227-238.

Karlin et al., Applications and Statistics for Multiple High-Scoring Segments in Molecular Sequences, Proceedings of the National Academy of Sciences, vol. 90, No. 12, Jun. 15, 1993, pp. 5873-5877.

Karlin et al., Methods for Assessing the Statistical Significance of Molecular Sequence Features by Using General Scoring Schemes, Proceedings of the National Academy of Sciences, vol. 87, No. 6, Mar. 1990, pp. 2264-2268.

Kazuki et al., Human Artificial Chromosomes for Gene Delivery and the Development of Animal Models, Molecular Therapy, vol. 19, No. 9, Sep. 1, 2011, pp. 1591-1601.

Kent et al., The Human Genome Browser at UCSC, Genome Research, vol. 12, No. 6, Jun. 1, 2002, pp. 996-1006.

Khan et al., JASPAR 2018: Update of the Open-access Database of Transcription Factor Binding Profiles and Its Web Framework, Nucleic Acids Research, vol. 46, No. D1, Jan. 4, 2018, pp. D260-D266.

Knight et al., Safer, Silencing-resistant Lentiviral Vectors: Optimization of the Ubiquitous Chromatin-opening Element Through Elimination of Aberrant Splicing, Journal of Virology, vol. 86, No. 17, Sep. 1, 2012, pp. 9088-9095.

Kunkiel et al., The CpG-Sites of the CBX3 Ubiquitous Chromatin Opening Element Are Critical Structural Determinants for the Anti-Silencing Function, Scientific Reports, vol. 7, No. 1, Aug. 2017, pp. 1-13.

Kuriyama et al., Expression of a Retrovirally Transduced Gene Under Control of an Internal Housekeeping Gene Promoter Does Not Persist Due to Methylation and is Restored Partially by 5-Azacytidine Treatment, Gene Therapy, vol. 5, No. 10, Oct. 1998, pp. 1299-1305.

Liu et al., Delivery Strategies of the CRISPR-Cas9 Gene-Editing System for Therapeutic Applications, Journal of Controlled Release, vol. 266, Nov. 28, 2017, pp. 17-26.

Miller et al., Recombinant Adeno-Associated Virus (rAAV)-Mediated Expression of a Human Gamma-Globin Gene in Human Progenitor-Derived Erythroid Cells, Proceedings of the National Academy of Sciences, vol. 91, No. 21, Oct. 1, 1994, pp. 10183-10187.

Milone et al., Clinical Use of Lentiviral Vectors, Leukemia, vol. 32, No. 7, Jul. 2018, pp. 1529-1541.

Muller-Kuller et al., A Minimal Ubiquitous Chromatin Opening Element (UCOE) Effectively Prevents Silencing of Juxtaposed Heterologous Promoters by Epigenetic Remodeling in Multipotent and Pluripotent Stem Cells, Nucleic Acids Research, vol. 43, No. 3, Feb. 2015, pp. 1577-1592.

Naso et al., Adeno-Associated Virus (AAV) as a Vector for Gene Therapy, BioDrugs, vol. 31, No. 4, Jul. 1, 2017, pp. 317-334.

Needleman et al., A General Method Applicable to the Search for Similarities in the Amino Acid Sequence of Two Proteins, Journal of Molecular Biology, vol. 48, No. 3, Mar. 1970, pp. 443-453.

Pearson et al., Improved Tools for Biological Sequence Comparison, Proceedings of the National Academy of Sciences of the United States of America, vol. 85, No. 8, Apr. 1988, pp. 2444-2448.

Perez et al., CRISPR-Cas Systems: Ushering in the New Genome Editing Era, Bioengineered, vol. 9, No. 1, Jul. 2018, pp. 214-221.

Philip et al., Efficient and Sustained Gene Expression in Primary T Lymphocytes and Primary and Cultured Tumor Cells Mediated by Adeno-associated Virus Plasmid DNA Complexed to Cationic Liposomes, Molecular and Cellular Biology, vol. 14, No. 4, Apr. 1, 1994, pp. 2411-2418.

Pikaart et al., Loss of Transcriptional Activity of a Transgene is Accompanied by DNA Methylation and Histone Deacetylation and is Prevented by Insulators, Genes & Development, vol. 12, No. 18, Aug. 5, 1998, pp. 2852-2862.

Rein et al., Identifying 5-methylcytosine and Related Modifications in DNA Genomes, Nucleic Acids Research, vol. 26, No. 10, May 15, 1998, pp. 2255-2264.

(56)                References Cited

OTHER PUBLICATIONS

Rice et al., EMBOSS: The European Molecular Biology Open Software Suite, Trends in Genetics, vol. 16, No. 6, Jun. 2000, pp. 276-277.

Russell et al., Adeno-associated Virus Vectors Preferentially Transduce Cells in S Phase, Proceedings of the National Academy of Sciences, vol. 91, No. 19, Sep. 13, 1994, pp. 8915-8919.

Saunders et al., Chromatin Function Modifying Elements in an Industrial Antibody Production Platform-Comparison of UCOE, MAR, STAR and cHS4 Elements, Public Library of Science One, vol. 10, No. 4, Apr. 7, 2015, pp. 1-20.

She et al., Definition, Conservation and Epigenetics of Housekeeping and Tissue-Enriched Genes, Brihanmumbai Municipal Corporation Genomics, vol. 10, Jun. 17, 2009, pp. 1-12.

Silva et al., Meganucleases and Other Tools for Targeted Genome Engineering: Perspectives and Challenges for Gene Therapy, Current Gene Therapy, vol. 11, No. 1, Feb. 1, 2011, pp. 11-27.

Smith et al., Comparison of Biosequences, Advances in Applied Mathematics, vol. 2, No. 4, Dec. 1, 1981, pp. 482-489.

Uchiyama et al., Foamy Virus Vector-Mediated Gene Correction of a Mouse Model of Wiskott-Aldrich Syndrome, Molecular Therapy, vol. 20, No. 6, Jun. 1, 2012, pp. 1270-1279.

Walsh et al., Regulated High Level Expression of a Human Gamma-globin Gene Introduced into Erythroid Cells by an Adeno-associated Virus Vector, Proceedings of the National Academy of Sciences of the United States of America, vol. 89, Aug. 1992, pp. 7257-7261.

Wang et al., Factorbook.Org: A Wiki-based Database for Transcription Factor-binding Data Generated by the ENCODE Consortium, Nucleic Acids Research, vol. 41, No. D1, Jan. 2013, pp. D171-D176.

Weth et al., CTCF Induces Histone Variant Incorporation, Erases the H3K27me3 Histone Mark and Opens Chromatin, Nucleic Acids Research, vol. 42, No. 19, Oct. 2014, pp. 11941-11951.

Williams et al., CpG-Island Fragments from the HNRPA2B1/CBX3 Genomic Locus Reduce Silencing and Enhance Transgene Expression from the hCMV Promoter/Enhancer in Mammalian Cells, Brihanmumbai Municipal Corporation Biotechnology, vol. 5, Jun. 3, 2005, pp. 1-9.

Wilson et al., Ex Vivo Gene Therapy of Familial Hypercholesterolemia, Human Gene Therapy, vol. 3, No. 2, Apr. 1, 1992, pp. 179-222.

Wu, Analysis of Hypersensitive Sites in Chromatin, Methods in Enzymology, vol. 170, Jan. 1, 1989, pp. 269-289.

Xiang et al., Massively Parallel RNA Device Engineering in Mammalian Cells With RNA-seq, Nature Communications, vol. 10, No. 1, Sep. 23, 2019, pp. 1-16.

Yang et al., DNA Methylation Contributes to Loss in Productivity of Monoclonal Antibody-producing CHO Cell Lines, Journal of Biotechnology, vol. 147, Nos. 3-4, Jun. 1, 2010, pp. 180-185.

Zhang et al., A Ubiquitous Chromatin Opening Element (UCOE) Confers Resistance to DNA Methylation-Mediated Silencing of Lentiviral Vectors, Molecular Therapy, vol. 18, No. 9, Sep. 2010, pp. 1640-1649.

Zufferey et al., Production of High-Titer Lentiviral Vectors, Current Protocols in Human Genetics, vol. 26, No. 1, Aug. 2000.

* cited by examiner

FIG. 1A

| Candidate Rank | Chrom osome | Starting Position | Ending Position | HKG Accession Number | Distance | CV of HKG |
|---|---|---|---|---|---|---|
| (A2UCOE) | chr7 | 26239064 | 26242980 | NM_002137 | 0 | 0.203 |
| 1 | chr6 | 160210822 | 160212252 | NM_014161 | 0 | 0.231 |
| 2 | chr1 | 245027688 | 245027958 | NM_031844 | 0 | 0.265 |
| 3 | chr6 | 160147650 | 160148658 | NM_004906 | 0 | 0.322 |
| 4 | chr16 | 25122572 | 25123049 | NM_001032391 | 0 | 0.36 |
| 5 | chr20 | 5093492 | 5094272 | NM_001009924 | 0 | 0.367 |
| 6 | chr9 | 136223261 | 136223954 | NM_017503 | 0 | 0.409 |
| 7 | chr1 | 226595430 | 226596263 | NM_001618 | 0 | 0.426 |
| 8 | chr17 | 66507666 | 66508098 | NM_212471 | 0 | 0.442 |
| 9 | chr15 | 44828479 | 44829488 | NM_003758 | 0 | 0.472 |
| 10 | chr10 | 105156061 | 105156603 | NM_032747 | 0 | 0.518 |
| 11 | chr4 | 71705461 | 71705654 | NM_002092 | 0 | 0.593 |
| 12 | chr8 | 30670056 | 30670546 | NM_001009352 | 0 | 0.634 |
| 13 | chr4 | 37891884 | 37893238 | NM_015173 | 0 | 0.773 |
| 14 | chr1 | 45476510 | 45477327 | NM_024602 | 0 | 0.845 |
| 15 | chr10 | 105156297 | 105156587 | NM_032747 | 27 | 0.518 |
| 16 | chr4 | 37892104 | 37892292 | NM_015173 | 412 | 0.773 |
| 17 | chr20 | 49548302 | 49548597 | NM_181442 | 775 | 0.317 |
| 18 | chr6 | 24720926 | 24722570 | NM_030939 | 1523 | 0.359 |
| 19 | chr13 | 76123027 | 76123946 | NM_203495 | 11019 | 0.604 |
| 20 | chr8 | 30514493 | 30515911 | NM_000637 | 19668 | 0.355 |

```
Truncation 6-3 (SEQ ID NO:4)   GCACGACGACCACAATTCCACTGAAAGCATTTAATACGGAACTTGTCACTCCCAGGGAGC   60
SRF-UCOE       (SEQ ID NO:1)   GCACGACGACCACAATTCCACTGAAAGCATTTAATACGGAACTTGTCACTCCCAGGGAGC   60
Truncation 6-1 (SEQ ID NO:2)   ------------------------------------------------------------    0
Truncation 6-2 (SEQ ID NO:3)   ------------------------------------------------------------    0
Core Sequence  (SEQ ID NO:5)   ------------------------------------------------------------    0

Truncation 6-3 (SEQ ID NO:4)   CTCCGCTCAGCCGGCAGTTGGTTCATTTCAATCCCACGACAACCCTTCAAAGTGCAGGG   120
SRF-UCOE       (SEQ ID NO:1)   CTCCGCTCAGCCGGCAGTTGGTTCATTTCAATCCCACGACAACCCTTCAAAGTGCAGGG   120
Truncation 6-1 (SEQ ID NO:2)   ---------------------------------------------TTCAAAGTGCAGGG    14
Truncation 6-2 (SEQ ID NO:3)   ------------------------------------------------------------    0
Core Sequence  (SEQ ID NO:5)   ------------------------------------------------------------    0

Truncation 6-3 (SEQ ID NO:4)   CAGACAGCAGGTGGCTCTGCCCAGGCGCCTGGATCACAGCCCGGCCTGCAGCCCTCACCT   180
SRF-UCOE       (SEQ ID NO:1)   CAGACAGCAGGTGGCTCTGCCCAGGCGCCTGGATCACAGCCCGGCCTGCAGCCCTCACCT   180
Truncation 6-1 (SEQ ID NO:2)   CAGACAGCAGGTGGCTCTGCCCAGGCGCCTGGATCACAGCCCGGCCTGCAGCCCTCACCT    74
Truncation 6-2 (SEQ ID NO:3)   ------------------------------------------------------------    0
Core Sequence  (SEQ ID NO:5)   ------------------------------------------------------------    0

Truncation 6-3 (SEQ ID NO:4)   GGGCGCGGGGAGACCCTGAGGACGCTCCTCCAGGCGGCGCTGGCCGGGGCCTGCGGACAC   240
SRF-UCOE       (SEQ ID NO:1)   GGGCGCGGGGAGACCCTGAGGACGCTCCTCCAGGCGGCGCTGGCCGGGGCCTGCGGACAC   240
Truncation 6-1 (SEQ ID NO:2)   GGGCGCGGGGAGACCCTGAGGACGCTCCTCCAGGCGGCGCTGGCCGGGGCCTGCGGACAC   134
Truncation 6-2 (SEQ ID NO:3)   ------------------------------------------------------------    0
Core Sequence  (SEQ ID NO:5)   ------------------------------------------------------------    0

Truncation 6-3 (SEQ ID NO:4)   GGACGGGGCGGGCTGAGCTCCGGGACCCCTCCCCGCGCCCCCGCACCCCGCACCC   300
SRF-UCOE       (SEQ ID NO:1)   GGACGGGGCGGGCTGAGCTCCGGGACCCCTCCCCGCGCCCCCGCACCCCGCACCC   300
Truncation 6-1 (SEQ ID NO:2)   GGACGGGGCGGGCTGAGCTCCGGGACCCCTCCCCGCGCCCCCGCACCCCGCACCC   194
Truncation 6-2 (SEQ ID NO:3)   ------------------------------------------------------     0
Core Sequence  (SEQ ID NO:5)   ------------------------------------------------------     0
```

FIG. 7 (cont.)

```
Truncation 6-3 (SEQ ID NO:4)  CGACCCCGCACCGGCGCTCACCCGTCCCAGCCCCGCGCCCGCCCAGCCCCAGCTGCAAC  360
SRF-UCOE       (SEQ ID NO:1)  CGCACCCCGCACCGGCGCTCACCCGTCCCAGCCCCGCGCCCGCCCAGCCCCAGCTGCAAC 360
Truncation 6-1 (SEQ ID NO:2)  CGCACCCCGCACCGGCGCTCACCCGTCCCAGCCCCGCGCCCGCCCAGCCCCAGCTGCAAC 254
Truncation 6-2 (SEQ ID NO:3)  ------------------------------------------------------------   0
Core Sequence  (SEQ ID NO:5)  ------------------------------------------------------------   0

Truncation 6-3 (SEQ ID NO:4)  GCAGCCACCGCGCCATCGCCACCGGCCCGCGGGCGCTTCCGGGACGCAGGAGGCATCT   420
SRF-UCOE       (SEQ ID NO:1)  GCAGCCACCGCGCCATCGCCACCGGCCCGCGGGCGCTTCCGGGACGCAGGAGGCATCT   420
Truncation 6-1 (SEQ ID NO:2)  GCAGCCACCGCGCCATCGCCACCGGCCCGCGGGCGCTTCCGGGACGCAGGAGGCATCT   314
Truncation 6-2 (SEQ ID NO:3)  ----------------------------------------------------------     0
Core Sequence  (SEQ ID NO:5)  ----------------------------------------------------------     0

Truncation 6-3 (SEQ ID NO:4)  GCATCCGGGGCGCCGCTGAGTCCCGCCCCAGAGCCCCGGCTCCAGGTTCTGCGAG      480
SRF-UCOE       (SEQ ID NO:1)  GCATCCGGGGCGCCGCTGAGTCCCGCCCCAGAGCCCCGGCTCCAGGTTCTGCGAG      480
Truncation 6-1 (SEQ ID NO:2)  GCATCCGGGGCGCCGCTGAGTCCCGCCCCAGAGCCCCGGCTCCAGGTTCTGCGAG      374
Truncation 6-2 (SEQ ID NO:3)  ------------------------------------------------------AG      2
Core Sequence  (SEQ ID NO:5)  ------------------------------------------------------AG      2
                                                                                    **

Truncation 6-3 (SEQ ID NO:4)  CGGCTTCCGCCGGGCTGCTCCGCGGGCGCGTCGGCCATGAGCGAGTTGCCGGGCGACGTG  540
SRF-UCOE       (SEQ ID NO:1)  CGGCTTCCGCCGGGCTGCTCCGCGGGCGCGTCGGCCATGAGCGAGTTGCCGGGCGACGTG  540
Truncation 6-1 (SEQ ID NO:2)  CGGCTTCCGCCGGGCTGCTCCGCGGGCGCGTCGGCCATGAGCGAGTTGCCGGGCGACGTG  434
Truncation 6-2 (SEQ ID NO:3)  CGGCTTCCGCCGGGCTGCTCCGCGGGCGCGTCGGCCATGAGCGAGTTGCCGGGCGACGTG   62
Core Sequence  (SEQ ID NO:5)  ***********************************************************    62

Truncation 6-3 (SEQ ID NO:4)  CGGGGCGTTTCTGCGGGAGCACCCGAGCCTGCGGGCTCCAGACGACCCGCAAGGTTCGC   600
SRF-UCOE       (SEQ ID NO:1)  CGGGGCGTTTCTGCGGGAGCACCCGAGCCTGCGGGCTCCAGACGACCCGCAAGGTTCGC   600
Truncation 6-1 (SEQ ID NO:2)  CGGGGCGTTTCTGCGGGAGCACCCGAGCCTGCGGGCTCCAGACGACCCGCAAGGTTCGC   494
Truncation 6-2 (SEQ ID NO:3)  CGGGGCGTTTCTGCGGGAGCACCCGAGCCTGCGGGCTCCAGACGACCCGCAAGGTTCGC   122
Core Sequence  (SEQ ID NO:5)  **********************************************************     122
```

FIG. 7 (cont.)

```
Truncation 6-3 (SEQ ID NO:4)  AGCGCGGGAGGGGAACGGAGTGGCGGAGAAGGGCGCGGAGAAGGGCGCAGTTGGGATGAGGGGCTGAGGGGA  660
SRF-UCOE       (SEQ ID NO:1)  AGCGCGGGAGGGGAACGGAGTGGCGGAGAAGGGCGCAGTTGGGATGAGGGGCTGAGGGGA               660
Truncation 6-1 (SEQ ID NO:2)  AGCGCGGGAGGGGAACGGAGTGGCGGAGAAGGGCGCAGTTGGGATGAGGGGCTGAGGGGA               554
Truncation 6-2 (SEQ ID NO:3)  AGCGCGGGAGGGGAACGGAGTGGCGGAGAAGGGCGCAGTTGGGATGAGGGGCTGAGGGGA               182
Core Sequence  (SEQ ID NO:5)  AGCGCGGGAGGGGAACGGAGTGGCGGAGAAGGGCGCAGTTGGGATGAGGGGCTGAGGGGA               182
                              ************************************                ***********************

Truncation 6-3 (SEQ ID NO:4)  GGGCAGGGGAGAGAGGGCAGGGGAGAGAGAGGGGAGAGAGCAGGAGGAGAGGGGAAG                  720
SRF-UCOE       (SEQ ID NO:1)  GGGCAGGGGAGAGAGGGCAGGGGAGAGAGAGGGGAGAGAGCAGGAGGAGAGGGGAAG                  720
Truncation 6-1 (SEQ ID NO:2)  GGGCAGGGGAGAGAGGGCAGGGGAGAGAGAGGGGAGAGAGCAGGAGGAGAGGGGAAG                  614
Truncation 6-2 (SEQ ID NO:3)  GGGCAGGGGAGAGAGGGCAGGGGAGAGAGAGGGGAGAGAGCAGGAGGAGAGGGGAAG                  242
Core Sequence  (SEQ ID NO:5)  GGGCAGGGGAGAGAGGGCAGGGGAGAGAGAGGGGAGAGAGCAGGAGGAGAGGGGAAG                  242
                              *********************************************************

Truncation 6-3 (SEQ ID NO:4)  GCAGGGGAGAGAGGGCGCGGGGATCAGGGGAGGAGAGGGAA----------------                    761
SRF-UCOE       (SEQ ID NO:1)  GCAGGGGAGAGAGGGCGCGGGGATCAGGGGAGGAGAGGGAAGAGGGGCGCGGCAGGAGGGG              780
Truncation 6-1 (SEQ ID NO:2)  GCAGGGGAGAGAGGGCGCGGGGATCAGGGGAGGAGAGGGAAGAGGGGCGCGGCAGGAGGGG              674
Truncation 6-2 (SEQ ID NO:3)  GCAGGGGAGAGAGGGCGCGGGGATCAGGGGAGGAGAGGGAAGAGGGGCGCGGCAGGAGGGG              302
Core Sequence  (SEQ ID NO:5)  GCAGGGGAGAGAGGGCGCGGGGATCAGGGGAGGAGAGGGAA                                  283
                              *****************************************

Truncation 6-3 (SEQ ID NO:4)  ------------------------------------------------------------                761
SRF-UCOE       (SEQ ID NO:1)  GCACCAGGGAGCGGAGCCCTGGCCCTCCTGACGTCTGCCCGCCACGCGTCCGCAGGTG                  840
Truncation 6-1 (SEQ ID NO:2)  GCACCAGGGAGCGGAGCCCTGGCCCTCCTGACGTCTGCCCGCCACGCGTCCGCAGGTG                  734
Truncation 6-2 (SEQ ID NO:3)  GCACCAGGGAGCGGAGCCCTGGCCCTCCTGACGTCTGCCCGCCACGCGTCCGCAGGTG                  362
Core Sequence  (SEQ ID NO:5)  ------------------------------------------------------------                283

Truncation 6-3 (SEQ ID NO:4)  ------------------------------------------------------------                761
SRF-UCOE       (SEQ ID NO:1)  AGGTGCATCCTGACAGGTCACGAGCTGCCCTGCCGCCTGCCTGCCGGAGCTCCAGGTCTACACC            900
Truncation 6-1 (SEQ ID NO:2)  AGGTGCATCCTGACAGGTCACGAGCTGCCCTGCCGCCTGCCTGCCGGAGCTCCAGGTCTACACC            794
Truncation 6-2 (SEQ ID NO:3)  AGGTGCATCCTGACAGGTCACGAGCTGCCCTGCCGCCTGCCTGCCGGAGCTCCAGGTCTACACC            422
Core Sequence  (SEQ ID NO:5)  ------------------------------------------------------------                283
```

FIG. 7 (cont.)

```
Truncation 6-3 (SEQ ID NO:4)  ------------------------------------------------------------  761
SRF-UCOE       (SEQ ID NO:1)  CGCGGGCAAAAAGTACCAGCGGGCTGGTCCGCGCTCCCCGGCCTTCGACTATGCAGAGTTC  960
Truncation 6-1 (SEQ ID NO:2)  CGCGGGCAAAAAGTACCAGCGGGCTGGTCCGCGCTCCCCGGCCTTCGACTATGCAGAGTTC  854
Truncation 6-2 (SEQ ID NO:3)  CGCGGGCAAAAAGTACCAGCGGGCTGGTCCGCGCTCCCCGGCCTTCGACTATGCAGAGTTC  482
Core Sequence  (SEQ ID NO:5)  ------------------------------------------------------------  283

Truncation 6-3 (SEQ ID NO:4)  ------------------------------------------------------  761
SRF-UCOE       (SEQ ID NO:1)  GAGCCGCACATCGTGCCCAGCACCACCAAGAACCCGTAGGTGGTC  1002
Truncation 6-1 (SEQ ID NO:2)  GAGCCGCACATCGTGCCCAGCACCACCAAGAACCCGTAGGTGGTC  896
Truncation 6-2 (SEQ ID NO:3)  GAGCCGCACATCGTGCCCAGCACCACCAAGAACCCGTAGGTGGTC  524
Core Sequence  (SEQ ID NO:5)  ------------------------------------------------------  283
```

CHROMATIN-OPENING ELEMENT FOR STABLE LONG TERM GENE EXPRESSION

CROSS-REFERENCE TO RELATED APPLICATIONS

This application is a U.S. national phase application of PCT Application No. PCT/US2020/030093, filed Apr. 27, 2020, which claims the benefit of priority of U.S. Provisional Application No. 62/841,151, filed Apr. 30, 2019. This provisional application is incorporated by reference herein in its entirety for all purposes.

SEQUENCE LISTING

The official copy of the sequence listing is submitted electronically via EFS-Web as an ASCII formatted sequence listing with a file named 103182-1180463-002610WO-_SL.txt, created on Mar. 25, 2020 and having a size of 15,649 bytes, and is filed concurrently with the specification. The sequence listing contained in this ASCII formatted document is part of the specification and is herein incorporated by reference in its entirety.

BACKGROUND

Long-term stable expression of genes delivered to cells (transgenes) in mammalian cells is important in gene therapy, recombinant protein production, genetic reprogramming, and mammalian synthetic biology. However, transgenes are susceptible to time-dependent epigenetic silencing, as well as position effect variegation, making reproducible stable expression challenging. Transgenes are subject to the immediate chromatin environment effect that makes them susceptible to three effects: (1) position effects such that identical constructs can have varying expression when integrated into different regions of the host cell genome, (2) heterochromatin spreading in that repressed chromatin often spreads to neighboring DNA unless there is a functional insulator, and (3) de novo methylation in which a genomic region is converted to heterochromatin. This is known as transgene silencing, and occurs both in vitro and in vivo, across all cell types and tissues, and regardless of integration or gene delivery method.

Long-term stable expression of transgenes is of great importance in the field of medicine. Durability of gene expression is essential to the field of gene therapy, especially to avoid redosing patients while providing long-term efficacy of the therapy. Also, manufacture of biotherapeutic protein products (such as antibodies) in mammalian cells depends on stable and high expression. Chromatin position effects make the discovery and maintenance of a highly-producing cell line difficult and expensive. In addition, many animal disease models are made with the addition of a transgene that then needs to be steadily expressed through the lifetime of the animal.

Regulatory elements that address the problem of transgene variegation and silencing to confer long-term expression have traditionally fallen into two categories: passive boundary elements and active chromatin remodelling elements. The most widely used passive boundary element is the chicken B-globin 5'HS4 (cHS4) element, a traditional enhancer-blocking insulator that also functions as a barrier to heterochromatin spreading. In some applications, cHS4 is used to counteract position effects and has conferred some stability to transgenes compared to the lack of an insulator. However, cHS4 and other passive insulators like Matrix Attachment Regions (MARs) can be cumbersome to use because of their requirement to be on either side of the genetic construct. Additionally, the element is highly host cell dependent, with limited utility in non-blood cell lineages. In contrast, active chromatin remodelling elements like ubiquitous chromatin opening elements (UCOEs) have gained popularity in the last decade because of their increased efficacy in resisting silencing. However, UCOE use has largely been limited to the prototypical A2UCOE from the HNRPA2B1-CBX3 locus.

BRIEF SUMMARY

The present disclosure provides a novel ubiquitous chromatin opening element (UCOE) named SRF-UCOE, recombinant polynucleotides, compositions, DNA constructs, expression cassettes, vectors, host cells, and cell culture systems including SRF-UCOE polynucleotide sequences, as well as methods of using the same. Transgenic cells, tissues, and animals comprising a SRF-UCOE nucleotide sequence are also provided. The compositions and methods provided are useful for increasing and/or maintaining expression of a gene of interest.

In one aspect, provided is a recombinant nucleic acid molecule that includes (a) a ubiquitous chromatic opening element (UCOE) polynucleotide comprising a nucleic acid sequence having at least 90% percent sequence identity over the length of the nucleic acid sequence set forth in SEQ ID NO:5; and (b) a heterologous promoter operably linked to the UCOE polynucleotide. In some instances, the recombinant nucleic acid molecule can include a nucleic acid sequence having at least 90% percent sequence identity to the nucleic acid sequence set forth in any of SEQ ID NOs: 1, 2, 3, or 4. In some instances, the recombinant nucleic acid molecule can include a nucleic acid sequence having at least 95% percent sequence identity to the nucleic acid sequence set forth in any of SEQ ID NOs: 1, 2, 3, 4, or 5.

In some instances, the recombinant nucleic acid molecule can also include a gene, wherein the heterologous promoter is operably linked to the gene.

In some instances, the heterologous promoter can be a eukaryotic promoter or a viral promoter. In some instances, the heterologous promoter is a mammalian promoter. In some instances, the heterologous promoter is a tissue-specific promoter.

In another aspect, provided is a vector that contains the recombinant nucleic acid molecule as described above.

In another aspect, provided is a host cell that contains the recombinant nucleic acid molecule or the vector as described above. In some instances, the host cell is a eukaryotic cell. In some instances, the host cell is a bacterial cell.

In another aspect, provided is a composition containing the recombinant nucleic acid molecule, the vector, or the host cell as described above. In some instances, the composition includes a pharmaceutically acceptable carrier.

In another aspect, provided is a method of treating a subject by gene therapy comprising administering to a subject in need of gene therapy an effective dose of the composition described above.

In another aspect, provided is a method of producing a desired gene product that includes the steps of: (a) introducing the recombinant nucleic acid molecule or the vector as described above comprising the gene into a cell line or bacterial strain; and (b) culturing said cell line or bacterial strain to produce the gene product encoded by the gene.

In another aspect, provided is a method of increasing the expression of an endogenous gene in the genome of cell that includes the steps of: (a) introducing the recombinant nucleic acid molecule as described above into the genome of a cell in a position operably associated with the endogenous gene; and (b) culturing said cell.

In another aspect, provided is a transgenic non-human animal containing cells that contain the recombinant nucleic acid molecule or the vector as described above.

In another aspect, provided is a recombinant nucleic acid molecule that contains: (a) a ubiquitous chromatic opening element (UCOE) polynucleotide comprising the nucleic acid sequence of positions 479-780 of SEQ ID NO:1 up to the full length of SEQ ID NO:1; and (b) a heterologous promoter operably linked to the UCOE polynucleotide. In some instances, the UCOE polynucleotide has 90% sequence identity to SEQ ID NOs: 1, 2, 3, or 4. In some instances, the UCOE polynucleotide has 95% sequence identity to SEQ ID NOs: 1, 2, 3, or 4.

In another aspect, provided is a recombinant nucleic acid molecule comprising: (a) a ubiquitous chromatic opening element (UCOE) polynucleotide comprising a nucleic acid sequence having at least 90% percent sequence identity over the length of positions 479-780 of SEQ ID NO:1 up to at least 90% percent sequence identity of the full length of SEQ ID NO:1; and (b) a heterologous promoter operably linked to the UCOE polynucleotide. In some instances, the UCOE polynucleotide has at least 90% sequence identity to SEQ ID NOs: 1, 2, 3, or 4. In some instances, the UCOE polynucleotide has at least 95% sequence identity to SEQ ID NOs: 1, 2, 3, or 4.

BRIEF DESCRIPTION OF THE DRAWINGS

FIG. 1A shows candidate regions identified by the computational algorithm as described in Example 1 according to aspects of this disclosure. "Distance" refers to distance between candidate and HKG.

FIG. 2D shows graphs reflecting the efficacy of candidate UCOE regions to delay transcriptional silencing from the promoters of the stable Ef1α-GFP/hPGK-PuroR expression construct following transduction into P19 cells according to aspects of this disclosure. The assay is the same stable transfection screen format described for FIG. 2B. After puromycin removal at day 0, cells are passaged and assayed for % GFP+ cells every 2-3 days until day 18 for the following conditions: EF1a negative control (top left); A2UCOE and 3'UCOE (top right); Candidates 1, 1R, and 3 (middle left); Candidates 6 and 6R (middle right); Candidates 8 and 9R (bottom left); and Candidates 10 and 10R (bottom right). All replicates are shown with the same symbol. Data in FIG. 2B is the difference between the final and initial time points.

FIG. 6A shows that GFP expression is rescued by treatment with DNA methylation inhibitor 5-aza-cytidine (5-aza) in day 18 UCOE-CMV cells from the lentiviral silencing experiment. Cells were replica plated at day 16, specified concentrations of 5-aza were introduced 24 hours later (with exception of control), and cells were passaged and assayed via flow cytometry 24 hours after chemical introduction for % GFP+ cells. Data is reported as mean±SD from three biological replicates. In the graph, data is shown from left to right for each construct: no treatment, 2 μM 5-aza, 10 μM 5-aza. FIG. 6B shows that GFP expression is rescued by treatment with HDAC inhibitor trichostatin A (TSA) in day 24 UCOE-CMV cells from the lentiviral silencing experiment. Cells were replica plated at day 22, specified concentrations of TSA were introduced 24 hours later (with exception of control), and cells were passaged and assayed via flow cytometry 24 hours after chemical introduction for % GFP+ cells. Data is reported as mean f SD from three biological replicates. In the graph, data is shown from left to right for each construct: no treatment, 0.05 μM TSA, 0.1 μM TSA. FIG. 6C and FIG. 6D show that UCOE candidates linked to the EF1a or PGK promoters, respectively, demonstrate GFP expression rescue by treatment with HDAC inhibitor trichostatin A (TSA) or DNA methylation inhibitor 5-aza-cytidine (5-aza) on day 21. Cells were replica plated at day 19, treated with 0.1 μM TSA or 10 μM 5-aza (with exception of control) 24 hours later, and cells were passaged and assayed via flow cytometry 24 hours after chemical introduction for % GFP+ cells. Data is reported as mean f SD from three biological replicates. In the graphs for FIG. 6C and FIG. 6D, the data is shown from left to right for each construct: no treatment, 0.1 μM TSA, 10 μM 5-aza.

FIG. 7 shows a sequence alignment of the Candidate 6 (SRF-UCOE) nucleic acid sequence (SEQ ID NO:1) with truncation constructs 6-1, 6-2, and 6-3 (SEQ ID NOs: 2-4) as well as the core sequence shared amongst all four (SEQ ID NO:5) according to aspects of this disclosure.

DETAILED DESCRIPTION

Provided in this disclosure is a novel chromatin-opening element, named herein as SRF-UCOE, and methods of use thereof. The SRF-UCOE element was identified as nucleic acid sequence located on chromosome 9 in the Human Surfeit Locus, particularly encompassing the region between and including parts of the first introns of the SURF1 and SURF2 genes. The SRF-UCOE element acts in a modular fashion and confers anti-silencing activity to operatively linked heterologous promoters. The SRF-UCOE element addresses the problems of position effects, heterochromatin spreading, and de novo methylation as known to impact transgene expression. The SRF-UCOE element will find utility in synthetic biology, biomanufacturing, and gene and cell therapy.

The provided SRF-UCOE element has several advantages over existing methods, devices or materials. First, it is an entirely different sequence from a different area of the genome as compared to the existing A2UCOE between the CBX3 and HNRPA2B1 genes (and much lesser used UCOEs from the TBP and RPS3 loci). Second, it matches or outperforms the previously characterized A2UCOE and its most popular truncation when paired with commonly used promoters. Third, at approximately 1002 base pairs or less, it is smaller in size relative to other existing UCOEs, which poses a great advantage because many viruses have restrictive size constraints for the delivery DNA. Fourth, as discussed further below, it lacks synthetic promoter activity, which makes the element safer/avoids oncogenic effects that have plagued early gene therapy trials. This also allows its use with tissue-specific promoters.

The human Surfeit housekeeping locus is a unique, highly conserved cluster of six housekeeping genes. The human Surfeit locus spans approximately 60 kb and is located on 9q34.2. The orientation of each gene alternates from its neighbor, making it a locus of multiple divergent housekeeping gene promoters. The locus comprises bi-directional promoters between the SURF5 and SURF3 genes and between the SURF1 and SURF2 genes. As assessed by others, prior to this disclosure, there has been no indication that these regions open chromatin or maintain chromatin in an open state and facilitate reproducible expression of an operably-linked gene in cells of at least two different tissue types. See, for example, U.S. Pat. No. 7,442,787.

Figure 2A:
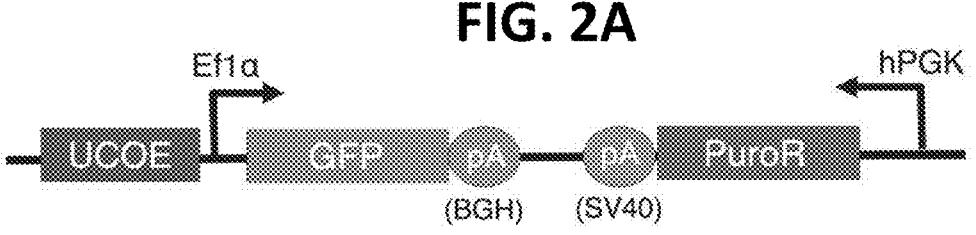
FIG. 2A shows a schematic of the dual expression construct used for screening putative UCOEs for anti-silencing activity in stable transfections according to aspects of this disclosure. The expression construct includes an Ef1α-GFP cassette and a hPGK-PuroR cassette positioned relative to each other so as transcription therefrom will run in opposing directions and having back-to-back polyA terminators (pA: Ef1α-GFP-BGH polyA tail; hPGK-PuroR-SV40 polyA tail).
Figure 2B:
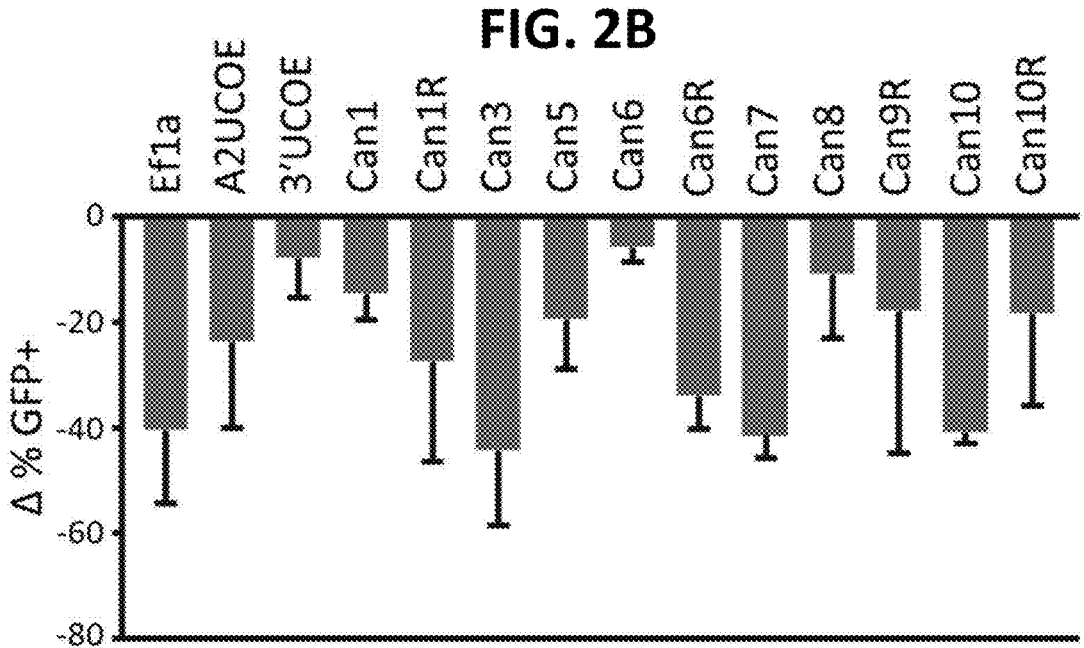
FIG. 2B shows a graph reflecting the silencing expression data of UCOE candidates linked to the Ef1α promoter after stable transfection of P19 cell lines according to aspects of this disclosure. The candidate regions tested were Candidates 1, 1R, 3, 5, 6, 6R, 7, 8, 9R, 10, and 10R, with "R" denoting that the reverse orientation of the candidate region was tested. As a negative control, the stable expression construct without a UCOE or candidate region was assessed (Ef1a). As a positive control, the 2.2 kB A2UCOE sequence, as well as the 1.2 kB reverse orientation sequence 3'UCOE, were cloned into the same reporter construct as the candidate sequences. The percent GFP positive in the population was monitored as a metric for silencing by flow cytometry analysis with each passage, with the change (difference between final and initial time points) plotted on the graph (Δ% GFP+).
Figure 2C:
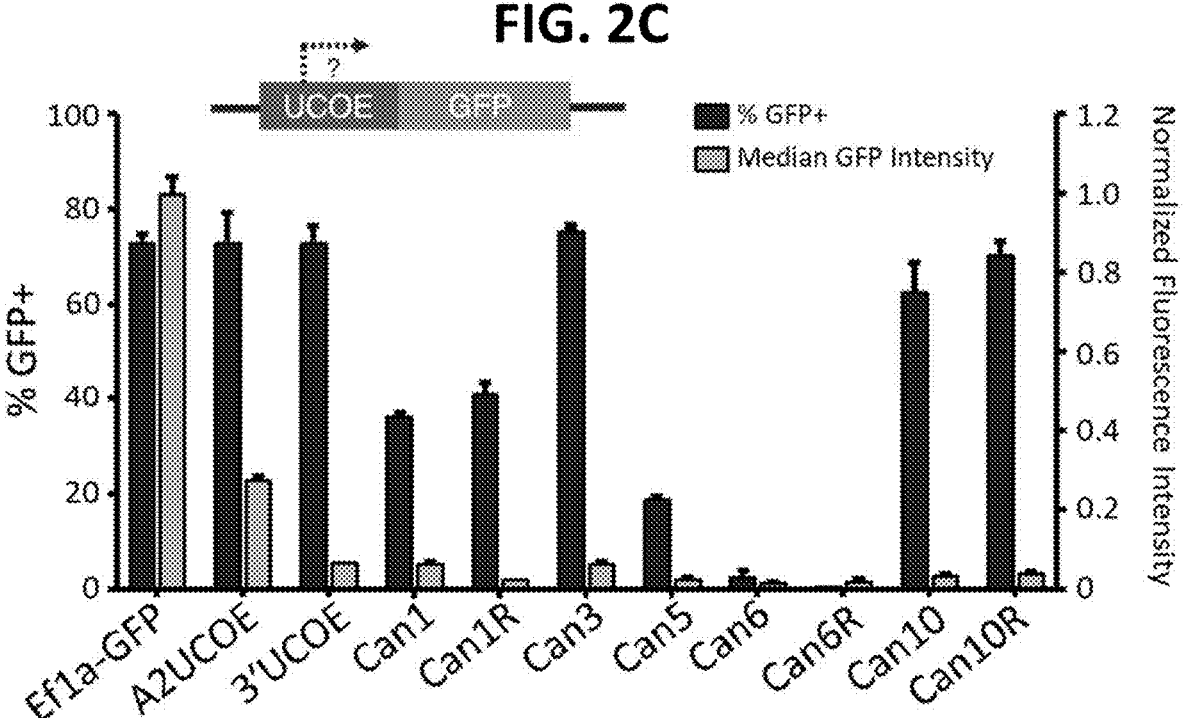
FIG. 2C shows the results of assessing the intrinsic promoter activity of UCOE candidate regions according to aspects of this disclosure. A schematic representation of the expression construct in which the candidate region (UCOE) is inserted upstream of the GFP gene in the absence of any other promoter sequences as used is shown as an inlay. As positive controls, the Ef1α promoter, the 2.2 kB A2UCOE sequence, and the 1.2 kB reverse orientation sequence 3'UCOE, were cloned into the same reporter construct as the candidate sequences. The percent GFP positive in the population was monitored as a metric for gene expression by flow cytometry analysis with each passage (% GFP). Stably transfected cells were assayed for % GFP+ and median fluorescent intensity (normalized to Ef1a promoter control). Data is reported as mean±SD from biological duplicates.

As described in this disclosure, the SRF-UCOE element does not initiate transcription in synthetic constructs comprising a gene that is not otherwise operably linked to a promoter sequence as shown, for example in FIG. 2C and described in Example 3. These results suggest that the endogenous promoter activity of this region must be mediated by additional environmental components. As with most housekeeping genes, this region does not contain a TATA box but does have a strongly predicted SP2 transcription factor binding site according to the comprehensive database of TFBS binding profiles, JASPAR (24). The lack of an inherent transcriptional activity in non-natural constructs makes the element a more modular component that can be paired with promoters of desired strengths for a given application. This lack of inherent transcriptional activity in non-natural constructs also reduces the possibility of unwanted off-target effects of a bidirectional promoter upon random integration, a previously identified disadvantage of A2UCOE (9). Contrary to prior conventional thinking that the mechanism of chromatin opening for UCOEs is directly tied to its mediation of bidirectional transcriptional activity, the chromatin opening function of the SRF-UCOE element is not tied to its functionality as a promoter.

A. SRF-UCOE Polynucleotides

The SRF-UCOE element polynucleotides of the invention include the sequences set forth in SEQ ID NOs: 1-5 and active fragments and variants thereof. Such sequences can be used to produce transgenic cells and organisms. The transformed organisms are characterized by genomes that comprise at least one stably incorporated DNA construct comprising a nucleic acid sequence for the SRF-UCOE element as disclosed herein. The full length SRF-UCOE polynucleotide as set forth in SEQ ID NO:1 is provided as well as modified versions thereof such as, for example, the polynucleotide sequences set forth in SEQ ID NOs: 2-5. In one aspect, provided is a polynucleotide comprising a sequence as set forth in SEQ ID NOs:1-5 or a variant thereof.

An alignment of SRF-UCOE sequences as set forth in SEQ ID NOs: 1-5 is shown in FIG. 7. In some embodiments, the SRF-UCOE element is the nucleic acid sequence set forth in SEQ ID NO: 1, reflecting the full length non-variant sequence. In some embodiments, the SRF-UCOE element comprises the nucleic acid sequence set forth in SEQ ID NO:2, reflecting a truncated variant sequence having a 106 base pair 5' end deletion. In some embodiments, the SRF-UCOE element comprises the nucleic acid sequence set forth in SEQ ID NO:3, reflecting a truncated variant sequence having a 478 base pair 5' end deletion. In some embodiments, the SRF-UCOE element comprises the nucleic acid sequence set forth in SEQ ID NO:4, reflecting a truncated variant sequence having a 241 base pair 3' end deletion. In some embodiments, the SRF-UCOE element comprises the nucleic acid sequence set forth in SEQ ID NO:5, reflecting a core sequence of 283 base pairs. In some instances, the SRF-UCOE element is up to 1002 nucleotides in length. In some instances, the SRF-UCOE element is from 283 to 1002 nucleotides in length.

In some embodiments, the SRF-UCOE element of this disclosure comprises the 5' untranslated region (UTR), the first intron, and the first and second exons of the human SURF1 gene. In some embodiments, the SRF-UCOE element comprises the 5' UTR, the first intron, and the first exon of the human SURF2 gene. In some embodiments, the SRF-UCOE element comprises the 5' UTR, the first intron, and the first and second exons of the human SURF2 gene. In some embodiments, the SRF-UCOE element comprises a methylation-free CpG island located within the first 600 base pairs of the human SURF2 gene. CpG-islands have an average GC content of approximately 60%, compared with a 40% average in bulk DNA. In some embodiments, the SRF-UCOE element comprises a CTCF element located within the first 600 base pairs of the human SURF1 gene. In some embodiments, the SRF-UCOE element comprises a CTCF element located within the first 600 base pairs of the human SURF2 gene. In some embodiments, the SRF-UCOE element comprises a one or more DNaseI hypersensitivity sites located within the first 600 base pairs of the human SURF1 gene and the first 600 base pairs of the human SURF2 gene.

In one aspect, the SRF-UCOE element, or active fragments or variants thereof, has chromatin opening activity. Open chromatin or chromatin in an open state refers to chromatin in a de-condensed state and is also referred to as euchromatin. Condensed chromatin is also referred to as heterochromatin. Chromatin in a closed (condensed) state is transcriptionally silent. Chromatin in an open (de-condensed) state is transcriptionally competent. The establishment of an open chromatin structure is characterized by DNase I sensitivity, DNA hypomethylation and histone hyperacetylation. Standard methods for identifying open chromatin are well-known to those skilled in the art and are described in Wu, 1989, Meth. Enzymol., 170, 269-289 (27); Crane-Robinson et al., 1997, Methods, 12, 48-56 (28); Rein et al., 1998, N.A.R., 26, 2255-2264 (29).

Active fragments and variants of the SRF-UCOE element disclosed herein will retain chromatin opening activity. Chromatin opening comprises the ability of the composition to achieve an observable effect in retaining an open chromatin state or diminishing the occurrence of a closed chromatin state as detected by expression of a gene operably linked to the SRF-UCOE element, or an active fragment or variant thereof, and a heterologous promoter. Such activity may also be measured by the extent of DNase I sensitivity, DNA hypomethylation and histone hyperacetylation at the operably linked gene. Such activity can comprise any statistically significant retention in gene expression, DNase I sensitivity, DNA hypomethylation, and/or histone hyperacetylation, including, for example retention of about 5%, 10%, 15%, 20%, 25%, 30%, 35%, 40%, 45%, 50%, 55%, 60%, 65%, 70%, 75%, 85%, 90%, 95%, or greater.

The term "fragment" refers to a portion of a SRF-UCOE polynucleotide sequence as described in this disclosure. "Fragments" or "biologically active portions" include polynucleotide sequences comprising a sufficient number of contiguous nucleic acid residues to retain the biological activity of the element, i.e., have chromatic opening activity. Fragments of the SRF-UCOE polynucleotide sequence include those that are shorter than the full-length sequence. A biologically active portion of a SRF-UCOE polynucleotide sequence can be a polynucleotide sequence that is, for example, 100, 150, 200, 250, 300, 350, 400, 450, 500, or more nucleic acids in length of any one of SEQ ID NOs: 1-4. Such biologically active portions can be prepared by recombinant techniques and evaluated for chromatic opening activity. As used here, a fragment comprises at least 25 contiguous nucleic acids of SEQ ID NOs: 1-5. Exemplary active SRF-UCOE polynucleotide fragments include SEQ ID NOs: 2, 3, and 4 as shown, for example, in FIG. 3A, FIGS. 4A-4B, FIG. 5A-5B, FIGS. 6A-6D, and FIG. 7 and described in Examples 4-6. In some instances, the biologically active portion of the SRF-UCOE polynucleotide is less than 1002 nucleotides in length. In some instances, the biologically active portion of the SRF-UCOE polynucleotide is at least 283 nucleotides in length. In some instances, the biologically active portion of the SRF-UCOE polynucleotide is less than 1002 nucleotides in length.

It is recognized that modifications may be made to the SRF-UCOE polynucleotide sequence provided herein creating variant SRF-UCOE sequences. Changes designed by man may be introduced through the application of site-directed mutagenesis techniques. Conservative amino acid substitutions may be made in nonconserved regions that do not alter the function of the SRF-UCOE polynucleotide sequence. Alternatively, modifications may be made that improve the activity of the element.

By "variants" is intended to mean substantially similar sequences. For the SRF-UCOE element, a variant comprises a deletion and/or addition of one or more nucleotides at one or more internal sites within the native polynucleotide and/or a substitution of one or more nucleotides at one or more sites in the SRF-UCOE polynucleotide as set forth in any of SEQ ID NOs: 1-6.

Variants of the SRF-UCOE polynucleotide of the invention can also be evaluated by comparison of the percent sequence identity between the variant polynucleotide and the SRF-UCOE polynucleotide. Thus, for example, an isolated polynucleotide with a given percent sequence identity to the polynucleotide of SEQ ID NO: 1-6 are provided. Percent sequence identity between any two polynucleotides can be calculated using sequence alignment programs and parameters described elsewhere herein. Where any given pair of polynucleotides of the disclosure is evaluated by comparison of the percent sequence identity, the percent sequence identity between the two polynucleotides is at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more sequence identity to SEQ ID NOs: 1-6. In some embodiments, the variant has at least 90%, 91%, 92%, 93%, 94%, 95%, 96%, 97%, 98%, or 99% identity to the polynucleotide sequence set forth in any of SEQ ID NO: 1-6. In some embodiments, a biologically active variant of the SRF-UCOE polynucleotide may differ by as few as 1-15 nucleotides, as few as 1-10, such as 6-10, as few as 5, as few as 4, as few as 3, as few as 2, or as few as 1 nucleotides. In some embodiments, a biologically active variant of the SRF-UCOE polynucleotide of SEQ ID NO:5 may differ by up to 30 nucleotides, up to 25-30, up to 10-25, such as 15-20, up to 15, up to 10, up to 5, up to 3, or up to 2 nucleotides. In some embodiments, biologically active variant of the SRF-UCOE polynucleotide of any of SEQ ID NO: 1-4 may differ by up to 100 nucleotides, up to 50-75, such as 30-50, up to 50, up to 40, up to 30, up to 20, up to 10, or up to 5 nucleotides. In specific embodiments, the variant polynucleotides can comprise an 3' or a 5' end truncation, which can comprise at least a deletion of 10, 15, 20, 25, 30, 35, 40, 45, or 50 nucleotides or more from either the 3' or a 5' end of the SRF-UCOE polynucleotide.

The terms "identity" or "percent identity", in the context of two or more nucleic acids or polypeptide sequences, refer to two or more sequences or subsequences that are the same or have a specified percentage of nucleotides or amino acid residues that are the same (e.g., at least 60%, at least 65%, at least 70%, at least 75%, at least 80%, at least 85%, at least 90%, or at least 95% or greater identity over a specified region), when compared and aligned for maximum correspondence over a comparison window, or designated region, as measured using one of the following sequence comparison algorithms or by manual alignment and visual inspection. The percent nucleic acid sequence identity is obtained by counting the number of identical matches (i.e., same residue) after aligning the sequences and introducing gaps, if necessary, to achieve the maximum percent sequence identity (i.e., the sequences are optimally aligned), and dividing such number of identical matches by the length of the aligned sequences.

Two sequences are "optimally aligned" when they are aligned for similarity scoring using a defined nucleic acid substitution matrix (e.g., BLOSUM62 or BLOSUM50), gap existence penalty and gap extension penalty so as to arrive at the highest score possible for that pair of sequences. The gap existence penalty is imposed for the introduction of a single nucleic acid gap in one of the aligned sequences, and the gap extension penalty is imposed for each additional empty nucleic acid position inserted into an already opened gap. The alignment is defined by the nucleic acids positions of each sequence at which the alignment begins and ends, and optionally by the insertion of a gap or multiple gaps in one or both sequences, so as to arrive at the highest possible score. Methods of alignment of sequences for comparison are well known in the art, e.g., visual alignment or using publicly available software using known algorithms to achieve maximal alignment. While optimal alignment and scoring can be accomplished manually, the process is facilitated by the use of a computer-implemented alignment algorithm, as described below.

Unless otherwise stated, identity and similarity will be calculated by the Needleman-Wunsch global alignment and scoring algorithms (Needleman and Wunsch (1970) *J. Mol. Biol.* 48(3):443-453 (30)) as implemented by the "needle" program, distributed as part of the EMBOSS software package (Rice, P. et al., *Trends in Genetics* 16(6): 276-277 (31), versions 6.3.1 available from EMBnet at various sources) using default gap penalties and scoring matrices (EBLO-SUM62 for protein and EDNAFULL for DNA). Equivalent methods may also be used. By "equivalent method" is intended any sequence comparison method that, for any two sequences in question, generates an alignment having identical nucleotide residue matches and an identical percent sequence identity when compared to the corresponding alignment generated by needle from EMBOSS version 6.3.1.

Optimal alignment of sequences for comparison can also be conducted, for example, by manual alignment and visual inspection (see, e.g., Ausubel et al., *Current Protocols in Molecular Biology* (1995 supplement)), by the local homology algorithm of Smith and Waterman, *Adv. Appl. Math.* 2:482, 1970, by the search for similarity method of Pearson and Lipman, *Proc. Natl. Acad. Sci. UA* 85:2444, 1988, by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)). An additional method is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the BLAST programs of Altschul et al. (1990) J. Mol. Biol. 215(3):403-410. BLAST nucleotide searches can be performed with the BLASTN program (nucleotide query searched against nucleotide sequences) to obtain nucleotide sequences homologous to the SRF-UCOE element of the invention. To obtain gapped alignments for comparison purposes, Gapped BLAST (in BLAST 2.0) can be utilized as described in Altschul et al. (1997) *Nucleic Acids Res.* 25:3389-3402 and made available to the public at the website for the National Center for Biotechnology Information and the National Institute of Health. Optimal alignments, including multiple alignments, can be prepared using, e.g., PSI-BLAST, available through www.ncbi.nlm.nih.gov and described by Altschul et al. (1997) supra. PSI-Blast can be used to perform an iterated search that detects distant relationships between molecules. When utilizing BLAST, Gapped BLAST, and PSI-Blast programs, the default parameters of the respective programs (e.g., BLASTX and BLASTN) can be used. Other publicly available software useful for alignment analysis includes ALIGN, ALIGN-2 (Genentech, South San Francisco, Calif.), and Megalign (DNASTAR).

Recombinant or synthetic nucleic acids encoding the SRF-UCOE element disclosed herein are also provided. Of particular interest are nucleic acid sequences that have been designed for expression in eukaryotes, particularly in mammals. That is, the nucleic acid sequence can be optimized for increased expression in a host animal. In some instances, the nucleic acid sequence can be optimized for increased expression in a specific host animal tissue.

A "recombinant nucleic acid" or "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a SRF-UCOE polynucleotide, or active fragment or variant thereof, such that an additional chemically linked nucleic acid segment is located 3' to the SRF-UCOE polynucleotide. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides up to 1%, 2%, 3%, 4%, 5%, 6%, 7%, 8%, 9%, 10%, 11%, 12%, 13%, 14%, 15%, 20%, 25%, 30%, 35%, 40% of the nucleic acids of the SRF-UCOE polynucleotide. Various methods for making such recombinant polynucleotides include chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide or nucleic acid" comprises at least one of a combination of two or more chemically linked amino acid segments which are not found directly joined in nature.

In some instances, the SRF-UCOE element is operably linked to a heterologous promoter. A "promoter" refers to a DNA sequence recognized by the synthetic machinery of the cell, or introduced synthetic machinery, required to initiate the specific transcription of a gene. As used herein, "heterologous" in reference to a sequence is a sequence that originates from a foreign species, or, if from the same species, is substantially modified from its native form in composition and/or genomic locus by deliberate human intervention. As used herein, "linked" refers to a cis-linkage in which the components so described (e.g., the promoter, the SRF-UCOE element, and/or the gene) are present in a cis relationship on the same nucleic acid molecule. The term "operatively linked" or "operably linked" refers to an arrangement of elements wherein the components so described are configured so as to perform their usual function. In one example, the SRF-UCOE element operably linked to a given promoter is able to facilitate the ability of the promoter to initiate transcription. The SRF-UCOE element need not be contiguous with the promoter, so long as it functions to facilitate the transcriptional initiation activity of the promoter. Thus, for example, intervening sequences can be present between the SRF-UCOE element and the promoter sequence, and the SRF-UCOE element can still be considered "operably linked" to the promoter.

In some embodiments, the SRF-UCOE element and heterologous promoter are operably linked to a gene, such as the coding sequence for a protein or RNA of interest. As used herein, the term "gene" (i.e., "expressible gene") refers to a polynucleotide sequence that encodes a polypeptide or RNA molecule. A "gene product" as used herein refers to a polypeptide or RNA molecule expressed from the polynucleotide sequence of the gene. In some embodiments, a gene can be a cDNA or a genomic DNA sequence.

In some instances, the polynucleotide of the present invention facilitates reproducible expression of an operably-linked gene at a physiological level. By "physiological level", it is meant a level of gene expression at which expression in a cell, population of cells or a patient exhibits a physiological effect. Preferably, the physiological level is an optimal physiological level depending on the desired result. Preferably, the physiological level is equivalent to the level of expression of an equivalent endogenous gene.

The term "facilitates reproducible expression" refers to the capability of the SRF-UCOE element, or active fragment or variant thereof, to facilitate reproducible activation of transcription of the operably-linked gene. The process is believed to involve the ability of the UCOE to render the region of the chromatin encompassing the gene (or at least the transcription factor binding sites) accessible to transcription factors. Reproducible expression preferably means that the polynucleotide when operably-linked to a gene gives substantially the same level of expression of the operably-linked gene irrespective of its chromatin environment and preferably irrespective of the cell tissue type. Preferably, substantially the same level of expression means a level of expression which has a standard deviation from an average value of less than 48%, more preferably less than 40% and most preferably, less than 25% on a per-gene-copy basis. Alternatively, substantially the same level of expression preferably means that the level of expression varies by less than 10-fold, more preferably less than 5-fold and most preferably less than 3-fold on a per-gene-copy basis. In some instances, the level of expression is the level of expression measured in a transgenic animal. In some instances, the SRF-UCOE element, or active fragment or variant thereof, facilitates reproducible expression of an operably-linked gene when present at a single or low (less than 3) copy-number.

B. Expression Cassettes and Vectors

Polynucleotides encoding the SRF-UCOE polynucleotide and active fragments and variants thereof as described herein can be provided in expression cassettes for expression in an organism of interest. The cassette will include 5' and 3' regulatory sequences including a heterologous promoter operably linked to the SRF-UCOE polynucleotide, or active fragment or variant thereof, that allows for expression of a gene of interest that is operably linked to the heterologous promoter and the SRF-UCOE polynucleotide, or active fragment or variant thereof. The cassette may additionally contain at least one additional gene or genetic element to be co-transformed into the organism. Such an expression cassette is provided with a plurality of restriction sites and/or recombination sites for insertion of the gene of interest to be under the transcriptional regulation of the regulatory regions. The expression cassette may additionally contain a selectable marker gene and/or a reporter gene.

In some embodiments, the expression cassette will include in the 5'-3' direction of transcription, the SRF-UCOE polynucleotide, or active fragment or variant thereof, a transcriptional and translational initiation region (i.e., a promoter), a gene (i.e., an expressible gene encoding a protein or RNA of interest), and a transcriptional and translational termination region (i.e., termination region) functional in the organism of interest. The promoters of the invention are capable of directing or driving expression of a gene in a host cell. One or more of the promoter, the translational termination region, and the gene may be endogenous or heterologous to the host cell or to each other. At least one of the promoter, the translational termination region, and the gene is heterologous to the SRF-UCOE polynucleotide. In some instances, at least one of the promoter, the translational termination region, and the gene are heterologous to the others.

Additional regulatory signals include, but are not limited to, transcriptional initiation start sites, operators, activators, enhancers, other regulatory elements, ribosomal binding sites, an initiation codon, termination signals, and the like. Such regulatory signals are discussed generally in Sambrook et al. (1992) Molecular Cloning: A Laboratory Manual, ed. Maniatis et al. (Cold Spring Harbor Laboratory Press, Cold Spring Harbor, N.Y.); Advanced Bacterial Genetics, ed. Davis et al., (1980) (Cold Spring Harbor Laboratory Press), Cold Spring Harbor, N.Y., and the references cited therein.

In some embodiments, the gene is a therapeutic nucleic acid sequence. Therapeutically useful nucleic acid sequences include sequences encoding receptors, enzymes, ligands, regulatory factors, hormones, antibodies or antibody fragments, and structural proteins. Therapeutic nucleic acid sequences also include sequences encoding nuclear proteins, cytoplasmic proteins, mitochondrial proteins, secreted proteins, membrane-associated proteins, serum proteins, viral antigens, bacterial antigens, protozoal antigens, and parasitic antigens. Such nucleic acid sequences also include sequences encoding proteins, peptides, lipoproteins, glycoproteins, phosphoproteins, and nucleic acid (e.g., RNAS or antisense nucleic acids). Proteins or polypeptides which can be encoded by the therapeutic nucleic acid sequence include hormones, growth factors, enzymes, clotting factors, apolipoproteins, receptors, erythropoietin, therapeutic antibodies or fragments thereof, drugs, oncogenes, tumor antigens, tumor suppressors, viral antigens, parasitic antigens, and bacterial antigens. Specific examples of these compounds include proinsulin, growth hormone, androgen receptors, insulin-like growth factor I, insulin-like growth factor II, insulin-like growth factor binding proteins, epidermal growth factor, transforming growth factor α, transforming growth factor β, platelet-derived growth factor, angiogenesis factors (acidic fibroblast growth factor, basic fibroblast growth factor, vascular endothelial growth factor, angiogenin), matrix proteins (Type IV collagen, Type VII collagen, laminin), phenylalanine hydroxylase, tyrosine hydroxylase, oncoproteins (for example, those encoded by ras, fos, myc, erb, Src, neu, sis, jun), HPV E6 or E7 oncoproteins, p53 protein, Rb protein, cytokine receptors, IL-1, IL-6, IL-8, and proteins from viral, bacterial and parasitic organisms which can be used to induce an immunological response, and other proteins of useful significance in the body.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired expression profile. In some embodiments, the promoter is a heterologous promoter. The SRF-UCOE polynucleotide can be combined with any of constitutive, inducible, tissue-specific, and/or other promoters for expression of the gene in the organism of interest. In some embodiments, the promoter is a eukaryotic promoter or a viral promoter. In one example, the promoter is a eukaryotic promoter such as a mammalian promoter. Exemplary mammalian promoters are the EF1α, promoter, the PGK promoter (human and/or mouse) and the U6 promoter. In another example, the promoter is a viral promoter. Exemplary viral promoters include the CMV promoter, the RSV promoter, the SFFV promoter and the SV40 promoter. In some instances, the promoter is a strong and/or substantially ubiquitous promoter.

The expression cassette can also comprise a selectable marker gene for the selection of transformed cells. Selectable marker genes are utilized for the selection of transformed cells or tissues. Marker genes include genes encoding antibiotic resistance, such as those encoding puromycin N-acetyl-transferase (PAC), neomycin phosphotransferase II (NEO), and hygromycin B phosphotransferase (HPT). Additional selectable markers are known and any can be used.

Also provided in this disclosure is a vector comprising the SRF-UCOE polynucleotide. The vector preferably comprises a gene operably-linked to the SRF-UCOE polynucleotide. The vector can comprise any of the elements and embodiments discussed above with respect to the expression cassette provided. In some embodiments, the gene comprises the necessary elements enabling gene expression such as suitable promoters, enhancers, splice acceptor sequences, internal ribosome entry site sequences (IRES) and transcription stop sites. Suitable elements for enabling gene expression are well known to those skilled in the art. The suitable elements for enabling gene expression can be the natural endogenous elements associated with the gene or may be heterologous elements used in order to obtain a different level or tissue distribution of gene expression compared to the endogenous gene. Preferably, the vector comprises a promoter operably associated with the gene and the SRF-UCOE polynucleotide. The promoter may be a natural endogenous promoter of the gene or may be a heterologous promoter as discussed above.

The vector may be any vector capable of transferring DNA to a cell. In some embodiments, the vector is an integrating vector or an episomal vector. In some instances, the integrating vector can be a recombinant lentivirus vector. A recombinant lentivirus vector will include DNA of at least a portion of a lentivirus genome which portion is capable of infecting the target cells. The term "infection" is used to mean the process by which a virus transfers genetic material to its host or target cell. In some instances, the lentivirus used in the construction of a vector of the invention is also rendered replication-defective to remove the effect of viral replication of the target cells. In such cases, the replication defective viral genome can be packaged by a helper virus in accordance with conventional techniques. Generally, any lentivirus meeting the above criteria of infectiousness and capability of functional gene transfer can be employed in the practice of the invention. Lentiviral vectors are described in Milone, M. C. and O'Doherty (2018) *Leukemia* 32: 1529-1541 (43).

Different types of lentiviral vector systems have been developed that seek to improve lentiviral vector system safety and efficacy. Second generation lentiviral systems contain a single packaging plasmid encoding the Gag, Pol, Rev, and Tat genes. Without an internal promotor, transgene expression is driven by the genomic 5' LTR, which is a weak promotor and requires the presence of Tat to activate expression. Third generation systems improve on the safety of the second generation system in two ways. First, the packaging system is split into two packaging plasmids: one encoding Rev and one encoding Gag and Pol. Second, Tat is eliminated from the third generation system; expression of the transgene from this promoter is no longer dependent on Tat transactivation. A third generation transfer plasmid can be packaged by either a second or a third generation packaging system. While the second and third generation systems address concerns related to unintentional generation of replication-competent viruses, the systems are still vulnerable to causing mutagenesis and off target effects in transduced cells.

Other vectors useful in the present invention include adenovirus, adeno-associated virus, SV40 virus, vaccinia virus, HSV and pox virus vectors. In some instances, the vector is an adenovirus transfer vector. Adenovirus vectors are well-known to those skilled in the art and have been used to deliver genes to numerous cell types, including airway epithelium, skeletal muscle, liver, brain and skin (Hitt, M. M. et al. (1997) *Advances in Pharmacology* 40: 137-206 (33); Anderson, W. F. (1998) *Nature* 392 (6679 Suppl):25-30 (34)). In some instances, the vector is an adeno-associated (AAV) vector. AAV vectors are well-known to those skilled in the art and have been used to stably transducer human T-lymphocytes, fibroblasts, nasal polyp, skeletal muscle, brain, erythroid and hematopoietic stem cells for gene therapy applications (Philip, R. et al., 1994, *Mol. Cell. Biol.* 14, 2411-2418 (35); Russell, D. W. et al., 1994, *PNAS USA* 91(19): 8915-8919 (36); Flotte. T. R. et al., 1993, *PNAS USA* 90(22): 10613-10617 (37); Walsh, C. E. et al., 1992, *PNAS USA* 89(15):7257-7261 (38); Miller, J. L. et al., 1994, *PNAS USA* 91(21), 10183-10187 (39); Emerson, 1996, *Blood* 87, 3082-3088 (40); Naso, M. F. et al. (2017) *BioDrugs* 31(4): 317-334 (41)). Episomal vectors can include transient non-replicating episomal vectors and self-replicating episomal vectors with functions derived from viral origins of replication such as those from EBV, human papovavirus (BK) and BPV-1. In some instances, the vector may be a replicating episomal vector. Such vectors have a larger size capacity than many viral vectors and have less risk of insertional mutagenesis. Such integrating and episomal vectors are well-known to those skilled in the art. Certain suitable episomal vectors are described in Ehrhardt, A. et al. (2008) Current Gene Therapy, 8(3):147-161 (42). In some embodiments, the vector is a mammalian artificial chromosome. The use of mammalian artificial chromosomes is discussed by Kazuki, Y. and Oshimura, M. (2011) *Mol. Therapy* 19(9): 1591-1601 (44).

In some embodiments, the vector is a plasmid. For example, the plasmid can be a non-replicating, non-integrating plasmid. The term "plasmid" as used herein refers to any nucleic acid encoding a gene and includes linear or circular nucleic acids and double or single stranded nucleic acids. The nucleic acid can be DNA or RNA and may comprise modified nucleotides or ribonucleotides, and may be chemically modified by Such means as methylation or the inclusion of protecting groups or cap- or tail structures. A non-replicating, non-integrating plasmid is a nucleic acid which when transfected into a host cell does not replicate and does not specifically integrate into the host cell's genome (i.e. does not integrate at high frequencies and does not integrate at specific sites). In some instances, the plasmid is a naked nucleic acid. As used herein, the term "naked" refers to a nucleic acid molecule that is free of direct physical associations with proteins, lipids, carbohydrates or proteoglycans, whether covalently or through hydrogen bonding. The term does not refer to the presence or absence of modified nucleotides or ribonucleotides, or chemical modification of the all or a portion of a nucleic acid molecule by such means as methylation or the inclusion of protecting groups or 5' cap and/or poly A elements.

C. Transformed Cells and Animals

Also provided in this disclosure are transformed cells, cell tissue, and organisms are provided comprising the SRF-UCOE polynucleotide or active fragment or variant thereof. In one aspect, provided is a host cell into which a DNA construct comprising the SRF-UCOE polynucleotide or active fragment or variant thereof of this disclosure has been introduced. DNA constructs comprising the SRF-UCOE polynucleotide or active fragment or variant thereof can be used to transform cells of organisms of interest. Methods for transformation involve introducing a nucleotide construct into a host cell. By "introducing" is intended to introduce a construct comprising the SRF-UCOE polynucleotide (e.g., alone or as part of an expression cassette or vector) into a host cell in such a manner that the construct gains access to the interior of the host cell. The methods of the invention do not require a particular method for introducing a nucleotide construct to a cell, only that the nucleotide construct gains access to the interior of the host cell or at least one cell of a host organism. Methods for introducing nucleotide constructs into cells are known in the art including, but not limited to, stable transformation methods, transient transformation methods, and virus-mediated methods.

The host cell may be any cell such as bacterial cells, yeast cells, insect cells, and mammalian cells. In some embodiments, the host cell is a mammalian cell. In some instances, the host cell is a non-human mammalian cell. In some instances, the host cell is a human cell. In some instances, mammalian host cells can be derived from mammalian cell lines such as the CHO cell line, the 293 cell line, the NS0 cell line, the P19 cell line, the Jurkat cell line, the K562 cell line, and the Hs68 cell line. In some instances, the mammalian cell line is the CHO cell line, which has been used in biomanufacturing of proteins as described above. In some embodiments, the host cell is an embryonic stem (ES) cell. ES cells are pluripotent stem cells derived from the inner cell mass of a blastocyst, an early-stage embryo. In other embodiments of the invention, the host cell is an induced pluripotent stem cell (iPS cells or iPSC). iPS cells are a type of pluripotent stem cell artificially derived from a non-pluripotent cell—typically an adult somatic cell—by inducing expression of specific genes (e.g., at least Oct-3/4 (Pou5f1), Sox2). iPS cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. iPS cells can be generated from a variety of adult somatic cells, including, e.g., stomach cells, liver cells, skin cells and blood cells. In another embodiment, the host cell is a primary cell obtained from a subject, such as a human subject or a mouse subject. For example, primary cells can include human foreskin fibroblasts (HFF), adipose-derived stem cells (ADSC), dermal fibroblasts, and epithelial cells.

"Transgenic cells" or "transformed cells" or "stably transformed" or "transduced cells" cells or tissues refers to cells that have incorporated or integrated the SRF-UCOE polynucleotide or active fragment or variant thereof. In some instances, the polynucleotide is part of a DNA construct or an expression cassette as described above. In some instances, the polynucleotide is part of a vector as described above. It is recognized that other exogenous or endogenous nucleic acid sequences or DNA fragments may also be incorporated into the host cell. Numerous techniques are known and are useful according to the invention for delivering the vectors described herein to cells. Transformation may be performed, for example, by any of infection, transfection, transduction, conjugation, microinjection, electroporation, microprojection, biolistics or particle bombardment, electroporation, silica/carbon fibers, ultrasound mediated, PEG mediated, calcium phosphate co-precipitation, polycation DMSO technique, DEAE cellulose and Dextran procedures, heat shock, viral mediated, liposome mediated (e.g., polybrene, lipopolyamines, poly-L-ornithine), and the like. Transformation protocols as well as protocols for introducing polynucleotide sequences into host cells may vary depending on the type of cell, i.e., prokaryotic, eukaryotic, targeted for transformation. Methods for transformation are known in the art. Transformation may result in stable or transient incorporation of the nucleic acid into the cell. "Stable transformation" is intended to mean that the nucleotide construct introduced into a host cell integrates into the genome of the host cell and is capable of being inherited by the progeny thereof. "Transient transformation" is intended to mean that a polynucleotide is introduced into the host cell and does not integrate into the genome of the host cell. In some embodiments, a vector of the invention may be delivered to a host cell non-specifically or specifically (i.e., to a designated subset of host cells) via a viral or non-viral means of delivery. Delivery methods of viral origin include viral particle packaging cell lines as transfection recipients for the vector of the present invention into which viral packaging signals have been engineered, such as those of adenovirus, herpes viruses, lentiviruses, and papovaviruses. Non-viral based gene delivery means and methods may also be used in the invention and include direct naked nucleic acid injection, nucleic acid condensing peptides and non-peptides, cationic liposomes and encapsulation in liposomes.

In specific embodiments, the sequences provided herein can be targeted to specific cite within the genome of the host cell. Such methods include, but are not limited to, meganucleases designed against the host genomic sequence of interest (Silva, G. et al. (2011) *Current Gene Therapy* 11(1): 11-27 (45)); CRISPR-Cas9, TALENs, and other technologies for precise editing of genomes (Rojo, P. et al. (2018) *Bioengineered* 9(1): 214-221 (45); Liu, C. et al., *J. Control Release* 266: 17-26 (46)); Cre-lox site-specific recombination; FLP-FRT recombination: Bxbl-mediated integration; zinc-finger mediated integration; and homologous recombination as are well known in the art.

The SRF-UCOE polynucleotide or active fragment or variant thereof may be inserted into the genome of a cell in a position operably associated with an endogenous (native)

gene and thereby lead to increased expression of the endogenous gene. Alternatively, the SRF-UCOE polynucleotide in its endogenous (native) position on the genome may have a gene inserted in an operably associated position downstream thereof so that expression of the gene occurs. In such instances, transgene design and integration site selection may be considered so as to not disrupt gene expression within the native Surfeit locus upon integration thereof.

In one aspect, provided is also a eukaryotic cell whose genome comprises the SRF-UCOE nucleic acid sequence or an active fragment or variant thereof upstream of a promoter operably linked to a gene. In some instances, the eukaryotic cell is a human cell. In some instances, the eukaryotic cell is a non-human mammal cell.

In some aspects, the host cell of this disclosure is an ES cell that can be used to generate transgenic animals using techniques well known in the art, which comprise injection of the ES cell into a blastocyst followed by implantation of chimeric blastocysts into females to produce offspring which can be bred and selected for homozygous recombinants having the required insertion. In some embodiments, the transgenic animal is a chimeric animal comprising ES cell-derived tissue and host embryo derived tissue.

In one aspect, provided is a method for producing a transgenic non-human mammal that has stable expression of a gene of interest, the method comprising (a) inserting the SRF-UCOE nucleic acid sequence or an active fragment or variant thereof upstream of a promoter operably linked to a gene into the genome of a non-human mammal ES cell genome, (b) injecting the non-human mammal ES cell into a non-human mammal blastocyst of the same species to create a chimeric blastocyst; (c) implanting the chimeric blastocyst into a mature non-human mammal female; and (d) obtaining a transgenic non-human mammal as the progeny of the mature non-human mammal female resulting from the chimeric blastocyst.

In another aspect, provided herein is also a non-human animal whose genome comprises the SRF-UCOE nucleic acid sequence or an active fragment or variant thereof upstream of a promoter operably linked to a gene. In some instances, the animal is a non-human mammal. In some embodiments, the non-human mammal is a rodent, such as a mouse or rat, and cells of the invention, are rodent cells or ES cells, such as mouse ES cells. Transgenic animals containing the SRF-UCOE nucleic acid sequence or an active fragment or variant thereof may be used for long-term production of a protein of interest.

The present disclosure also provides the use of the polynucleotide of the present invention in producing transgenic non-human animals. The present invention also provides a non-human animal containing cells which contain a SRF-UCOE polynucleotide or active fragment or variant thereof.

D. Compositions and Methods of Use

As discussed above, the present disclosure provides SRF-UCOE polynucleotides as well as vectors and host cell. In some instances, these compositions are used in gene therapy.

In one aspect, provided in this disclosure is a pharmaceutical composition comprising the SRF-UCOE polynucleotides, vectors, or host cells as described herein in combination with a pharmaceutically acceptable carrier. The pharmaceutical compositions may compromise the SRF-UCOE polynucleotide or active fragment or variant thereof, a vector, or host cell in admixture with a pharmaceutically acceptable carrier or diluent. The term "pharmaceutically acceptable carrier" as used herein is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Exemplary carriers or diluents include, but are not limited to, water, saline, Ringer's solutions, dextrose solution, and 5% human serum albumin. The use of such media and agents is well known in the art. Except insofar as any conventional media or agent is incompatible with the agents provided herein, use thereof in the composition is contemplated. The present disclosure also provides the use of the polynucleotides, vector, or host cell of the present invention in the manufacture of a composition for use in gene therapy.

In another aspect, the present disclosure also provides the SRF-UCOE polynucleotides, vector or host cell described herein as a component of a cell culture system capable of producing a desired gene product. Suitable cell culture systems are well-known to those skilled in the art and are fully described in the body of literature known to those skilled in the art.

In another aspect, the present disclosure provides a method of producing a desired gene product (e.g., a protein or RNA molecule) comprising introducing a recombinant nucleic acid molecule comprising a SFR-UCOE polynucleotide as described herein, or a vector comprising such SFR-UCOE polynucleotide, into a cell line or bacterial strain, wherein the SFR-UCOE polynucleotide is operably linked to a gene upon insertion. The method may comprise further culturing said cell line or bacterial strain to produce the gene product encoded by the gene.

In another aspect, the present disclosure provides a method of producing a increasing the expression of an endogenous gene in the genome of cell comprising introducing a recombinant nucleic acid molecule comprising a SFR-UCOE polynucleotide as described herein, or a vector comprising such SFR-UCOE polynucleotide, into the genome of a cell in a position operably associated with the endogenous gene. The method may comprise further culturing said cell.

In another aspect of this disclosure, provided is a method of maintaining or increasing expression of a gene of interest in a cell, the method comprising inserting the SRF-UCOE nucleic acid sequence or an active fragment or variant thereof upstream of a promoter operably linked to a gene of interest (i.e., an expressible gene) in the genome of the cell.

In some embodiments, the SRF-UCOE element (Candidate 6), or active fragment or variant thereof, is positioned upstream of a heterologous promoter that is operably linked to a gene of interest to modulate strong long-term expression thereof as shown in FIG. 2B, FIGS. 2D-2E, FIGS. 4A-4B, FIGS. 5A-5B, and FIGS. 6A-6D and described in Examples 3-5. In some embodiments, the SRF-UCOE element, or active fragment or variant thereof, prevents transgenes delivered by non-viral (stable transfection) and viral (lentivirus) methods from losing as much expression as the same construct without such element as shown, for example, in FIG. 2B, FIGS. 2D-2E, FIGS. 4A-4B, FIGS. 5A-5B, and FIGS. 6A-6D and described in Examples 3-5. In some embodiments, the SRF-UCOE element stabilizes gene expression in a higher percentage of the cell population than A2UCOE or derivatives thereof as shown, for example, in FIG. 2B, FIGS. 2D-2E, FIGS. 4A-4B, FIGS. 5A-5B, and FIGS. 6A-6D and described in Examples 3-5. In some embodiments, the SRF-UCOE element resists DNA methylation and histone deacetylation as shown, for example, in FIGS. 5A-5B and FIGS. 6A-6D and described in Example 5.

In the provided methods, at least one of the SRF-UCOE, the promoter, or the gene are heterologous with respect to each other. In some instances, the gene of interest is an endogenous gene (native) in the cell genome. In some instances, the promoter is an endogenous promoter (native) in the cell genome and to the gene of interest. In some instances, the gene of interest is an exogenous gene and is inserted together with the SRF-UCOE nucleic acid sequence or an active fragment or variant thereof. In some instances, the promoter is an exogenous promoter to the gene of interest (i.e. a heterologous promoter) and is inserted together with the SRF-UCOE nucleic acid sequence or an active fragment or variant thereof. In some embodiments, the SRF-UCOE nucleic acid sequence or an active fragment or variant thereof is inserted as construct comprising a promoter and, in some instances, a promoter operably linked to a gene of interest. Such methods are performed using the SRF-UCOE polynucleotides, DNA constructs, expression cassettes, and vectors described in this disclosure. Thus, the present disclosure provides the use of the SRF-UCOE polynucleotides described herein to increase the expression of an endogenous gene comprising inserting the polynucleotide into the genome of a cell in a position operably associated with the endogenous gene thereby increasing the level of expression of the gene.

In one aspect of this disclosure, provided is a method of treating a subject by gene therapy comprising administering to a subject in need of gene therapy an effective dose of any of the compositions described herein. In some embodiments, the method comprising inserting the SRF-UCOE nucleic acid sequence or an active fragment or variant thereof upstream of a promoter operably linked to a gene of interest (i.e., an expressible gene) in the genome of the cell. Thus, the method comprises administering to a patient in need of such treatment an effective dose of a SRF-UCOE polynucleotide, a vector, or a host cell as described herein. Generally, the subject is suffering from a disease treatable by gene therapy. In the method of treatment, as described in the preceding paragraph, at least one of the SRF-UCOE, the promoter, or the gene are heterologous with respect to each other.

In the provided method treatment, the SRF-UCOE polynucleotide, vector, or host cell of the disclosure, or a pharmaceutical composition comprising any thereof, may be administered via a route which includes any of systemic intramuscular, intravenous, aerosol, oral (solid or liquid form), buccal, topical, ocular, as a suppository, intraperitoneal, intrathecal injection, and/or local direct injection.

The exact dosage regime will be determined by individual clinicians for individual patients and this, in turn, will be controlled by the exact nature of the protein expressed by the gene of interest and the type of tissue that is being targeted for treatment. The dosage also will depend upon the disease indication and the route of administration. Advantageously, the duration of treatment will generally be continuous or until the cells die. The number of doses will depend upon the disease, and efficacy data from clinical trials. In some embodiments, the amount of polynucleotide or vector DNA delivered for effective gene therapy according to the invention will preferably be in the range of between 50 ng-1000 µg vector DNA/kg body weight of the subject. For example, the amount administered may be in the range of 1-100 µg vector DNA/kg body weight.

The polynucleotide, vector or host cell of this disclosure may be administered to a mammal using in vivo cell uptake or by an ex vivo approach. In some instances, for the ex vivo uptake approach, are removed from a subject, transduced with the polynucleotide or vector, and then reimplanted into the subject. The liver, for example, can be accessed by an ex vivo approach by removing hepatocytes from an animal, transducing the hepatocytes in vitro and re-implanting the transduced hepatocytes into the subject (e.g., as described for rabbits by Chowdhury, M. et al. (1991) *Science* 254 (5039):1802-1805 (47) and in humans by Wilson, J. M. (1992) *Hum. Gene Ther.* 3(2):179-222 (48)). Such methods also may be effective for delivery to various populations of cells in the circulatory or lymphatic systems, such as erythrocytes, T-cells, B cells, and hematopoietic stem cells.

EXAMPLES

The following examples are offered to illustrate, but not to limit the claimed invention.

UCOEs have been defined by their ability to confer reproducible, stable expression of transgenes, even when integrated into centromeric heterochromatin. One particular UCOE sequence from the HNRPA2B1-CBX3 locus (dubbed A2UCOE) has been by far the most studied and utilized of the currently identified UCOEs. The A2UCOE element encompasses a methylation-free CpG island between the HNRPA2B1 and CBX3 housekeeping genes. Stable expression can be achieved from using its innate promoter for HNRPA2B1, or as a regulatory element linked to a heterologous promoter to confer stable long-term transgene expression. Its efficacy has been attributed to its resistance to DNA methylation-mediated silencing and recruitment of chromatin remodellers. A2UCOE has demonstrated its utility in conferring long-term stable expression to gene therapy constructs in a variety of cell types and tissues, both in vitro and in vivo (Dighe, N. et al. (2014) *PLoS One,* 9, e104805 (8); Muller-Kuller, U. et al. (2015) *Nucleic Acids Res,* 43, 1577-1592 (9); Brendel, C. et al. (2012) *Gene Ther,* 19, 1018-1029 (10)) and even in clinically-relevant human iPSCs (Haenseler, W. et al. (2018) *Matters,* DOI: 10.19185/ matters.201805000005 (11)). Additionally, A2UCOE has shown utility in the rapid selection and isolation of highly expressing clones in biomanufacturing to significantly improve titer (Saunders, F. et al. (2015) *PLoS One,* 10, e0120096 (12); Benton, T. et al. (2002) *Cytotechnology,* 38, 43-46 (13); Williams, S. et al. (2005) *BMC Biotechnol,* 5, 17 (14)). Recently, the A2UCOE sequence has been used to confer stability to creating dCas9-effector platform cell lines for doing CRISPRi screens that perturb specific genes to study biological phenomena (Adamson, B. et al. (2016) *Cell,* 167, 1867-1882 e1821 (25); Jost, M. et al. (2017) *Mol Cell,* 68, 210-223 e216 (26). The A2UCOE is described, e.g., in U.S. Pat. No. 7,442,787.

A variety of individual studies have found efficacy from variable lengths of the core sequence (refs 6, 7, 9, 10, 61, 62). There is still a need for a modular single sequence under 1 kb that can predictably stabilize a broad diversity of gene expression constructs. Finally, although A2UCOE seems to maintain the specificity of tissue-specific promoters, there is still a concern that the bidirectional promoter can cause non-specific activation upon integration, and these off-target effects have traditionally been a concern in the gene therapy space. Additional UCOEs with different functionality may be able to address weaknesses and deficiencies of A2UCOE to find utility in more applications, as well as help determine the underlying mechanism of this interesting class of elements.

Example 1: Materials and Methods Used in Example

To develop criteria for identifying potential UCOE elements, particular properties of the A2UCOE locus in the human genome were identified that have been hypothesized to be linked to its mechanism. A2UCOE encompasses divergently transcribed promoters of the HNRPA2B1 and CBX3 housekeeping genes, including a methylation-free CpG island. Distinct histone modification patterns, especially H3 and H4 acetylation, as well as the H3K4me3 mark that is associated with active transcription, have also been studied at this locus (Lindahl Allen, M. and Antoniou, M. (2007) *Epigenetics,* 2, 227-236 (21)). Finally, insulator factor CTCF is known to bind to boundary regions and mediate three-dimensional chromatin loops at epigenetically distinct boundaries, making CTCF binding sites a hallmark of insulators (Weth, O. et al. (2014) *Nucleic Acids Research,* 42, 11941-11951 (54)). With the exact mechanism of A2UCOE's functionality unknown, as unbiased of a feature search as possible was performed, with the hypothesis that there may be other sequences in the human genome that perform similarly.

The human genome was examined through a computational algorithm that identifies areas with similar features to the A2UCOE locus. Because it is a chromatin-remodelling element, the epigenetic signature at the locus was used as the first indicator of UCOE activity. With the causal effect of most histone marks still unknown (Bannister, A. J. and Kouzarides, T. (2011) *Cell Res,* 21, 381-395 (53)), as unbiased of a search as possible was performed by using all 13 of the ChIP-Seq tracks available through the Broad Institute/ENCODE consortium for the GM12878 lymphoblastoid cell line, which the inventors have determined to be the most karyotypically-normal somatic cell line. Regions with the same pattern of presence/absence of histone marks (as well as three other DNA-associated proteins, EZH2, H2AZ, and CTCF, measured in the ChIP-seq) were searched across the hg19/Gr37 human genome assembly. This search resulted in 2,911 candidate regions. As the sequence is a regulatory sequence, these regions were further queried to ensure that they did not fall completely within the coding sequence of genes, using the UCSC Known Genes track. Applying this filter reduced the candidate list to 936 regions. Next, based on 84% overlap of A2UCOE and the CPG island between HRNPA2B1 and CBX3, a condition that the region is strongly composed of a CpG island was applied. Specifically, regions were required to have at least a 50% overlap with a CpG island, bringing the number of candidate regions to 151. To ensure that regions with unmethylated CpG islands were searched, candidate regions were further selected based on Reduced Representation Bisulfite Sequencing (RRBS) data of GM12878 cells, also from the ENCODE project (further described below). The application of this criteria reduced the candidate list to 94 unique regions of the genome. As a final filter, the CTCF binding sites were confirmed with a different dataset from ENCODE, the ENCODE Transcription factor ChIP dataset, which encompassed data across several cell lines (Wang, J. et al. (2013) *Nucleic Acids Res,* 41, D171-176 (52), bringing the number of candidate regions down to 88. The candidate list includes the A2UCOE locus on chromosome 7, and sizes of the candidate regions ranged between 57 to 3916 bp (data not shown).

A. Computational Algorithm for Identifying Putative UCOE Elements in the Human Genome Data for the hg19 assembly of the human genome was downloaded from the appropriate sources: (a) Broad Institute ChIP-seq data for GM12878 cells as part of the ENCODE consortium (13 tracks) (15), (b) University of California Santa Cruz (UCSC) Known Genes Track (16), (c) UCSC Genome Browser CpG Island track, (d) ENCODE Reduced Representation Bisulfite Sequencing (RRBS) in GM12878 (17), and (e) the ENCODE transcription factor ChIP dataset (18).

Briefly, the 13 ChIP-seq tracks (consisting mostly of 11 histone modifications) for GM12878 cells were combined in a binary fashion (present or absent) to return a list of regions that contained the same combination of features. These sequences were then screened to remove regions that fell completely within a gene's coding sequence according to the UCSC Known Genes track. Next, sequences that did not consist of at least 50% overlap with a CpG island were removed, and the remaining sequences were screened for <20% methylated reads through RBSS data. Finally, regions were screened for a verified CTCF binding site.

The ranking method was powered by data from a study identifying 1,522 housekeeping genes and their coefficient of variation across 42 tissues (19). Results from the computational algorithm were ranked first by their distance to the transcription start site of the nearest housekeeping gene, and then by the coefficient of variation of that gene.

The Broad peak data was downloaded from ENCODE for GM12878, which spanned 13 histone modifications and transcription factor binding sites: CTCF, EZH2, H2A.Z, H3K4m1, H3K4m2, H3K4m3, H3K9ac, H3K9m3, H3K27ac, H3K27m3, H3K36m3, H3K79m2, and H4K20m1. The files contain discrete intervals of ChIP-seq fragment enrichment through a statistical approach further described through the UCSC ENCODE portal, specifically using the Scripture software to call peaks (Guttman, M. et al. (2010) $Nat$ $Biotechnol$, 28, 503-510 (49)), followed by an unpublished Matlab script to decouple smaller enriched intervals within very large intervals from the Scripture output. The bedtools intersect function was used consecutively on each of the 11 ChIP-seq signals that were associated with the A2UCOE locus: H3K4m1, H3K4m2, H3K4m3, H3K9ac, H3K27ac, H3K36m3, H3K79m2, H4K20m1. ChIP-seq peaks for EZH2, H2A.Z, and CTCF were also used in this fashion. bedtools subtract was used to remove any intervals in the resulting dataset for H3K9m3 and H3K27m3.

The UCSC Known Genes Track was downloaded from the UCSC genome browser. This Known Genes dataset was constructed based on protein data from Swiss-Prot and associated mRNA data from Genbank (Hsu, F. et al. (2006) $Bioinformatics$, 22, 1036-1046 (50)). The known gene track was subtracted from the working candidate list (using bedtools subtract) and that result then intersected with the working list (keeping the entirety of the original interval using bedtools intersect with the –wa function) to remove any regions that were completely within the known gene track.

The CpG island track was downloaded from the UCSC Genome Browser, which was generated using a modified version of a program developed by G. Miklem and L. Hillier, and predicts CpG islands using three particular criteria: (1) GC content of 50% or greater, (2) 1 length greater than 200 bp, (3) ratio greater than 0.6 of observed number of CG dinucleotide to the expected number on the basis of the number of Gs and Cs in the segment. The program examines each base one at a time, scoring dinucleotides +17 for CG and −1 otherwise. This was intersected with the working list using bedtools intersect to find overlaps, and keep the entire original entry where there was a minimal overlap of 0.5 (50%).

DNA methylation data from Reduced Representation Bisulfite Sequencing (RRBS) in GM12878 was downloaded from ENCODE (Consortium, E. P. (2012) $Nature$, 489, 57-74 (51)). This data consisted of intervals identified through RBSS, read counts within each interval, and the percent methylated CGs for each interval. This list was filtered first to only include entries with at least 10 reads and then percent methylated (a) greater than 10%, (b) greater than 20%, and (c) less than 20%. Initially, the overlapSelect function from UCSC Genome Browser was to keep all candidates that overlapped with (a), but this criteria was too harsh as it removed the A2UCOE locus from the list. So instead the overlapSelect function from UCSC Genome Browser was used to keep all candidates that overlapped with (c) and remove any that overlapped with (b).

Finally, a simple overlapSelect was performed with the CTCF binding site data from ENCODE Transcription factor CHIP dataset, which encompasses data across several cell lines (Wang, J. et al. (2013) $Nucleic$ $Acids$ $Res$, 41, D171-176 (52)).

Re-ranking Candidate List by Housekeeping Gene Coefficient of Variance. A list of identified housekeeping genes and their coefficients of variance was obtained from a 2009 study of the gene expression profiles of 42 tissues (She, X. et al. (2009) $BMC$ $Genomics$, 10, 269 (53)). The accession numbers were mapped to RefSeq gene names and their corresponding chromosome number and position. This file and the identified candidate list were used as an input to the bedtools Closest function to determine the distance to and identity of the closest housekeeping gene for each candidate, including regions that overlapped with the housekeeping gene (HKG). Results were then merged back with the coefficient of variations from the housekeeping-identifying study (53). The result of this analysis was 88 regions of interest, which were then sorted by distance to housekeeping gene and then further sorted by the coefficients of variance to rank-order the candidate list. This ranking resulted in A2UCOE being at the top of the list (zeroth position), and candidates were named Candidate 1, 2, and onwards to result in a total of 87 putative UCOE candidates. Rankings for A2UCOE and Candidates 1-20 are shown in FIG. 1A.

B. Construction of Vectors

Actual candidate sequence was determined by a visual inspection of the outputs of the algorithm using the February 2009 GRCh37/hg19 assembly in the UCSC Genome Browser (20). Start and end positions were visually determined for the candidates based on including as many desired features from the computational search as possible (e.g., the entirety of a CpG island, or to include any nearby CTCF binding sites) to result in a 1-1.5 kb length (see Table 1 below). Strand refers to +/− strand of the genome, as all candidates were drawn to be in the same 5'>3' direction as the gene with the nearest TSS to the candidate region. Regions between divergently transcribed genes are noted as divergent, along with name of the reverse complement.

TABLE 1

Position of algorithm output candidates versus experimental candidates in the
GRCh37/hg19 human genome assembly

| Candidate # | Chromosome | Algorithm start | Algorithm End | Candidate Start | Candidate End | Strand | Length | Divergent? |
|---|---|---|---|---|---|---|---|---|
| 1 | chr6 | 160210822 | 160212252 | 160210497 | 160211870 | + | 1374 | yes, 1R |
| 2 | chr1 | 245027688 | 245027958 | 245027171 | 245028685 | – | 1383 | no |
| 3 | chr6 | 1601147650 | 160148658 | 160147398 | 160148705 | + | 1308 | no |
| 4 | chr16 | 25122572 | 25123049 | 25122235 | 25123617 | + | 1383 | no |
| 5 | chr20 | 5093492 | 5094272 | 5093242 | 5095057 | – | 1816 | no |
| 6 | chr9 | 136223261 | 136223954 | 136222946 | 136223954 | + | 1009* | yes |
| 7 | chr1 | 226595430 | 226596263 | 226594104 | 226596047 | + | 1944 | no |
| 8 | chr17 | 66507666 | 66508098 | 66507371 | 66509135 | + | 1765 | no |
| 9 | chr15 | 44828479 | 44829488 | 44828051 | 44829:357 | + | 1307 | yes, 9R |
| 10 | chr10 | 1051156061 | 105156603 | 105155621 | 105157125 | – | 1505 | yes, 10R |

Primers were designed using NCBI Primer-Blast. These
are listed below in Table 2.

TABLE 2

Primers

| Name | SEQ ID NO | DNA Sequence |
|---|---|---|
| Can1_fwd_SalI | 10 | actaagaGTCGACCCATCTTGACGGCAGCGATA |
| Can1_rev_NheI | 11 | tagttctGCTAGCCGCTGAGACGATCTCGGAAA |
| Can1R_fwd_SalI | 12 | actaagaGTCGACCGCTGAGACGATCTCGGAAA |
| Can1R_rev_NheI | 13 | tagttctGCTAGCCCATCTTGACGGCAGCGATA |
| Can2_fwd_SalI | 14 | actaagaGTCGACTCACCCTCACGGTTAGCTACT |
| Can2_rev_NheI | 15 | tagttctGCTAGCCAACGTACAACGCAGCACTC |
| Can3_fwd_SalI | 16 | actaagaGTCGACCAGACCGATCTGATTCACTGG |
| Can3_rev_NheI | 40 | tagttctGCTAGCCGGTCGCATAGGCCGAG |
| Can4_fwd_SalI | 17 | actaagaGTCGACACTTTTCCACACACTACTTCCCTC |
| Can4_rev_NheI | 18 | tagttctGCTAGCTCTGTCTTTCCAGCAGCGTT |
| Can6_fwd_SalI | 19 | actaagaGTCGACGCACACGACCACAATTCCAC |
| Can6_rev_NheI | 20 | tagactGCTAGCGACCACCTACGGGTTCTTGG |
| Can6R_fwd_SalI | 21 | actaagaGTCGACGACCACCTACGGGTTCTTGG |
| Can6_rev_NheI | 22 | tagttctGCTAGCGCACACGACCACAATTCCAC |
| Can8_fwd_SalI | 23 | actaagaGTCGACAAGCACACGGCCCTAGAAAT |
| Can8_rev_NheI | 24 | tagttctGCTAGCTGGAGAGGAAAACTACCGGC |
| Can9_fwd_SalI | 25 | actaagaGTCGACGTCCTGCCCACGTATCTACC |
| Can9_rev_NheI | 26 | tagttctGCTAGCCTAGCGAGGAGTTAGCACGG |
| Can9R_fwd_SalI | 27 | actaagaGTCGACCTAGCGAGGAGTTAGCACGG |
| Can9R_rev_NheI | 28 | tagttctGCTAGCGTCCTGCCCACGTATCTACC |
| Can5_fwd_SalI | 29 | actaagaGTCGACCAAGTTCACTGTGTGCTGTGTATT |
| Can5_rev_NheI | 30 | tagttctGCTAGCGTCTTCGTTGCCAACAGGCT |
| Can7_fwd_SalI | 31 | actaagaGTCGACGAGGGGTTGGGGGTAAAATTAGT |
| Can7_rev_NheI | 32 | tagttctGCTAGC AGGTTCCTTAGTGGGCAACA |
| Can10_fwd_SalI | 33 | actaagaGTCGAC AGCAGGGAAAGCGAGAGAAC |
| Can10_rev_NheI | 34 | tagttctGCTAGC AAAGGCCTTCCCACTGATCG |

TABLE 2-continued

Primers

| Name | SEQ ID NO | DNA Sequence |
|------|-----------|--------------|
| Can10R_fwd_SalI | 35 | actaagaGTCGAC AAAGGCCTTCCCACTCTATCG |
| Can10R_rev_NheI | 36 | tagttctGCTAGC AGCAGGGAAAGCGAGAGAAC |
| Can6_213F_fwd (for 6-1) | 37 | actaagaGTCGAC TTCAAAGTGCAGGGCAGACA |
| Can6_585F_fwd (for 6-2) | 38 | actaagaGTCGAC TTCTGCGAGCGGCTTCC |
| Can6_874R_rev (for 6-3) | 39 | tagttctGCTAGC TTCCCTCTCCTCCCCTGATC |

Candidate clones were obtained by PCR using human bone osteosarcoma cell line U2OS genome preparations as template with the Kapa Hifi Hotstart Polymerase (Roche) according to manufacturer's instructions. The primary stable transfection plasmid pCS4255 was created through the addition of the back-to-back Ef1α-EGFP, hPGK-PuroR cassette using the SalI/BglII sites in the ROSA26 donor plasmid, a gift from Charles Gersbach (Addgene plasmid #37200). Positive controls (i.e., 2.2 kb A2UCOE and 1.2 kb 3'UCOE elements) and putative UCOEs were cloned through ligation cloning into the SalI/NheI restriction enzyme sites in pCS4255. The plasmids used in this study are listed below in Table 3.

TABLE 3

Plasmids

| Plasmid # | Description | Source/Parent |
|-----------|-------------|---------------|
| | Stable Transfection (Screen) Plasmids | |
| pCS3207 | pDonor for ROSA26 | Gersbach lab, Addgene #37200 |
| pCS4255 | Ef1α-EGFP | pCS3207 |
| pCS4256 | A2UCOE-Ef1α-EGFP | pCS4255 |
| pCS4257 | 3'UCOE-Ef1α-EGFP | pCS4255 |
| pCS4258 | Candidate1-Ef1α-EGFP | pCS4257 |
| pCS4259 | Candidate1R-Ef1α-EGFP | pCS4257 |
| pCS4260 | Can3-Ef1α-EGFP | pCS4257 |
| pCS4261 | Can6-Ef1α-EGFP | pCS4257 |
| pCS4262 | Can6(opp)-Ef1α-EGFP | pCS4257 |
| pCS4263 | Can8-Ef1α-EGFP | pCS4257 |
| pCS4264 | Can9R-Ef1α-EGFP | pCS4257 |
| pCS4265 | A2UCOE-EGFP | pCS4255 |
| pCS4266 | 3'UCOE-EGFP | pCS4255 |
| pCS4267 | Can1-EGFP | pCS4266 |
| pCS4268 | Can1(opp)-EGFP | pCS4266 |
| pCS4269 | Can3-EGFP | pCS4266 |
| pCS4270 | Can6-EGFP | pCS4266 |
| pCS4271 | Can6(opp)-EGFP | pCS4266 |
| pCS4272 | Can5-Ef1α-EGFP | pCS4266 |
| pCS4273 | Can7-Ef1α-EGFP | pCS4266 |
| pCS4274 | Can10-Ef1α-EGFP | pCS4266 |
| pCS4275 | Can10R-Ef1α-EGFP | pCS4266 |
| | Lenti plasmids | |
| pCS3799 | pLenti donor | Xiang et al. (64) |
| pCS3800 | pMO86 HIV-1 Gag packaging plasmid | Xiang et al. (64) |
| pCS3801 | pMO87 VSV g envelope protein plasmid | Xiang et al. (64) |
| pCS4276 | pKL5-with Ef1α-EGFP | pCS3799 |
| pCS4277 | pKL5-with Can6-Ef1α-EGFP | pCS3799 |
| pCS4278 | pKL5 with Can12R-Ef1α-EGFP | pCS3799 |
| pCS4279 | pKL5 with A2UCOE-Ef1α-EGFP | pCS3799 |
| pCS4280 | pKL5 with 3'UCOE-Ef1α-EGFP | pCS3799 |
| pCS4281 | Can6-1-Ef1α-EGFP | pCS4278 |

TABLE 3-continued

Plasmids

| Plasmid # | Description | Source/Parent |
|-----------|-------------|---------------|
| pCS4282 | Can6-2-Ef1α-EGFP | pCS4278 |
| pCS4283 | 6-3-Ef1α-EGFP | pCS4278 |
| pCS4284 | pKL5 with CMV-EGFP | pCS3799 |
| pCS4285 | Can6-1-CMV-EGFP | pCS4284 |
| pCS4286 | Can6-2-CMV-EGFP | pCS4284 |
| pCS4287 | A2UCOE-CMV-EGFP | pCS4284 |
| pCS4288 | 3'UCOE-CMV-EGFP | pCS4284 |
| pCS4289 | Can6-CMV-EGFP | pCS4284 |
| pCS4290 | Can 6-3-CMV | pCS4284 |
| pCS4291 | pKL5 with PGK-EGFP | pCS3799 |
| pCS4292 | Can6-1-PGK-EGFP | pCS4291 |
| pCS4293 | Can6-2-PGK-EGFP | pCS4291 |
| pCS4294 | A2UCOE-PGK-EGFP | pCS4291 |
| pCS4295 | 3'UCOE-PGK-EGFP | pCS4291 |
| pCS4296 | Can6-PGK-EGFP | pCS4291 |
| pCS4297 | Can 6-3-PGK | pCS4292 |
| pCS4298 | RSV-EGFP | pCS4291 |
| pCS4299 | Can6-1-RSV-EGFP | pCS4298 |
| pCS4300 | 3'UCOE-RSV-EGFP | pCS4295 |
| pCS4301 | Can6-RSV-EGFP | pCS4296 |
| pCS4302 | A2UCOE-RSV-EGFP | pCS4294 |
| pCS4303 | Can6-2-RSV-EGFP | pCS4298 |
| pCS4304 | Can 6-3-RSV-EGFP | pCS4303 |

Lentiviral vectors were based on the donor plasmid pCS3799. The UCOE-Ef1α-EGFP cassette from the stable transfection plasmids was cloned into the Xma1/Xba1 sites in pCS3799 to make pCS4276. Additional truncation candidates were cloned into the Sal1/Nhe1 sites preceding the Ef1α promoter (SEQ ID NO:6). The three other promoters—CMV, PGK, and RSV (SEQ ID NOs: 7-9)—were cloned using the Sal1/Age1 sites in pCS4276. UCOE candidate sequences were cloned through the Sal1/Nhe1 sites in these plasmids.

C. Maintenance of P19 Cell Lines

Mouse embryonic teratocarcinoma stem P19 cells were obtained from ATCC (CRL-1825) and maintained in alphaMem medium with Glutamax™ medium supplement (Thermo Fisher Scientific) and 10% FBS (Thermo Fisher Scientific). Cells that were FACS sorted were maintained in this growth media with the addition of 1% penicillin/ streptomycin (Thermo Fisher Scientific). HEK293T (ATCC CRL-3216) cells for lentiviral production were cultured in DMEM media (Thermo Fisher Scientific) with 10% FBS (Thermo Fisher Scientific). All cells were grown at 37° C., 5% $CO_2$, and 80% humidity in an incubator.

D. Stable Transfection of P19 Cell Line

P19 cells were seeded at 25,000 cells/well in 12 well plates. 24 h after seeding, cells were transfected using Lipofectamine™ 2000 transfection reagent (Thermo Fisher) according to the manufacturer's instructions using 500 ng DNA/well and 2.5 µL of Lipofectamine per well. 24 hours after transfection, selection was initiated with 1 µg/mL puromycin (Sigma-Aldrich) in regular growth media and, from then on, cells were passaged at 1:15 or 1:20 dilutions whenever cells were 80-90% confluent (every 2-3 days) with frequent refreshing of puromycin-containing media to clear dead cells. After approximately 14-16 days, remaining cells were assumed to be stably transfected and were changed to regular growth media to initiate silencing experiments. During silencing experiments, the P19 cells were passaged every 2-3 days and re-seeded at 15,000 cells/well.

E. Lentiviral Preparation & Transduction of P19 Cell Line

Two plasmids (pCS3800: encoding HIV-1 Gag; pCS380: encoding VSVg envelope protein) were used with varying versions of the donor plasmid pCS3799. HEK293T cells were plated at 5×10^6 cells in a 10 cm dish. Twenty-four hours after plating, the three plasmids (10 µg donor, 8 µg pCS3800, 10 µg pCS3801) were co-transfected together using a calcium phosphate protocol (Zufferey, R. T. and Trono, D. (2001) *Current Protocols in Human Genetics, 26* (1), 12.10.1-12.10.12; DOI: 10.1002/0471142905.hg1210s26 (55)). The total DNA was brought to 500 µL in water, to which 500 µL of 2×HEPES-buffered saline, pH7.0 (Alfa Aesar) was added and mixed. One-tenth of the total volume (100 µL) of 2.5 M calcium chloride (Sigma-Aldrich) was then added to the mixture, followed by a 20-minute incubation. The mixture was then added to the plate in a dropwise manner. Media was replaced six hours later, and the supernatant was collected at 48 hr after the transfection, filtered through 0.4 µm filter, and frozen at −80° C. in 1 mL aliquots. Lentiviral aliquots were thawed in a 37° C. bead bath before transductions.

P19 cells were plated at 20-30,000 cells/well in 12-well plates one day before transduction. Twenty-four hours after plating, cells were transduced at varying dilutions of the lentiviral stock (ranging from 1:2 to 1:100) in DMEM+10% FBS with 8 µg/mL polybrene (Santa Cruz Biotechnologies). Media was refreshed on P19 cells 24 hours after transduction, and cells were passaged and assayed through a MACSQuant® VYB flow cytometer (Miltenyi Biotec) 48 h after transduction. MOI was determined by reporter expression at this timepoint using the following formula: $MOI = ln(1/1-p)$ where p is the % of cells that are GFP positive at 48 hours post-transduction (Chen, S. et al. (2015) *Cell,* 160, 1246-1260 (56)).

Only populations that resulted in MOIs between 0.15 and 0.5 were subject to FACS sorting 5 days post transduction. Cells were FACS-sorted on the BD Influx™ cell sorter at the Stanford FACS Facility using the 488-nm laser and 525/40 filter to assay GFP expression. After gating for singlets and viability, GFP+ gate was drawn to be <0.1% GFP positive in non-transduced P19 cells. GFP+ gates were re-drawn for each promoter set to avoid the ~10% highest and lowest expressing cells within the GFP+ gate, but the same gate was used for every experimental condition under the same promoter. Triplicate wells of each population (12-15,000 cells/well in a 24-well plate) were collected.

F. Epigenetic Effector Experiments

Replica-plated cell populations were treated with varying concentrations of 5-aza-2'-deoxycytidine (Sigma-Aldrich, A3656) or Trichostatin A (Sigma-Aldrich, T1952) 24 hours after passaging. TSA was purchased as a readymade 5 mM solution in DMSO, which was then diluted to a 0.05 µM or 0.1 µM concentration in P19 growth media. 5 mg of 5-aza-2'-deoxycytidine was dissolved in 1 mL of 1:1 acetic acid:

water to make a 21.9 mM stock solution, which was then diluted in P19 growth media to 2 µM or 10 µM. Cells were assayed through flow cytometry after 24 hours.

G. Flow Cytometry Analysis

Fluorescence data throughout silencing experiments was obtained using a MACSQuant® VYB flow cytometer (Miltenyi Biotec). EGFP was measured through the 488-nm laser and 525/50 nm band pass filter. Flow cytometry data was analyzed using the FlowJo™ single cell flow cytometry analysis software (Tree Star). After being gated for singlets and viability, GFP+ gates in FlowJo were drawn such that a non-transfected or non-transduced P19 cell population was at 1% GFP+. Median values reported are of cells within the GFP+ gate, both % GFP positive and median are reported with the standard deviation of biological replicates.

Example 2: Computational Algorithm Returns 87 Candidate UCOE Sequences

Figure 1B:
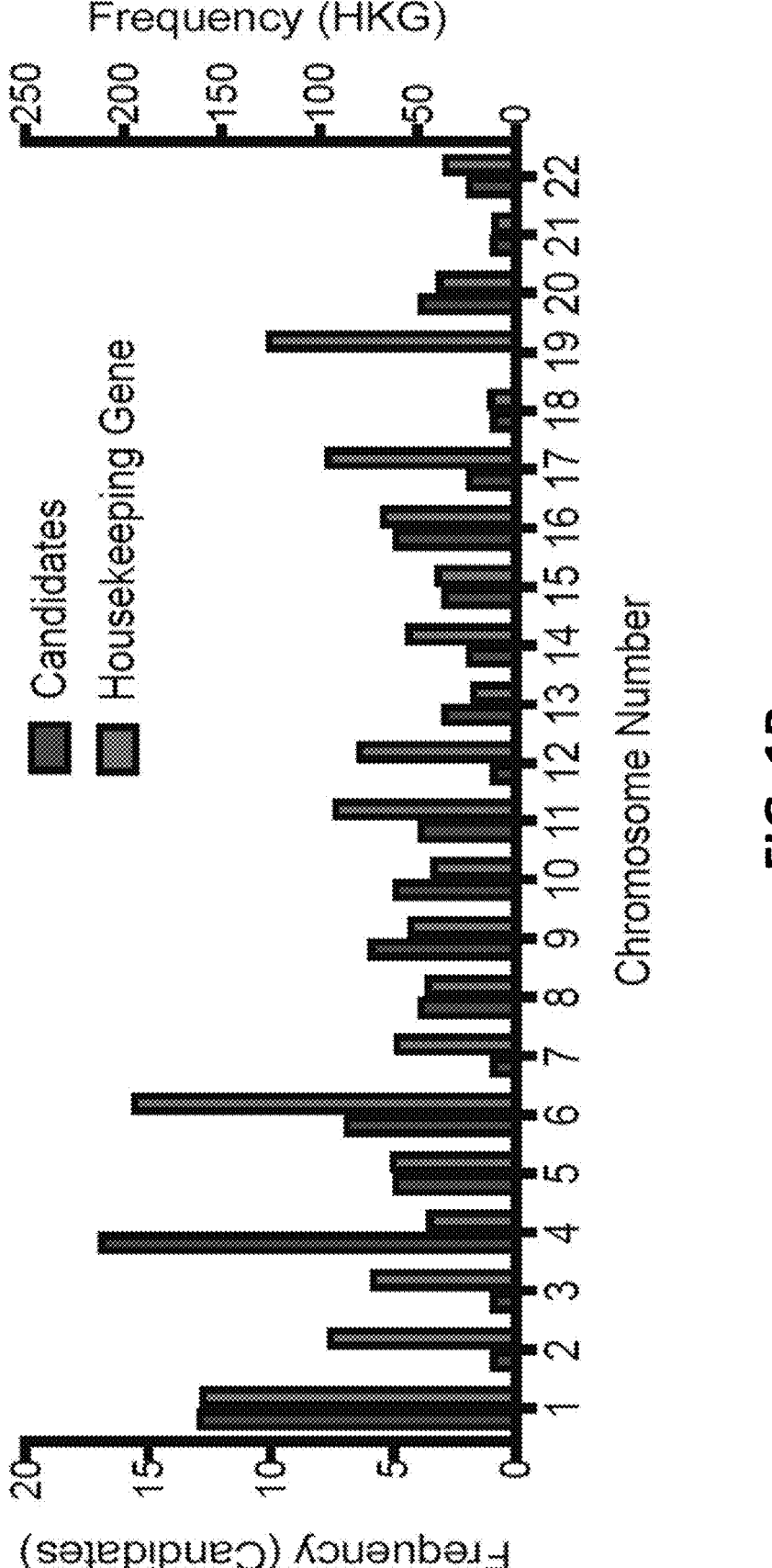
FIG. 1B shows the distribution of the candidates regions across 22 autosomal chromosomes as compared to that of known housekeeping genes according to aspects of this disclosure.

To better prioritize the resulting candidate UCOEs for experimental characterization, a ranking methodology was implemented based on the hypothesis that the best UCOEs would be co-localized with the strongest housekeeping genes. As described above, a study of the human genome was used that identified 1,522 housekeeping genes using the gene expression profiles of 42 tissues (She, X. et al. (2009) *BMC Genomics,* 10, 269 (19)). Elements were ranked first on the distance to the nearest housekeeping gene and then by the coefficient of variance (lowest to highest) of that housekeeping gene as a measure of how consistently that gene is expressed (according to (19)). As a validation of this approach, the region encompassing the A2UCOE locus came out first with this methodology, leaving 87 other ranked candidate regions to test for UCOE activity, with sizes ranging from 57 to 3916 bp (A2UCOE and candidates 1-20 are shown in FIG. 1A). As many of the criteria used are broadly associated with regulatory regions of housekeeping genes, the distribution of the candidates across 22 autosomes was compared to the distribution of known housekeeping genes as shown in FIG. 1B. The results from this analysis show that the distributions are not correlated. For example, there are no candidates on chromosome 19 even though it has the third-most housekeeping genes, and chromosome 4 is overrepresented in the candidate UCOE regions compared to the distribution of housekeeping genes. The difference in distributions suggests that the algorithm searches for something distinct than a subsection of housekeeping regulatory areas and supports the utility of the algorithm developed as described herein.

The first ten candidate regions were visually inspected in the UCSC Genome Browser (20) in the hg19 assembly to draw candidate element boundaries such that the size of all tested candidates was between 1-1.5 kb (see Table 1 above). Boundaries were drawn to most conservatively include all nearby CTCF sites and the entirety of the CpG island when possible. Candidate regions were oriented in the same 5' to 3' direction as the nearest gene. In areas between dual divergent genes (i.e. Candidates 1, 6, 9, and 10), candidates were tested in both configurations with the (−) strand designated as "R".

Example 3: Candidate UCOEs Exhibit Activity in a P19 Embryonal Carcinoma Stem Cell Silencing Screen Candidates were initially screened in the P19 murine embryonic carcinoma stem cell line. Murine embryonic carcinoma P19 cells are commonly used to study transgene silencing as they are susceptible to silencing within 2-3 weeks while other cell lines can take months. Early studies and characterization of A2UCOE in P19 cells (Zhang, F. et al. (2010) *Mol Ther,* 18, 1640-1649 (7); Knight, S. et al. (2012) *J Virol,* 86, 9088-9095 (22)) support that it is a valid model system for studying anti-silencing activity that is predictive of efficacy in other cells and in vivo. As P19 cells readily integrate DNA, a stable transfection of the expression construct performed. The EF1α (Elongation Factor 1) promoter was selected as the promoter to be linked with the candidate UCOEs because of its non-viral origin, so as to disregard the effect of viral recognition silencing (Gill, D. R et al. (2001) *Gene Therapy,* 8, 1539-1546 (57)), and its high expression level may allow for better dynamics in identifying the best performing candidates. Because stable transfections have a low efficiency of integration, a selection cassette was incorporated into the construct. Another endogenous non-viral promoter, the hPGK promoter, was chosen to drive expression of the puromycin resistance gene. The Ef1α-GFP and hPGK-PuroR cassettes were designed to be oriented in opposing directions with the polyA terminators back-to-back, for maximal separation between the two promoters as shown in FIG. 2A. This design was intended to reduce polymerase run-through from one cassette to the other, as well as maintain genetic distance so that the epigenetic mechanism might be able to act independently on each promoter.

Figure 2D:
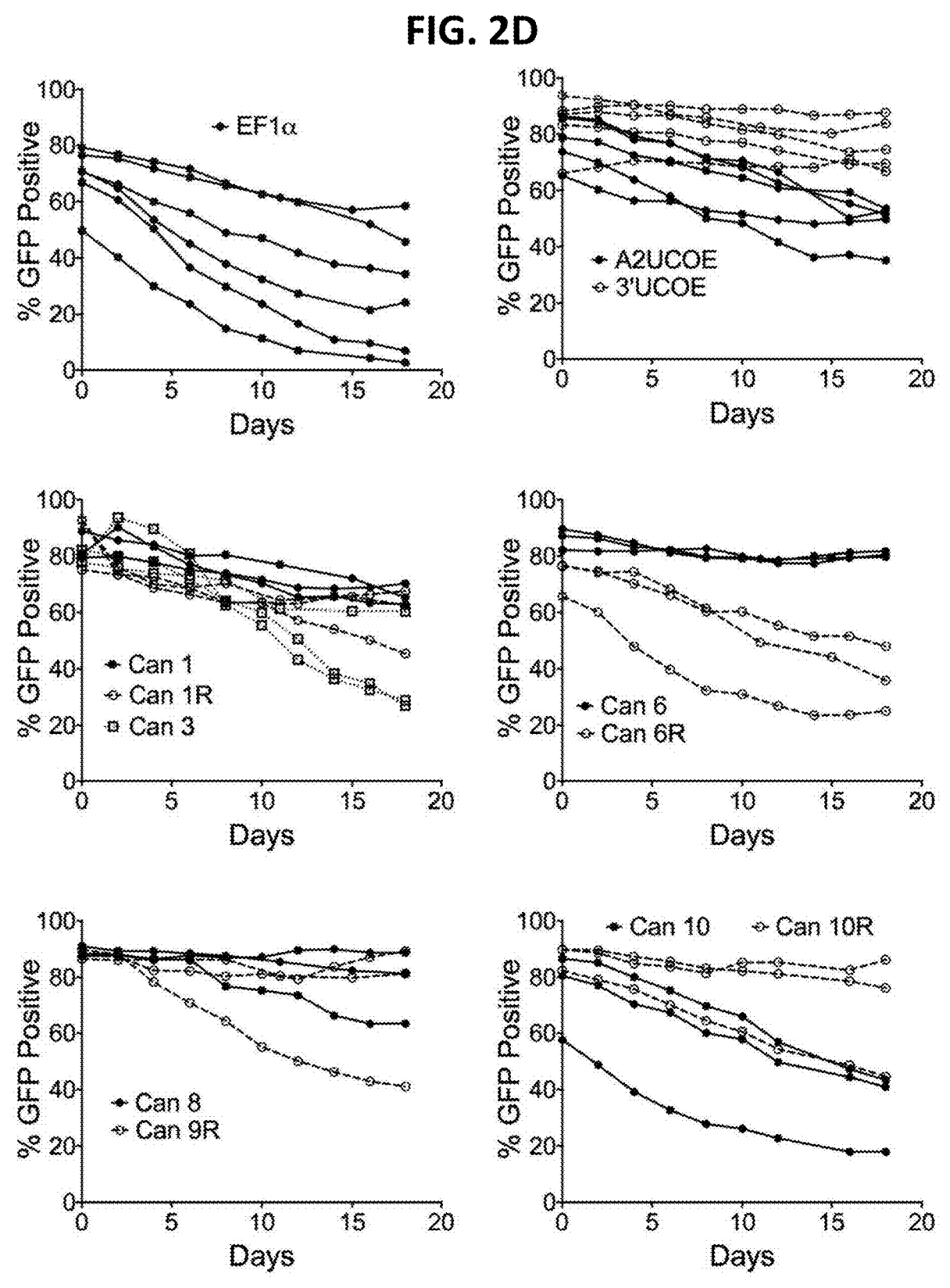
Figure 2E:
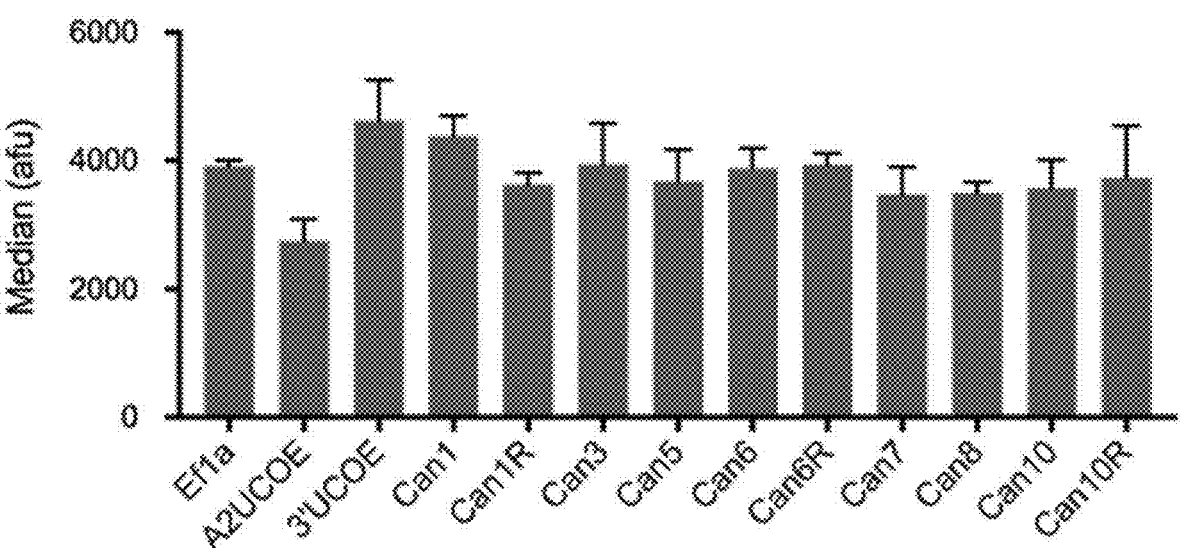
FIG. 2E shows the median GFP expression values (in arbitrary fluorescence units (afu)) for candidate UCOEs and controls at day 0 (top) and day 19 (bottom) in the P19 stable transfection screen as described for FIG. 2B and FIG. 2D according to aspects of this disclosure. The data shows that median GFP values for positive controls and tested candidates are not significantly different from the negative (Ef1a promoter only) control at day 0 (by one-way ANOVA). The unsubstantial differences in median expression demonstrates that the % GFP+ cells in the population is a more meaningful measure of silencing. Data is reported as the mean±SD from at least three biological replicates.
Figure 2E:
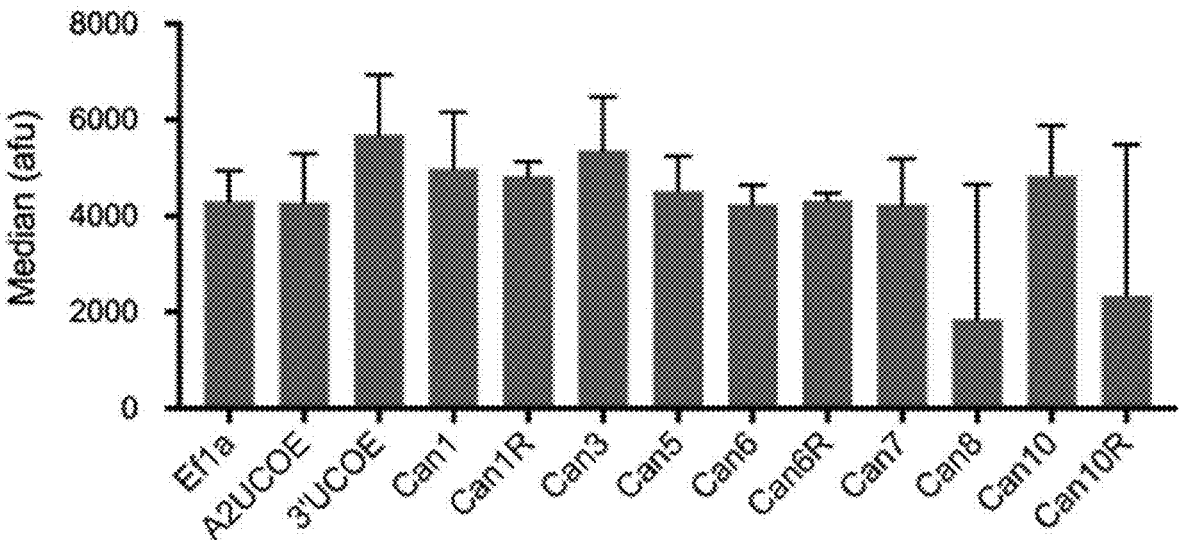

Candidate UCOEs were cloned directly upstream of the Ef1α-EGFP cassette after PCR from a genome prep of the U2OS human osteosarcoma cell line. Candidates 2 and 4 were not recoverable with PCR As a positive control, the 2.2 kB A2UCOE sequence, as well as the 1.2 kB reverse orientation sequence 3'UCOE, were cloned into the same reporter construct as the candidate sequences. All candidate constructs and controls were transfected into P19 cells and selected for stable integrants by passaging in antibiotic-selective media over two weeks. After two weeks of selection, cells were transferred into antibiotic-free media to relieve the selection pressure that would counteract gene silencing. Cells were passaged every 2-3 days and the percent GFP positive in the population was monitored as a metric for silencing by flow cytometry analysis with each passage. The results as shown in FIG. 2D demonstrate an exponential decay in this metric over the course of 19 days, with the negative (no-insulator control) having the most drastic decay over the first five days while active insulators resulted in more consistent gene expression over time. As shown in FIG. 2B, analysis of the loss of GFP-positive cells over time showed that both A2UCOE and 3'UCOE conferred silencing resistance compared to the negative (Ef1α-only) control, with the 1.2 kB 3' UCOE mediating only an 8% loss in percent GFP positive cells over the time period, compared to 40% for the negative control and 29% for the 2.2 kb A2UCOE sequence. Additionally, four of the eleven tested candidates, Candidates 1, 5, 6 and 8, showed a significant improvement in stable expression relative to the negative control. In particular, Candidate 6 conferred the least loss of expression at about 6% loss over the 19 days, although the reverse orientation of Candidate 6 conferred no protective effect. Replicates were so variable for Candidate 9R and 10R that it was not possible to conclude that they outperformed the control. In particular, candidate 6 conferred the least loss of expression, while the reverse orientation did not outperform the negative control. Absolute expression, measured by GFP intensity, was not significantly different across cell populations harboring different controls and candidate UCOEs, as shown in FIG. 2E, confirming gene silencing as an all-or-nothing per-cell phenomenon.

As A2UOCE dually functions as a protective regulatory element and a universal promoter, the candidate UCOEs were further screened for standalone promoter activity. A similar experiment as the aforementioned screen was performed using a similar expression construct that lacked the Ef1a promoter. A schematic representation of such constructs is shown in FIG. 2C (inlay). This construct was used to assess whether the candidate sequences could drive reporter expression and act as stand-alone functional promoters. Candidates were compared to the positive control of the EF1a promoter, which had ~70% GFP+ cells after two weeks of antibiotic selection, showing a distinct positive population in the fluorescence histogram. The GFP+ gate (i.e., flow cytometry fluorescence threshold for GFP+ cells) was set to encompass 1% of untransfected cells and then applied to all samples. In a representative flow cytometry example, positive control cells (Ef1a promoter) showed 74.2% GFP+ cells after two weeks of antibiotic selection. Such a result appears as a bimodal distribution on a histogram, with a peak below the gate threshold (i.e., GFP negative cell population) and a peak above it (i.e., the distinct GFP positive population mentioned above). A representative example for seven of the tested constructs shown in FIG. 2C showed the following percentages of GFP+ cells: A2UCOE: 77.5% GFP+; 3'UCOE: 75.5% GFP+; Can5: 18.9% GFP+; Can6: 1.99% GFP+; Can6R 0.93% GFP+; Can10: 58.4% GFP+; Can10R: 61.6% GFP+ (data not shown). In this study, a % GFP+ of at least 50% is considered to reflect the existence of a second population in the histograms, and thus a binary indicator of promoter function. Accordingly, histograms for the constructs showing at least 50% GFP+ cells (A2UCOE, 3'UCOE, Can10, and Can10R) all show two distinct peaks, while only one peak is visible for the constructs showing less than 50% GFP+ cells (Can5, Can6, and Can6R). The median GFP intensity of the GFP+ population was used a measure of the strength of the promoter, and normalized to the Ef1a positive control as shown in FIG. 2C.

Figure 3A:
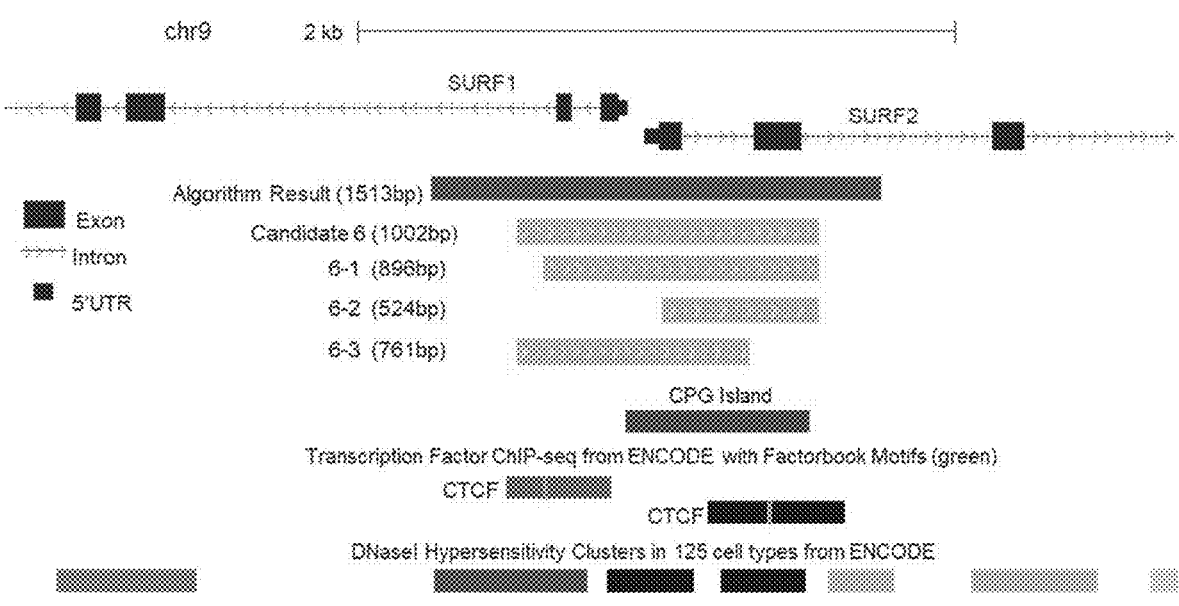
FIG. 3A shows a schematic representation of the genomic region that includes the candidate 6 SRF-UCOE region and truncation constructs 6-1, 6-2, and 6-3 thereof according to aspects of this disclosure. Boundaries for the 1,003 bp Candidate 6 were drawn to include the entire region between SURF1 and SURF2 and the first introns of both genes including the entirety of the CpG island and CTCF sites. Construct 6-1 includes a small 5' deletion but retains the most 3' exon of SURF1 and all identified features of the locus. Construct 6-2 includes a larger 5' deletion in which all SURF1 sequences and the 5' UTR of SURF2 are deleted such that it lacks the first CTCF binding site and excludes the intergenic region between SURF1 and SURF2. Construct 6-3 includes a 3' deletion in which the second exon of SURF2 and the second CTCF site are excluded. The locations of the CpG island, CRCF regions, and DNaseI hypersensitivity clusters within this genomic region are also shown schematically.

As expected, A2UCOE and 3'UCOE both exhibit promoter activity, with A2UCOE driving more than twice the absolute expression of GFP as 3'UCOE as shown in FIG. 2C. This aligns with previous observations that the RNPA2B1 promoter is much stronger than that of CBX3 (Zhang, F., et al. (2010) *Mol Ther,* 18, 1640-1649 (7)). However, the RNPA2B1 promoter in A2UCOE is only 30% as strong as the EF1α promoter. Several of the candidate UCOEs tested, including Candidates 3, 10 and 10R, are promoters comparable to 3'UCOE with absolute expression of about 10% of EF1α. On the other hand, Candidate 6 (SRF-UCOE) and 6R did not exhibit inherent promoter activity, having expression at the level of background noise at 1-3% GFP+ as shown in FIG. 2C. Candidate 6 encompasses the entire regulatory region between the transcription start sites of the divergent genes SURF1 and SURF2, as well as the first exon and intron of each gene, as shown in FIG. 3A. Therefore, this region must encompass the endogenous promoters for SURF1 and SURF2. However, in this synthetic test construct, the promoters are non-functional, suggesting that the promoter activity is dependent on an enhancer sequence that might be quite distant in two dimensional sequence space but topologically close in three dimensional space. Because of the nonmodularity and potential safety concerns associated with A2UCOE's bidirectional promoter activity, Candidate 6 may present advantages in particular applications by not exhibiting promoter activity.

Figure 3B:
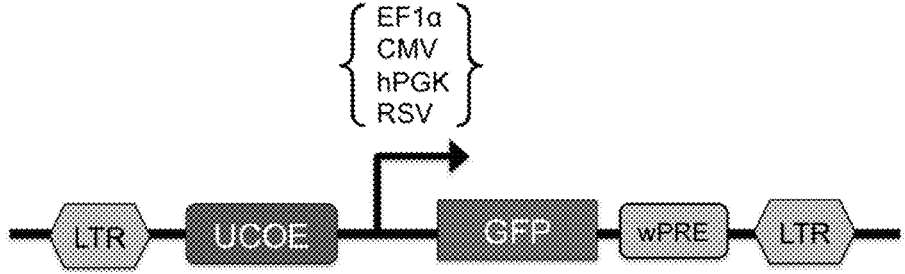
FIG. 3B shows a schematic illustrating lentivirus donor constructs used to assess Candidate 6 SRF-UCOE and truncation constructs for anti-silencing activity in stable transductions according to aspects of this disclosure. The expression construct includes one of four common promoters between the UCOE region and the GFP coding sequence. Long terminal repeats (LTR) flank the expression region. A Woodchuck Hepatitis Virus (WHP) Posttranscriptional Regulatory Element (wPRE) is located between the GFP coding sequence and the downstream LTR. The test promoters are CMV, EF1α, RSV, and PGK.

Example 4: Candidate 6 (SRF-UCOE) and Associated Truncations Demonstrate Activity Across Multiple Promoters While convenient for a screen, the stable transfection methodology is uncontrolled for copy number and integration sites are likely biased by antibiotic selection. Thus, the more reproducible and applicable integration technology of lentiviral transduction was chosen to further characterize the most active candidate UCOE element Candidate 6 (SRF-UCOE). A series of lentiviral constructs were constructed that associated candidate UCOE regions with four commonly used mammalian promoters. A schematic of such constructs is shown in FIG. 3B. Candidate 6 (SRF-UCOE) spans the entire region between SURF1 and SURF2 as well as the first introns of both genes, as shown in FIG. 3A.

In an effort to identify the core functional region of Candidate 6 (SRF-UCOE) and determine shorter sequences that exhibit this activity, three truncated versions of Candidate 6 (SRF-UCOE) were constructed and tested in this assay: construct 6-1, construct 6-2, and construct 6-3, as shown in FIG. 3A and FIG. 7. Truncation 6-1 was designed to keep as many of the important features as possible while removing additional spacer sequence; thus, the 5' end of the Candidate 6 region was truncated up to the first CTCF binding site and the CpG island was kept completely intact. Truncation 6-2 was designed to incorporate a larger truncation of the 5' end of the element to remove the intergenic region between SURF 1 and SURF2 and the first CTCF binding site while still incorporating the majority of the CpG island. Truncation 6-3 was truncated at the 3' end of the element thereby removing the second CTCF binding site. It was hypothesized that construct 6-1 would function as well as Candidate 6 (SRF-UCOE) due to retaining most of the predicted functional features. It was also hypothesized that the constructs 6-2 and 6-3 would exhibit reduced efficacy due to the loss of a CTCF binding site. Of particular interest was whether construct 6-2, which lacked the intergenic regulatory area between the divergent SURF1 and SURF2 genes would retain anti-silencing activity.

Figure 4A:
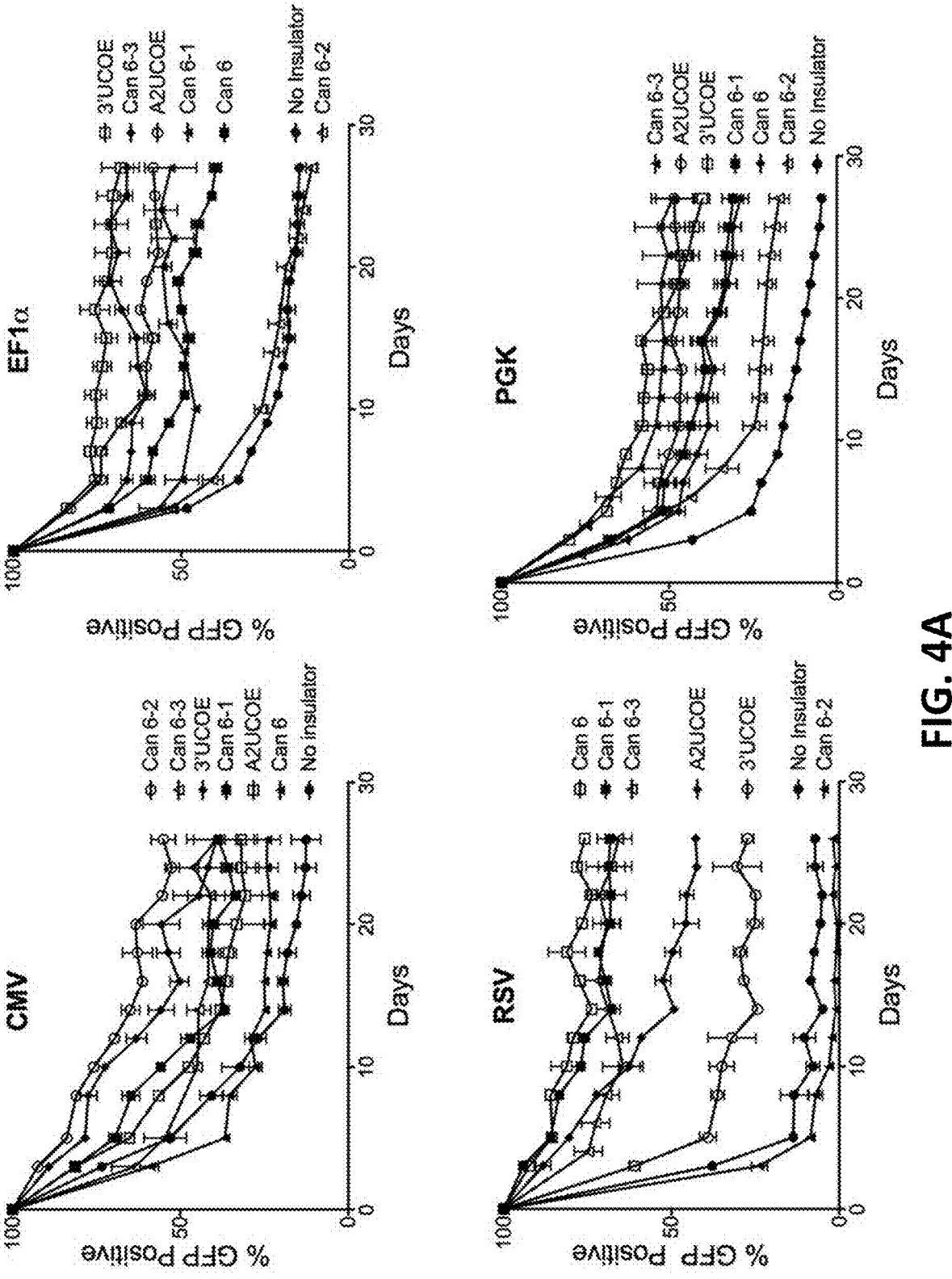
FIG. 4A shows the effect on silencing of the candidate 6 region and constructs 6-1, 6-2, and 6-3 over time in the lentiviral expression system using the CMV, EF1α, RSV, and PGK promoters according to aspects of this disclosure. The graphs show the raw data of measured percent GFP positive cells (% GFP+) for each construct over time. Transduced populations were sorted into triplicate wells using FACS at day 0 (5 days after lentiviral transductions) to begin the study at 100% GFP positive cells. Expression is lost quickly within the first 10 days, and then stabilizes around day 15. Data is reported as mean±SD from biological triplicates. Two positive UCOE controls (A2UCOE, 3'UCOE) and a negative control (no insulator region) were used. Day 26 data is shown in FIG. 4B.
Figure 4B:
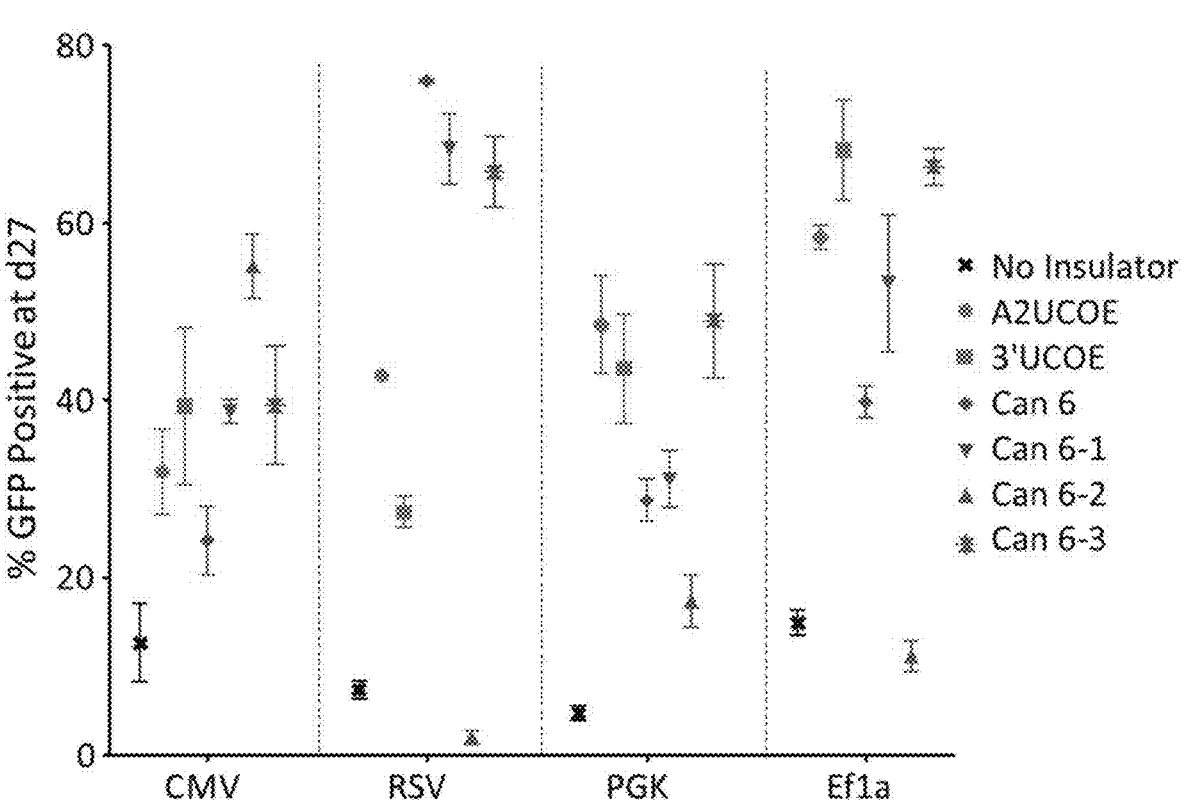
FIG. 4B shows that Candidate 6 SRF-UCOE and truncation constructs 6-1, 6-2, and 6-3 resist transgene silencing from lentiviral transductions with promoters CMV, EF1α, RSV, and PGK according to aspects of this disclosure. Percent GFP positive cells at the final timepoint (day 26 for CMV and RSV, day 27 for PGK and EF1α) of the lentivirus silencing experiment across the four tested promoters is plotted. P19 cells were FACS-sorted five days after transduction (day 0) and then assayed over a 26 or 27-day time period thereafter. Data is reported as mean±SD from three biological replicates.

P19 cells were transduced with lentiviral constructs harboring the four Candidate 6 regions, two positive UCOE controls (A2UCOE, 3'UCOE), and a negative control (no insulator region). Transduced cells were FACS-sorted after lentiviral integration at a low MOI to ensure single integrants. The initial MOI based on transduction efficiency (as described above) for all data shown in FIGS. 4A-4B is shown in Table 4 below. Each set of candidates and controls are shown in order of efficacy in resisting silencing (highest to lowest % GFP+ at day 26 or day 27). The percent GFP positive cells were assayed over time as with the stable transfection experiments, showing exponential decay over time, as shown in FIG. 4A.

TABLE 4

MOIs of lentiviral transductions before FACS sort.

| Construct | MOI | Construct | MOI |
|---|---|---|---|
| Ef1a | | PGK | |
| 3'UCOE | 0.25 | A2UCOE | 0.44 |
| Can 6-3 | 0.19 | Can 6-3 | 0.32 |
| A2UCOE | 0.26 | 3'UCOE | 0.33 |
| Can 6-1 | 0.29 | Can 6-1 | 0.39 |
| Can 6 | 0.30 | Can 6 | 0.25 |
| Ef1a | 0.48 | Can 6-2 | 0.62 |

TABLE 4-continued

MOIs of lentiviral transductions before FACS sort.

| Construct | MOI | Construct | MOI |
|---|---|---|---|
| Can 6-2 | 0.36 | PGK | 0.18 |
| CMV | | RSV | |
| Can 6-2 | 0.35 | Can 6 | 0.38 |
| A2UCOE | 0.28 | Can 6-1 | 0.12 |
| Can 6-1 | 0.23 | Can 6-3 | 0.48 |
| Can 6-3 | 0.57 | A2UCOE | 0.30 |
| 3'UCOE | 0.28 | 3'UCOE | 0.11 |
| Can 6 | 0.03 | RSV | 0.46 |
| CMV | 0.22 | Can 6-2 | 0.53 |

As all conditions were FACS-sorted at day 0 to 100% GFP positive, the percent GFP positive cells at day 26 (CMV/RSV) or day 27 (PGK % Ef1α) is a readout of the amount of silencing that has occurred. For FACS sorting, the GFP+ gate was drawn to encompass 1% of untransduced P19 samples, and then applied to all samples to quantify the percentage of GFP+ cells. In a representative example, the CMV promoter with no insulator shows 16.2% GFP+ cells, and the CMV promoter with the 6-2 candidate truncation shows 59.2 GFP+ cells at day 26; the RSV promoter with no insulator shows 8.99% GFP+ cells, and the RSV promoter with candidate 6 shows 79.6% GFP+ cells at day 26; the EF1a promoter with no insulator shows 17.3% GFP+ cells, and the EF1a promoter with the 6-3 candidate truncation shows 69% GFP+ cells at day 27; and the PGK promoter shows 5.32% GFP+ cells, and the PGK promoter with the 6-3 candidate truncation shows 47.8% GFP+ cells at day 27 (data not shown). For the representative examples described, the values represent one biological replicate for the promoter-only negative control and the candidate 6 variant (full-length or truncation) that maintained the highest percentage of GFP+ cells at day 26 (CMV/RSV) or dat 27 (PGK-EF1a). All of the described example populations show a consistently low SSC-A:SSC-A side-scatter value (approximately 25K or less). These data are summarized along with additional biological replicates in FIG. 4B. When linked to Ef1α, A2UCOE, 3'UCOE, and Candidate 6-3 have more than four times the GFP positive cells at day 26 compared to the negative control, with greater than 65% of cells GFP positive at day 27 for Candidate 6-3 compared to 15% in the negative control. The full-length Candidate 6 and 6-1 element maintain 2.7 and 3.6 times the expression of the negative control, respectively. Meanwhile, Candidate 6-2 is ineffective with 11% GFP+ cells as compared to 15% in the negative control.

For the CMV promoter, the negative control shows about 13% GFP+ cells at day 26. Unlike the other promoters tested, Candidate 6-2 is the best-performing population in this promoter, mediating 55% GFP+, a 4.4-fold improvement over the negative control and a 1.4-fold improvement over A2UCOE. A2UCOE, 6-1, and 6-3, all perform equivalently with 39% GFP+ cells at day 26, which is a 3-fold improvement over the negative control. Here, the full length A2UCOE is slightly more effective than 3'UCOE, and is exactly matched by truncations 6-1 and 6-3 at 39% GFP+.

For the PGK promoter, only about 5% of the negative control cells are still GFP+ at the day 27 timepoint. A2UCOE, 3'UCOE, and Candidate 6-3 perform similarly, maintaining more than 8 times the expressing cells than the control, with Candidate 6-3 mediating 49% GFP positive cells at the final timepoint. The full-length Candidate 6 and truncation 6-1 demonstrate 29% and 31% GFP+ at day 27, respectively, which corresponds to a 5-fold improvement over the negative control. Candidate 6-2 is substantially less effective than the other Candidate 6 sequences at 17% GFP+ cells at day 27.

Finally, Candidate 6 and associated truncations demonstrate the most improvement over the A2UCOE elements in the RSV promoter construct. At day 26, only 7% of cells in the negative control remain GFP+. A2UCOE and 3'UCOE exhibit substantial improvement over the control at 43% and 27% GFP+, respectively. Markedly, Candidate 6 maintains 76% GFP+ cells, with truncations 6-1 and 6-3 exhibiting 68% and 66% GFP+ cells, respectively. These three elements show at least a 9-fold improvement over the negative control and at least 1.5-fold over A2UCOE and 2.4-fold over the 1.2 kb 3'UCOE. Truncation 6-2, on the other hand, is ineffective when linked to the RSV promoter.

Taken together, the data demonstrate that Candidate 6 and the truncation constructs (with the exception of construct 6-2) showed substantial improvement over the negative control across all four tested promoters and performed on par (PGK/Ef1a) or at least 1.4 times better (CMV/RSV) than the positive controls A2UCOE and 3'UCOE. Candidate 6 and associated truncations were most efficacious in concert with the RSV promoter, outperforming the 2.2 kb A2UCOE by 1.5-fold, and the 1.2 kb 3'UCOE by more than two-fold in percent GFP+ cells after 26 days. While there is variability in the performance of the Candidate 6 truncations depending on the promoter, Candidate 6-3 exhibits the most consistent activity, outperforming the full-length Candidate 6 sequence in all promoters except RSV (where it is still highly effective). Thus, we suggest that the 767 bp Candidate 6-3 element would be an effective first choice for researchers looking to mediate anti-silencing activity, as this element maintains at least an equivalent level of percent GFP+ cells as A2UCOE/3'UCOE across all four promoters tested. Notably, truncation 6-2, which completely lacks the intergenic area between SURF1 and SURF2 genes, failed to outperform the negative control in 3 of the 4 promoters tested, suggesting that the functional core of the element is located within this intergenic region. The notable exception to this is the substantial protective effect of the 6-2 element with the CMV promoter, which indicates that the particular interplay of the 6-2 sequence and the components of the CMV promoter combine for a unique protective effect.

Example 5: Effective UCOEs Confer Resistance to DNA CpG Methylation and Histone-Deacylation An examination of whether Candidate 6 functioned on an epigenetic level to resist transgene silencing was next performed. It is well understood that transgene silencing is mediated by the loss of histone acetylation at the locus and addition of DNA methylation (Alhaji, S. Y. et al. (2018) *Biotechnol Genet Eng Rev*, 1-25 (4)). Two small molecule drugs have been widely used to probe this effect: (i) trichostatin A (TSA), which is a specific inhibitor of histone deacetylase, and (ii) 5-azacytidine (5-aza), a cytidine analog that inhibits methylation upon its incorporation into DNA. Both molecules have been individually used to reactivate expression of silenced transduced genes and to conclude that histone deacetylation and CpG methylation are integrally involved in transgene silencing (Chen, W. Y. et al. (1997) *Proc Natl Acad Sci USA*, 94, 5798-5803 (58); Pikaart, M. J. et al. (1998) *Genes Dev*, 12, 2852-2862 (59); Kuriyama, S. et al. (1998) *Gene Ther*, 5, 1299-1305 (60)).

Figure 5A:
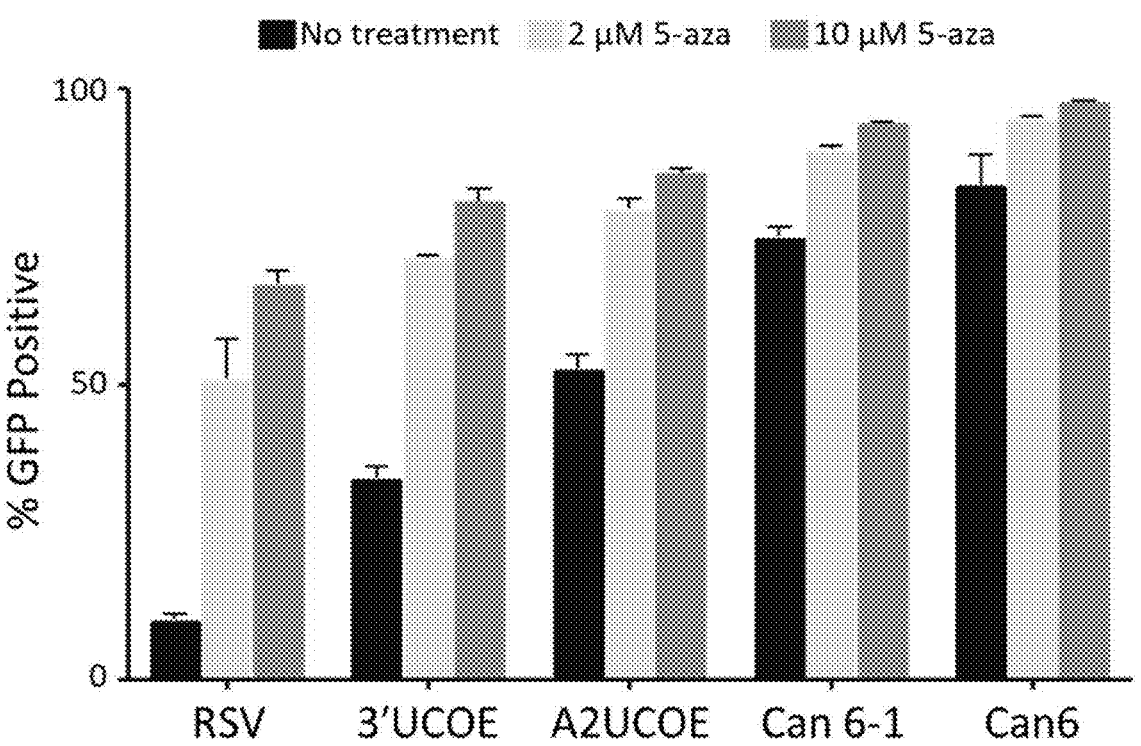
FIG. 5A shows that Candidate 6 (SRF-UCOE) resists DNA methylation and histone deacetylation according to aspects of this disclosure. GFP expression is rescued by treatment with DNA methylation inhibitor 5-aza-cytidine (5-aza) in day 18 UCOE-RSV cells from the lentiviral silencing experiment. Cells were replica plated at day 16, specified concentrations of 5-aza were introduced 24 hours later (with exception of control), and cells were passaged and assayed via flow cytometry 24 hours after chemical introduction for % GFP+ cells. Data is reported as mean±SD from three biological replicates.
Figure 5B:
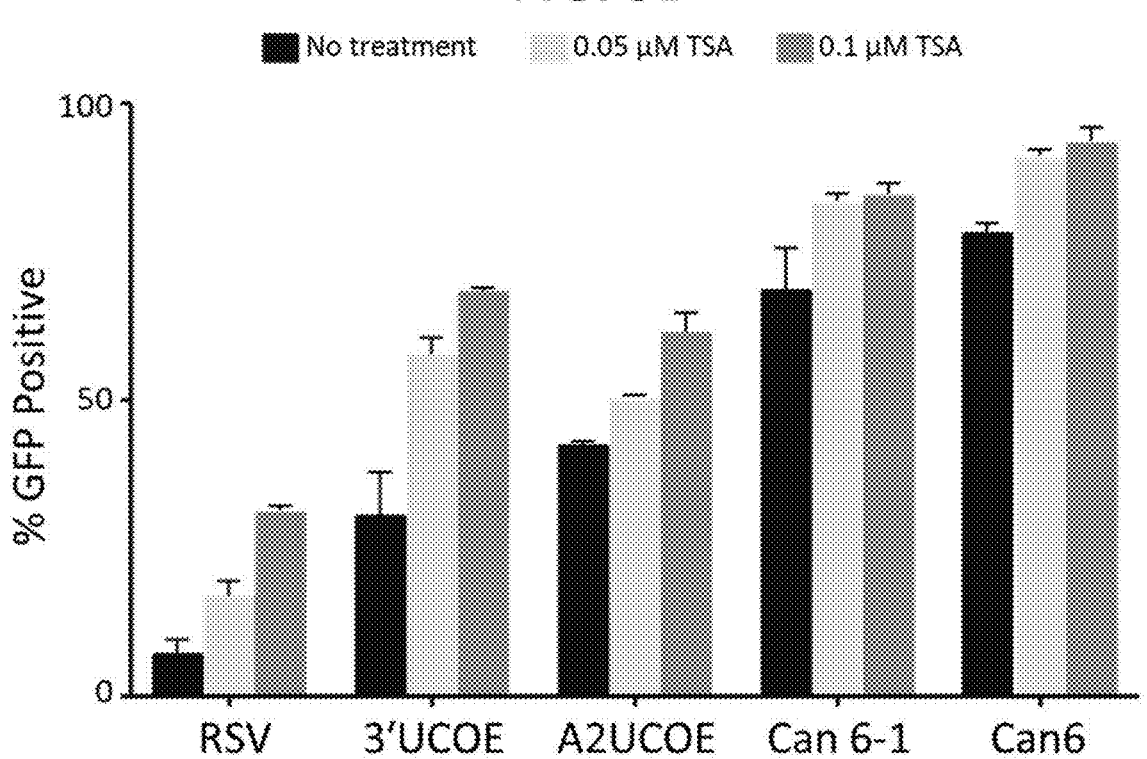
FIG. 5B shows that Candidate 6 (SRF-UCOE) resists DNA methylation and histone deacetylation according to aspects of this disclosure. GFP expression is rescued by treatment with HDAC inhibitor trichostatin A (TSA) in day 24 UCOE-RSV cells from the lentiviral silencing experiment. Cells were replica plated at day 22, specified concentrations of TSA were introduced 24 hours later (with exception of control), and cells were passaged and assayed via flow cytometry 24 hours after chemical introduction for % GFP+ cells. Data is reported as mean f SD from three biological replicates.
Figure 6A:
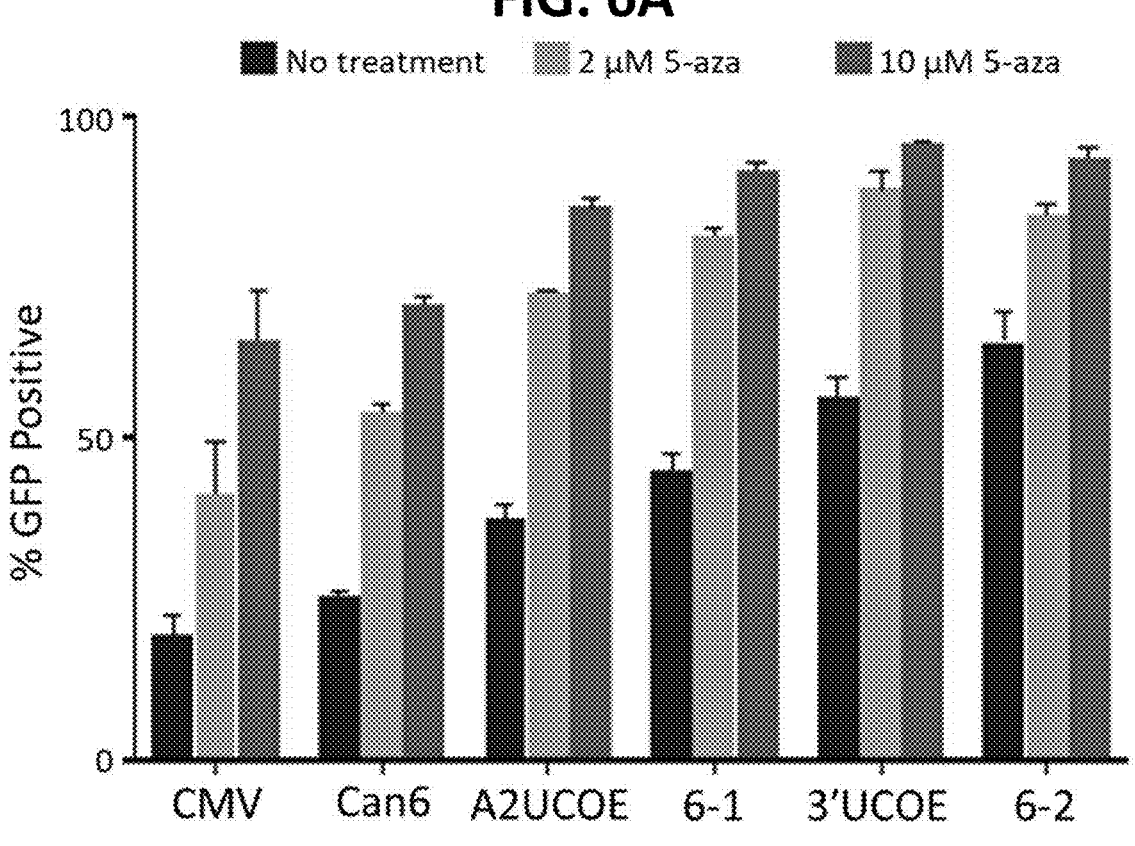
FIGS. 6A-6D shows that Candidate 6 (SRF-UCOE) resists DNA methylation and histone deacetylation according to aspects of this disclosure.
Figure 6B:
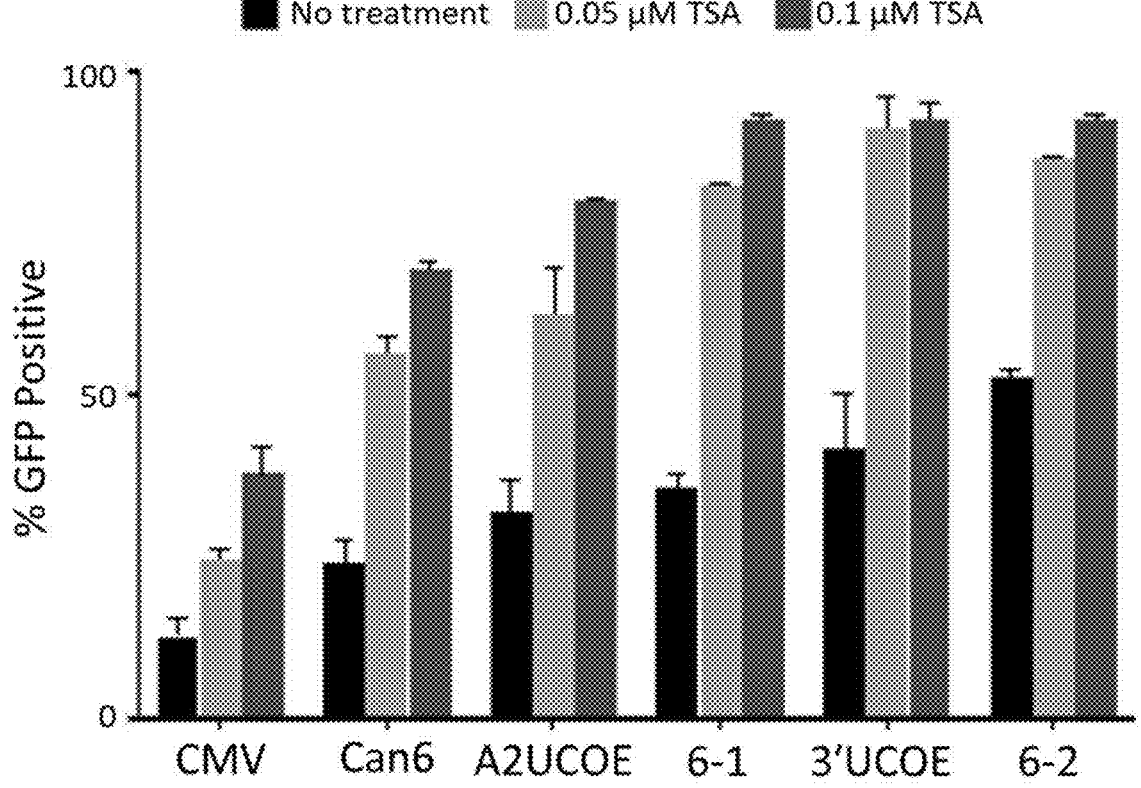
Figure 6C:
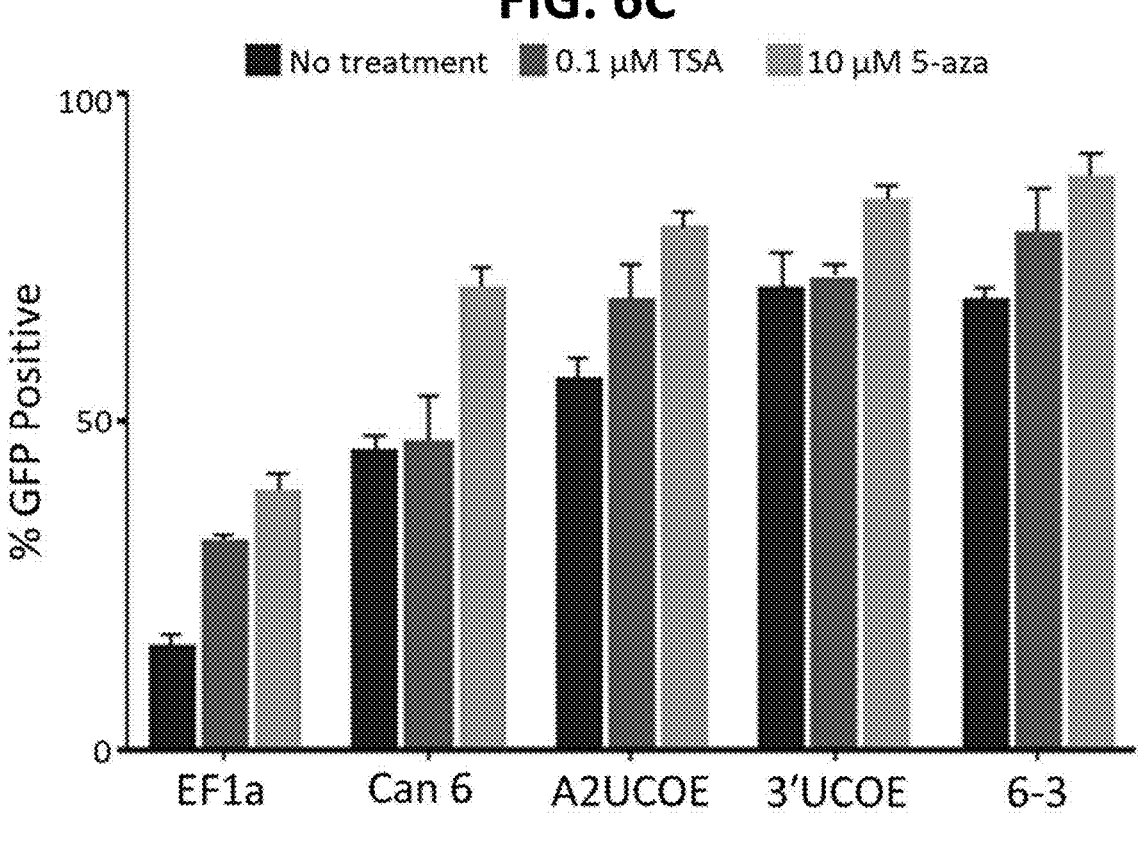
Figure 6D:
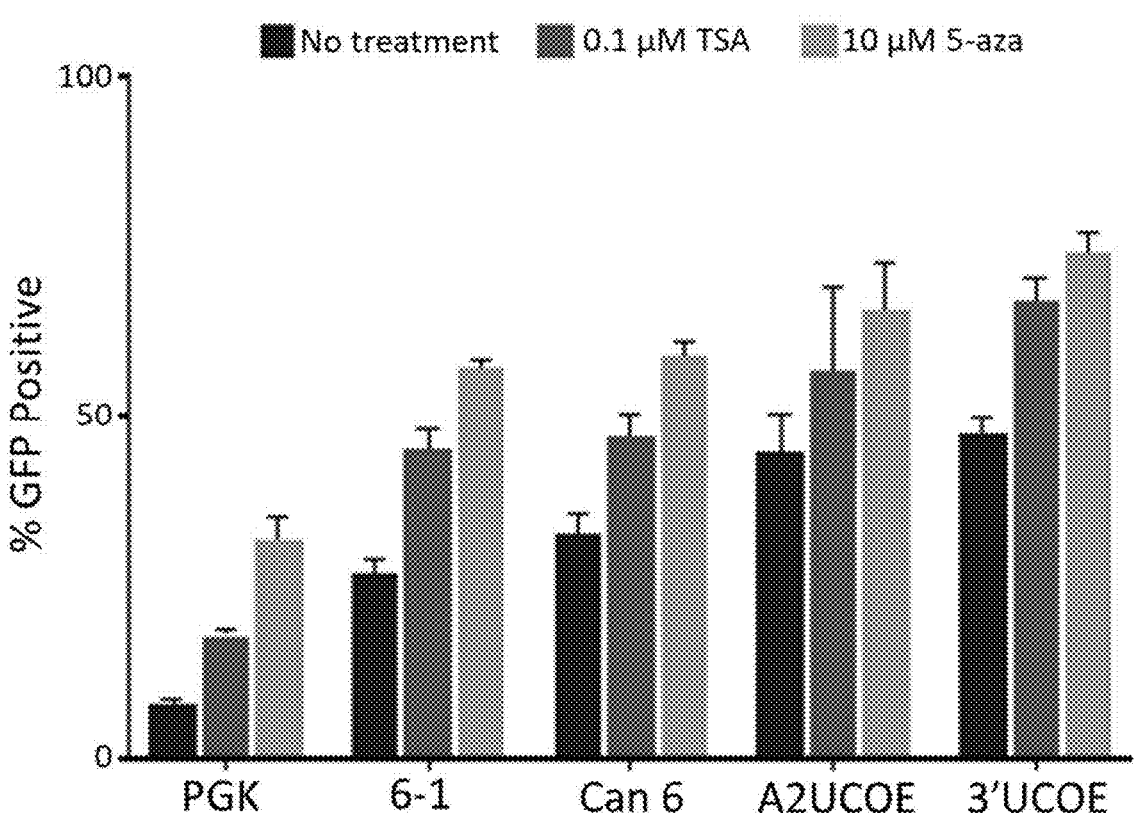

Transduced P19 cells undergoing the previously described silencing experiment were replica plated at late passages and treated a day later with a range of concentrations of 5-aza or TSA. Twenty-four hours later, cells were assayed by flow cytometry for reactivation of GFP expression. Data are shown in FIGS. 5A-5B (constructs with RSV promoter), FIGS. 6A-6B (constructs with CMV promoter), FIG. 6C (constructs with Ef1a promoter), and FIG. 6D (constructs with PGK promoter). All examined populations showed a dose-dependent increase in % GFP positive cells, with the highest dose of 5-aza rescuing 63% of the silenced cells in the RSV promoter-only construct, as shown in FIG. 5A. For every condition tested, increasing concentration of 5-aza increased the fraction of silenced cells that were reactivated, suggesting that even more cells may have been susceptible to 5-aza rescue if the toxicity of the chemical had not limited the concentration. This effect corroborates that the silencing seen in transduced cells is due to methylation of the DNA construct. Similarly, TSA-treated cells show a dose-dependent recovery of GFP expression, although to a smaller extent than 5-aza, with the highest dose of TSA rescuing only about 25% of silenced cells in the RSV promoter-only construct, as shown in FIG. 5B. These results further confirm the role of histone deacetylation in the silencing of transduced P19 cells. Even across the most effective UCOEs (Candidate 6 with RSV), more than 80% of silenced cells at day 18 and later can be rescued with the small molecule effectors. Taken together, the data indicate that silencing in our transduction experiments is due to epigenetic effects as opposed to a loss of the DNA construct, and that UCOEs (and particularly Candidate 6 and truncations) function by resisting DNA methylation or histone deacetylation at the integration locus.

The following embodiments are contemplated. As used below, any reference to a series of embodiments is to be understood as a reference to each of those embodiments disjunctively (e.g., "Embodiments 1-4" is to be understood as "Embodiments 1, 2, 3, or 4").

Embodiment 1 is a recombinant nucleic acid molecule comprising (a) a ubiquitous chromatic opening element (UCOE) polynucleotide comprising a nucleic acid sequence having at least 90% percent sequence identity over the length of the nucleic acid sequence set forth in SEQ ID NO:5; and (b) a heterologous promoter operably linked to the UCOE polynucleotide.

Embodiment 2 is the recombinant nucleic acid molecule of embodiment 1, comprising a nucleic acid sequence having at least 90% percent sequence identity to the nucleic acid sequence set forth in any of SEQ ID NOs: 1, 2, 3, or 4.

Embodiment 3 is the recombinant nucleic acid molecule of embodiment 1, comprising a nucleic acid sequence having at least 95% percent sequence identity to the nucleic acid sequence set forth in any of SEQ ID NOs: 1, 2, 3, 4, or 5.

Embodiment 4 is the recombinant nucleic acid molecule of any one of embodiments 1-3, further comprising a gene, wherein the heterologous promoter is operably linked to the gene.

Embodiment 5 is the recombinant nucleic acid molecule of any one of embodiments 1-4, wherein the heterologous promoter is a eukaryotic promoter or a viral promoter.

Embodiment 6 is the recombinant nucleic acid molecule of any one of embodiments 1-5, wherein the heterologous promoter is a mammalian promoter.

Embodiment 7 is the recombinant nucleic acid molecule of any one of embodiments 1-6, wherein the heterologous promoter is a tissue-specific promoter.

Embodiment 8 is a vector comprising the recombinant nucleic acid molecule of any one of embodiments 1-7.

Embodiment 9 is a host cell comprising the recombinant nucleic acid molecule of any one of embodiments 1-7 or the vector of embodiment 8.

Embodiment 10 is the host cell of embodiment 9, wherein the host cell is a eukaryotic cell.

Embodiment 11 is the host cell of embodiment 9, wherein the host cell is a bacterial cell.

Embodiment 12 is a composition comprising the recombinant nucleic acid molecule of any one of embodiments 1-7, the vector of embodiment 8, or the host cell of any one of embodiments 9-11.

Embodiment 13 is the composition of embodiment 12, wherein the composition comprises a pharmaceutically acceptable carrier.

Embodiment 14 is a method of treating a subject by gene therapy comprising administering to a subject in need of gene therapy an effective dose of the composition of embodiment 13.

Embodiment 15 is a method of producing a desired gene product comprising: (a) introducing the recombinant nucleic acid molecule of any one of embodiments 4-7 or the vector of embodiment 8 comprising the gene into a cell line or bacterial strain; and (b) culturing said cell line or bacterial strain to produce the gene product encoded by the gene.

Embodiment 16 is a method of increasing the expression of an endogenous gene in the genome of a cell comprising: (a) introducing the recombinant nucleic acid molecule of any one of embodiments 1-7 into the genome of a cell in a position operably associated with the endogenous gene; and (b) culturing said cell.

Embodiment 17 is a transgenic non-human animal containing cells that contain the recombinant nucleic acid molecule of any one of embodiment 1-7 or the vector of embodiment 8.

Embodiment 18 is a recombinant nucleic acid molecule comprising: (a) a ubiquitous chromatic opening element (UCOE) polynucleotide comprising the nucleic acid sequence of positions 479-780 of SEQ ID NO:1 up to the full length of SEQ ID NO:1; and (b) a heterologous promoter operably linked to the UCOE polynucleotide.

Embodiment 19 is a recombinant nucleic acid molecule comprising: (a) a ubiquitous chromatic opening element (UCOE) polynucleotide comprising a nucleic acid sequence having at least 90% percent sequence identity over the length of positions 479-780 of SEQ ID NO:1 up to at least 90% percent sequence identity of the full length of SEQ ID NO:1; and (b) a heterologous promoter operably linked to the UCOE polynucleotide.

Embodiment 20 is the recombinant nucleic acid molecule of embodiment 18 or 19, wherein the UCOE polynucleotide has 90% sequence identity to SEQ ID NOs: 1, 2, 3, or 4.

Embodiment 21 is the recombinant nucleic acid molecule of embodiment 18 or 19, wherein the UCOE polynucleotide has 95% sequence identity to SEQ ID NOs: 1, 2, 3, or 4.

Embodiment 22 is the recombinant nucleic acid molecule of any one of embodiments 18-21, further comprising a gene, wherein the heterologous promoter is operably linked to the gene.

Embodiment 23 is the recombinant nucleic acid molecule of any one of embodiments 18-22, wherein the heterologous promoter is a eukaryotic promoter or a viral promoter.

Embodiment 24 is the recombinant nucleic acid molecule of any one of embodiments 18-23, wherein the heterologous promoter is a mammalian promoter.

Embodiment 25 is the recombinant nucleic acid molecule of any one of embodiments 18-24, wherein the heterologous promoter is a tissue-specific promoter.

Embodiment 26 is a vector comprising the recombinant nucleic acid molecule of any one of embodiments 18-25.

Embodiment 27 is a host cell comprising the recombinant nucleic acid molecule of any one of embodiments 18-25 or the vector of embodiment 26.

Embodiment 28 is the host cell of embodiment 27, wherein the host cell is a eukaryotic cell.

Embodiment 29 is the host cell of embodiment 27, wherein the host cell is a bacterial cell.

Embodiment 30 is a composition comprising the recombinant nucleic acid molecule of any one of embodiments 18-25, the vector of embodiment 26, or the host cell of any one of embodiments 27-29.

Embodiment 31 is the composition of embodiment 30, wherein the composition comprises a pharmaceutically acceptable carrier.

Embodiment 32 is a method of treating a subject by gene therapy comprising administering to a subject in need of gene therapy an effective dose of the composition of embodiment 31.

Embodiment 33 is a method of producing a desired gene product comprising: (a) introducing the recombinant nucleic acid molecule of any one of embodiments 18-25 or the vector of embodiment 26 comprising the gene into a cell line or bacterial strain; and (b) culturing said cell line or bacterial strain to produce the gene product encoded by the gene.

Embodiment 34 is a method of increasing the expression of an endogenous gene in the genome of a cell comprising: (a) introducing the recombinant nucleic acid molecule of any one of embodiments 18-25 into the genome of a cell in a position operably associated with the endogenous gene; and (b) culturing said cell.

Embodiment 35 is a transgenic non-human animal containing cells that contain the recombinant nucleic acid molecule of any one of embodiment 18-25 or the vector of embodiment 26.

References cited in this disclosure:
1. Jostock, T. and Knopf, H. P. (2012) Mammalian stable expression of biotherapeutics. *Methods Mol Biol,* 899, 227-238.
2. Yang, Y., Mariati, Chusainow, J. and Yap, M. G. (2010) DNA methylation contributes to loss in productivity of monoclonal antibody-producing CHO cell lines. *J Biotechnol,* 147, 180-185.
3. Oleg E. Tolmachov, T.S.a.T.T. (2013) In Molina, F. M. (ed.), *Gene Therapy.* IntechOpen.
4. Alhaji, S. Y., Ngai, S. C. and Abdullah, S. (2018) Silencing of transgene expression in mammalian cells by DNA methylation and histone modifications in gene therapy perspective. *Biotechnol Genet Eng Rev,* 1-25.
5. Ellis, J. (2005) Silencing and variegation of gammaretrovirus and lentivirus vectors. *Human Gene Therapy,* 16, 1241-1246.
6. Antoniou, M., Harland, L., Mustoe, T., Williams, S., Holdstock, J., Yague, E., Mulcahy, T., Griffiths, M., Edwards, S., Ioannou, P. A. et al. (2003) Transgenes encompassing dual-promoter CpG islands from the human TBP and HNRPA2B1 loci are resistant to heterochromatin-mediated silencing. *Genomics,* 82, 269-279.
7. Zhang, F., Frost, A. R., Blundell, M. P., Bales, O., Antoniou, M. N. and Thrasher, A. J. (2010) A ubiquitous chromatin opening element (UCOE) confers resistance to DNA methylation-mediated silencing of lentiviral vectors. *Mol Ther,* 18, 1640-1649.
8. Dighe, N., Khoury, M., Mattar, C., Chong, M., Choolani, M., Chen, J., Antoniou, M. N. and Chan, J. K. (2014) Long-term reproducible expression in human fetal liver hematopoietic stem cells with a UCOE-based lentiviral vector. *PLoS One,* 9, e104805.

9. Muller-Kuller, U., Ackermann, M., Kolodziej, S., Brendel, C., Fritsch, J., Lachmann, N., Kunkel, H., Lausen, J., Schambach, A., Moritz, T. et al. (2015) A minimal ubiquitous chromatin opening element (UCOE) effectively prevents silencing of juxtaposed heterologous promoters by epigenetic remodeling in multipotent and pluripotent stem cells. *Nucleic Acids Res,* 43, 1577-1592.

10. Brendel, C., Muller-Kuller, U., Schultze-Strasser, S., Stein, S., Chen-Wichmann, L., Krattenmacher, A., Kunkel, H., Dillmann, A., Antoniou, M. N. and Grez, M. (2012) Physiological regulation of transgene expression by a lentiviral vector containing the A2UCOE linked to a myeloid promoter. *Gene Ther,* 19, 1018-1029.

11. Haenseler, W., Kuzmenko, E., Smalls-Mantey, A., Browne, C., Seger, R., James, W., . . . Siler, U. (2018) Lentiviral gene therapy vector with UCOE stably restores function in iPSC-derived neutrophils of a CDG patient. *Matters,* DOI: 10.19185/matters.201805000005.

12. Saunders, F., Sweeney, B., Antoniou, M. N., Stephens, P. and Cain, K. (2015) Chromatin function modifying elements in an industrial antibody production platform—comparison of UCOE, MAR, STAR and cHS4 elements. *PLoS One,* 10, e0120096.

13. Benton, T., Chen, T., McEntee, M., Fox, B., King, D., Crombie, R., Thomas, T. C. and Bebbington, C. (2002) The use of UCOE vectors in combination with a pre-adapted serum free, suspension cell line allows for rapid production of large quantities of protein. *Cytotechnology,* 38, 43-46.

14. Williams, S., Mustoe, T., Mulcahy, T., Griffiths, M., Simpson, D., Antoniou, M., Irvine, A., Mountain, A. and Crombie, R. (2005) CpG-island fragments from the HNRPA2B1/CBX3 genomic locus reduce silencing and enhance transgene expression from the hCMV promoter/enhancer in mammalian cells. *BMC Biotechnol,* 5, 17.

15. Ernst, J., Kheradpour, P., Mikkelsen, T. S., Shoresh, N., Ward, L. D., Epstein, C. B., Zhang, X., Wang, L., Issner, R., Coyne, M. et al. (2011) Mapping and analysis of chromatin state dynamics in nine human cell types. *Nature,* 473, 43-49.

16. Hsu, F., Kent, W. J., Clawson, H., Kuhn, R. M., Diekhans, M. and Haussler, D. (2006) The UCSC Known Genes. *Bioinformatics,* 22, 1036-1046.

17. Consortium, E. P. (2012) An integrated encyclopedia of DNA elements in the human genome. *Nature,* 489, 57-74.

18. Wang, J., Zhuang, J., Iyer, S., Lin, X. Y., Greven, M. C., Kim, B. H., Moore, J., Pierce, B. G., Dong, X., Virgil, D. et al. (2013) Factorbook.org: a Wiki-based database for transcription factor-binding data generated by the ENCODE consortium. *Nucleic Acids Res,* 41, D171-176.

19. She, X., Rohl, C. A., Castle, J. C., Kulkarni, A. V., Johnson, J. M. and Chen, R. (2009) Definition, conservation and epigenetics of housekeeping and tissue-enriched genes. *BMC Genomics,* 10, 269.

20. Kent, W. J., Sugnet, C. W., Furey, T. S., Roskin, K. M., Pringle, T. H., Zahler, A. M. and Haussler, D. (2002) The human genome browser at UCSC. *Genome Research,* 12, 996-1006.

21. Lindahl Allen, M. and Antoniou, M. (2007) Correlation of DNA methylation with histone modifications across the HNRPA2B1-CBX3 ubiquitously-acting chromatin open element (UCOE). *Epigenetics,* 2, 227-236.

22. Knight, S., Zhang, F., Mueller-Kuller, U., Bokhoven, M., Gupta, A., Broughton, T., Sha, S., Antoniou, M. N., Brendel, C., Grez, M. et al. (2012) Safer, silencing-resistant lentiviral vectors: optimization of the ubiquitous chromatin-opening element through elimination of aberrant splicing. *J Virol,* 86, 9088-9095.

23. Duhig, T. (1998) The human Surfeit locus. *Genomics,* 52, 72-78.

24. Khan, A., Fornes, O., Stigliani, A., Gheorghe, M., Castro-Mondragon, J. A., van der Lee, R, Bessy, A., Cheneby, J., Kulkarni, S. R., Tan, G. et al. (2018) JASPAR 2018: update of the open-access database of transcription factor binding profiles and its web framework. *Nucleic Acids Res,* 46, D1284.

25. Adamson, B., Norman, T. M., Jost, M., Cho, M. Y., Nunez, J. K., Chen, Y., Villalta, J. E., Gilbert, L. A., Horlbeck, M. A., Hein, M. Y. et al. (2016) A Multiplexed Single-Cell CRISPR Screening Platform Enables Systematic Dissection of the Unfolded Protein Response. *Cell,* 167, 1867-1882 el821.

26. Jost, M., Chen, Y., Gilbert, L. A., Horlbeck, M. A., Krenning, L., Menchon, G., Rai, A., Cho, M. Y., Stem, J. J., Prota, A. E. et al. (2017) Combined CRISPRi/a-Based Chemical Genetic Screens Reveal that Rigosertib Is a Microtubule-Destabilizing Agent. *Mol Cell,* 68, 210-223 e216.

27. Wu, C. (1989) Analysis of hypersensitive sites in chromatin. *Meth. Enzymol.,* 170, 269-289.

28. Crane-Robinson, C. et al. (1997) Chromosomal mapping of core histone acetylation by immunoselection. *Methods,* 12(1), 48-56.

29. Rein, T. et al. (1998) Identifying 5-methylcytosine and related modifications in DNA genomes, *Nucleic Acid Res.,* 26(10), 2255-2264.

30. Needleman and Wunsch (1970) A general method applicable to the search for similarities in the amino acid sequences of two proteins. *J. Mol. Biol.,* 48(3), 443-453.

31. Rice, P. et al. (2000) EMBOSS: The European Molecular Biology Open Software Suite, *Trends in Genetics,* 16(6), 276-277.

32. Altschul et al. (1997) Gapped BLAST and PSI-BLAST: a new generation of protein database search programs. *Nucleic Acids Res.,* 25(17), 3389-3402.

33. Hitt, M. M. et al. (1997) Human adenovirus vectors for gene transfer into mammalian cells. *Advances in Pharmacology,* 40, 137-206.

34. Anderson, W. F. (1998) Human gene therapy. *Nature,* 392 (6679 Suppl), 25-30.

35. Philip, R. et al. (1994) Efficient and sustained gene expression in primary T lymphocytes and primary and cultured tumor cells mediated by adeno-associated virus plasmid DNA complexed to cationic liposomes. *Mol. Cell. Biol.,* 14, 2411-2418.

36. Russell, D. W. et al. (1994) Adeno-associated virus vectors preferentially transduce cells in S phase. *PNAS USA,* 91(19), 8915-8919.

37. Flotte, T. R. et al. (1993) Stable in vivo expression of the cystic fibrosis transmembrane conductance regulator with an adeno-associated virus vector. *PNAS USA,* 90(22), 10613-10617.

38. Walsh, C. E. et al. (1992) Regulated high level expression of a human gamma-globin gene introduced into erythroid cells by an adeno-associated virus vector. *PNAS USA,* 89(15), 7257-7261.

39. Miller, J. L. et al. (1994) Recombinant adeno-associated virus (rAAV)-mediated expression of a human gamma-globin gene in human progenitor-derived erythroid cells. *PNAS USA,* 91(21), 10183-10187.

40. Emerson, S. G. (1996) Ex vivo expansion of hematopoietic precursors, progenitors, and stem cells: the next generation of cellular therapeutics. *Blood,* 87, 3082-3088.

41. Naso, M. F. et al. (2017) Adeno-associated virus (AAV) as a vector for gene therapy. *BioDrugs,* 31(4), 317-334.

42. Ehrhardt, A. et al. (2008) Episomal vectors for gene therapy. *Current Gene Therapy,* 8(3), 147-161.

43. Milone, M. C. and O'Doherty (2018) Clinical use of lentiviral vectors. *Leukemia,* 32, 1529-1541.

44. Kazuki, Y. and Oshimura, M. (2011) Human artificial chromosomes for gene delivery and the development of animal models. *Mol. Therapy,* 19(9), 1591-1601.

45. Rojo, P. et al. (2018) *CRSIPR-Cas systems: ushering in the new genome editing era. Bioengineered,* 9(1), 214-221.

46. Liu, C. et al., Delivery strategies of the CRISPR-Cas9 gene-editing system for therapeutic applications. *J. Control Release,* 266, 17-26.

47. Chowdhury, M. et al. (1991) Long-term improvement of hypercholesterolemia after ex vivo gene therapy in LDLR-deficient rabbits. *Science,* 254(5039), 1802-1805.

48. Wilson, J. M. et al. (1992) Ex vivo gene therapy of familial hypercholesterolemia. *Hum. Gene Ther.,* 3(2), 179-222.

49. Guttman, M. et al. (2010) Ab initio reconstruction of cell type-specific transcriptomes in mouse reveals the conserved multi-exonic structure of lincRNAs. *Nat Biotechnol,* 28, 503-510.

50. Hsu, F. et al. (2006) The UCSC Known Genes. *Bioinformatics,* 22, 1036-1046.

51. Consortium, E. P. (2012) An integrated encyclopedia of DNA elements in the human genome. *Nature,* 489, 57-74.

52. Wang, J. et al. (2013) Factorbook.org: a Wiki-based database for transcription factor-binding data generated by the ENCODE consortium. *Nucleic Acids Res,* 41, D171-176.

53. Bannister, A. J. and Kouzarides, T. (2011) Regulation of chromatin by histone modifications. *Cell Res,* 21, 381-395.

54. Weth, O. et al. (2014) CTCF induces histone variant incorporation, erases the H3K27me3 histone mark and opens chromatin. *Nucleic Acids Research,* 42, 11941-11951.

55. Zufferey, R. T. and Trono, D. (2001) Production of High-Titer Lentiviral Vectors. *Current Protocols in Human Genetics,* 26(1), 12.10.1-12.10.12: DOI: 10.1002/0471142905.hg1210s26.

56. Chen, S. et al. (2015) Genome-wide CRISPR screen in a mouse model of tumor growth and metastasis. *Cell,* 160, 1246-1260.

57. Gill, D. R. et al. (2001) Increased persistence of lung gene expression using plasmids containing the ubiquitin C or elongation factor 1 alpha promoter. *Gene Therapy,* 8, 1539-1546.

58. Chen, W. Y. et al. (1997) Reactivation of silenced, virally transduced genes by inhibitors of histone deacetylase. *Proc Natl Acad Sci USA,* 94, 5798-5803.

59. Pikaart, M. J. et al. (1998) Loss of transcriptional activity of a transgene is accompanied by DNA methylation and histone deacetylation and is prevented by insulators. *Genes Dev,* 12, 2852-2862.

60. Kuriyama, S. et al. (1998) Expression of a retrovirally transduced gene under control of an internal housekeeping gene promoter does not persist due to methylation and is restored partially by 5-azacytidine treatment. *Gene Ther,* 5, 1299-1305.

61. Uchiyama, T. et al. (2012) Foamy virus vector-mediated gene correction of a mouse model of Wiskott-Aldrich syndrome. *Mol Ther,* 20, 1270-1279.

62. Kunkiel, J. et al. (2017) The CpG-sites of the CBX3 ubiquitous chromatin opening element are critical structural determinants for the anti-silencing function. *Sci Rep,* 7, 7919.

64. Xiang, J. S., et al. (2019) Massively parallel RNA device engineering in mammalian cells with RNA-Seq. *Nature Comm,* 10(1), 4327.

It is understood that the examples and embodiments described herein are for illustrative purposes only and that various modifications or changes in light thereof will be suggested to persons skilled in the art and are to be included within the spirit and purview of this application and scope of the appended claims. The inventions have been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group. All publications, patents, and patent applications cited herein are hereby incorporated by reference in their entirety for all purposes.

What is claimed is:

1. A recombinant nucleic acid molecule for controlling expression of a gene of interest (GOI) in a target cell, the nucleic acid comprising (a) a ubiquitous chromatic opening element (UCOE) polynucleotide comprising a nucleic acid sequence having at least 90 percent sequence identity over the length of the nucleic acid sequence set forth in SEQ ID NO:5; and (b) a heterologous promoter;

wherein the UCOE and the promoter are each arranged in the recombinant nucleic acid to be operably linked to a GOI in a target cell so as to control expression of the GOI.

2. The recombinant nucleic acid molecule of claim 1, comprising a nucleic acid sequence having at least 90 percent sequence identity to the nucleic acid sequence set forth in any of SEQ ID NOs: 1, 2, 3, or 4.

3. The recombinant nucleic acid molecule of claim 1, comprising a nucleic acid sequence having at least 95 percent sequence identity to the nucleic acid sequence set forth in any of SEQ ID NOs: 1, 2, 3, 4, or 5.

4. The recombinant nucleic acid molecule of claim 1, further comprising said GOI.

5. The recombinant nucleic acid molecule of claim 1, wherein the heterologous promoter is a eukaryotic promoter or a viral promoter.

6. The recombinant nucleic acid molecule of claim 1, wherein the heterologous promoter is a mammalian promoter.

7. The recombinant nucleic acid molecule of claim 1, wherein the heterologous promoter is a tissue-specific promoter.

8. A vector comprising the recombinant nucleic acid molecule of claim 1.

9. A host cell comprising the recombinant nucleic acid molecule of claim 1.

10. The host cell of claim 9, wherein the host cell is a eukaryotic cell.

11. The host cell of claim 9, wherein the host cell is a bacterial cell.

12. A composition comprising the recombinant nucleic acid molecule of claim 1 formulated in a pharmaceutically acceptable carrier.

13. A recombinant nucleic acid molecule for controlling expression of a gene of interest (GOI) in a target cell, the nucleic acid comprising:

(a) a ubiquitous chromatic opening element (UCOE) polynucleotide comprising the nucleic acid sequence of positions 479-780 of SEQ ID NO: 1 up to the full length of SEQ ID NO: 1; and (b) a heterologous promoter;

wherein the UCOE and the promoter are each configured in the recombinant nucleic acid to be operably linked to a GOI in a target cell so as to control expression of the GOI.

14. A recombinant nucleic acid molecule for controlling expression of a gene of interest (GOI) in a target cell, the nucleic acid comprising:

(a) a ubiquitous chromatic opening element (UCOE) polynucleotide comprising a nucleic acid sequence having at least 90 percent sequence identity over the length of positions 479-780 of SEQ ID NO: 1 up to at least 90 percent sequence identity of the full length of SEQ ID NO: 1; and (b) a heterologous promoter, wherein the UCOE and the promoter are each configured in the recombinant nucleic acid to be operably linked to a GOI in a target cell so as to control expression of the GOI.

15. The recombinant nucleic acid molecule of claim 14, wherein the UCOE polynucleotide has 90% sequence identity to SEQ ID NOs: 1, 2, 3, or 4.

16. The recombinant nucleic acid molecule of claim 14, wherein the UCOE polynucleotide has 95% sequence identity to SEQ ID NOs: 1, 2, 3, or 4.

17. The recombinant nucleic acid molecule of claim 1, wherein the UCOE resists transgene silencing, resists DNA methylation, and/or resists histone deacetylation of the GOI.

18. A method of producing a product encoded by a gene of interest (GOI), comprising:

(a) introducing into a target cell the recombinant nucleic acid molecule of claim 4 comprising a UCOE and a heterologous promoter operably linked to said GOI; and (b) culturing the target cell to produce the product encoded by the GOI.

19. A method of increasing expression of an endogenous gene in the genome of a target cell, comprising:

(a) introducing the recombinant nucleic acid molecule of claim 1 into the genome of said cell such that the UCOE and the promoter of the recombinant nucleic acid are operably linked to said endogenous gene; and (b) culturing said target cell to produce a product encoded by said endogenous gene.

\* \* \* \* \*

SEQUENCE LISTING

```
<160> NUMBER OF SEQ ID NOS: 40

<210> SEQ ID NO 1
<211> LENGTH: 1002
<212> TYPE: DNA
<213> ORGANISM: Homo sapiens

<400> SEQUENCE: 1
gcacacgacc acaattccac tgaaagcatt ttaatacgga acttgtcact cccagggagc      60
ctccgctcag ccggcagttg gttcatttca atccccacga caacccttca aagtgcaggg     120
cagacagcag gtggctctgc ccaggcgcct ggatcacagc ccggcctgca gccctcacct     180
gggcgcgggg agaccctgag gacgctcctc caggcggcgc tggccggggc ctgcggacac     240
ggacgggcgg gctgagctcc gggacccctc cccgcgcccc gcaccccgca ccccgcaccc     300
cgcaccccgc accggcgct cacccgtccc agccccgccg cccgcagccc cagctgcaac     360
```

-continued

```
gcagccaccg ccgccatcgc acccggcccc gcgggcgctt ccgggacgca ggaggcatct      420
gcatccgggg cgccgctgag tcccgcccag agccccgccc ccggctccag gttctgcgag      480
cggcttccgc cgggctgctc cgcgggcgcg tcggccatga gcgagttgcc gggcgacgtg      540
cgggcgtttc tgcgggagca cccgagcctg cggctccaga cggacgcccg caaggttcgc      600
agcgcgggag gggaacggag tggcggagaa gggcgcagtt gggatgaggg gctgagggga      660
gggcagggga gaggagaggg cagggagag gggagagggg agagcaggag agaggggaag      720
gcagggagga gggcgcggcg ggatcagggg aggagaggga aggggcgcg gcaggagggg      780 gcaccaggga gcggagccct ggccctcctg acgtcctgcc cgcccacgcg tccgcaggtg      840
aggtgcatcc tgacaggtca cgagctgccc tgccgcctgc cggagctcca ggtctacacc      900
cgcggcaaaa agtaccagcg gctggtccgc gcctccccgg ccttcgacta tgcagagttc      960
gagccgcaca tcgtgcccag caccaagaac ccgtaggtgg tc                       1002
```

<210> SEQ ID NO 2
<211> LENGTH: 896
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
ttcaaagtgc agggcagaca gcaggtggct ctgcccaggc gcctggatca cagcccggcc       60
tgcagccctc acctgggcgc ggggagaccc tgaggacgct cctccaggcg gcgctggccg      120
gggcctgcgg acacggacgg gcgggctgag ctccgggacc cctccccgcg ccccgcaccc      180
cgcaccccgc accccgcacc ccgcaccccg cgctcacccg tcccagcccc gccgcccgca      240
gccccagctg caacgcagcc accgccgcca tcgcacccgg ccccgcgggc gcttccggga      300
cgcaggaggc atctgcatcc ggggcgccgc tgagtcccgc ccagagcccc gcccccggct      360
ccaggttctg cgagcggctt ccgccgggct gctccgcggg gcgtcggcc atgagcgagt      420 tgccgggcga cgtgcgggcg tttctgcggg agcacccgag cctgcggctc cagacggacg      480
cccgcaaggt tcgcagcgcg ggagggggac ggagtggcgg agaagggcgc agttgggatg      540
aggggctgag gggaggggcag gggagaggag agggcagggg agaggggaga ggggagagca      600
ggagagaggg gaaggcaggg gagagggcgc ggcgggatca ggggaggaga gggaaggggg      660
cgcggcagga gggggcacca gggagcggag ccctggccct cctgacgtcc tgcccgccca      720
cgcgtccgca ggtgaggtgc atcctgacag gtcacgagct gccctgccgc ctgccggagc      780
tccaggtcta cacccgcggc aaaaagtacc agcggctggt ccgcgcctcc cggccttcg      840 actatgcaga gttcgagccg cacatcgtgc ccagcaccaa gaacccgtag gtggtc         896
```

<210> SEQ ID NO 3
<211> LENGTH: 524
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
agcggcttcc gccgggctgc tccgcgggcg cgtcggccat gagcgagttg ccgggcgacg       60
tgcgggcgtt tctgcgggag cacccgagcc tgcggctcca gacggacgcc cgcaaggttc      120
```

-continued

```
gcagcgcggg aggggaacgg agtggcggag aagggcgcag ttgggatgag gggctgaggg        180
gagggcaggg gagaggagag ggcaggggag aggggagagg ggagagcagg agagagggga        240
aggcagggga gagggcgcgg cgggatcagg ggaggagagg gaaggggggcg cggcaggagg        300 gggcaccagg gagcggagcc ctggccctcc tgacgtcctg cccgcccacg cgtccgcagg        360
tgaggtgcat cctgacaggt cacgagctgc cctgccgcct gccggagctc caggtctaca        420
cccgcggcaa aaagtaccag cggctggtcc gcgcctcccc ggccttcgac tatgcagagt        480
tcgagccgca catcgtgccc agcaccaaga acccgtaggt ggtc                         524
```

<210> SEQ ID NO 4
<211> LENGTH: 761
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
gcacacgacc acaattccac tgaaagcatt ttaatacgga acttgtcact cccagggagc         60
ctccgctcag ccggcagttg gttcatttca atccccacga caaccccttca aagtgcaggg        120 cagacagcag gtggctctgc ccaggcgcct ggatcacagc ccggcctgca gccctcacct        180
gggcgcgggg agaccctgag gacgctcctc caggcggcgc tggccggggc ctgcggacac        240
ggacgggcgg gctgagctcc gggacccctc cccgcgcccc gcaccccgca ccccgcaccc        300
cgcaccccgc accggcgct caccgtccc agccccgccg cccgcagccc cagctgcaac          360
gcagccaccg ccgccatcgc accggcccc gcgggcgctt ccgggacgca ggaggcatct          420
gcatccgggg cgccgctgag tcccgcccag agccccgccc ccggctccag gttctgcgag        480
cggcttccgc cgggctgctc cgcgggcgcg tcggccatga gcgagttgcc gggcgacgtg        540
cgggcgtttc tgcgggagca cccgagcctg cggctccaga cggacgcccg caaggttcgc        600
agcgcgggag gggaacggag tggcggagaa gggcgcagtt gggatgaggg gctgagggga        660
gggcagggga gaggagggg caggggagag gggagagggg agagcaggag agaggggaag         720
gcaggggaga gggcgcggcg ggatcagggg aggagaggga a                            761
```

<210> SEQ ID NO 5
<211> LENGTH: 283
<212> TYPE: DNA
<213> ORGANISM: Homo sapiens

<400> SEQUENCE: 5

```
agcggcttcc gccgggctgc tccgcgggcg cgtcggccat gagcgagttg ccgggcgacg         60
tgcgggcgtt tctgcgggag cacccgagcc tgcggctcca gacggacgcc cgcaaggttc        120
gcagcgcggg aggggaacgg agtggcggag aagggcgcag ttgggatgag gggctgaggg        180
gagggcaggg gagaggagag ggcaggggag aggggagagg ggagagcagg agagagggga        240
aggcagggga gagggcgcgg cgggatcagg ggaggagagg gaa                          283
```

<210> SEQ ID NO 6
<211> LENGTH: 262
<212> TYPE: DNA
<213> ORGANISM: Rous sarcoma virus

<400> SEQUENCE: 6

```
aatgtagtct tatgcaatac tcttgtagtc ttgcaacatg gtaacgatga gttagcaaca         60
```

-continued

```
tgccttacaa ggagagaaaa agcaccgtgc atgccgattg gtggaagtaa ggtggtacga        120
tcgtgcctta ttaggaaggc aacagacggg tctgacatgg attggacgaa ccactgaatt        180
ccgcattgca gagatattgt atttaagtgc ctagctcgat acaataaacg ccatttgacc        240
attcaccaca ttggtgtgca cc                                                  262
```

```
<210> SEQ ID NO 7
<211> LENGTH: 589
<212> TYPE: DNA
<213> ORGANISM: Cytomegalovirus sp.

<400> SEQUENCE: 7
gttgacattg attattgact agttattaat agtaatcaat tacggggtca ttagttcata         60
gcccatatat ggagttccgc gttacataac ttacggtaaa tggcccgcct ggctgaccgc        120
ccaacgaccc ccgcccattg acgtcaataa tgacgtatgt tcccatagta acgccaatag        180
ggactttcca ttgacgtcaa tgggtggagt atttacggta aactgcccac ttggcagtac        240
atcaagtgta tcatatgcca agtacgcccc ctattgacgt caatgacggt aaatggcccg        300
cctggcatta tgcccagtac atgaccttat gggactttcc tacttggcag tacatctacg        360
tattagtcat cgctattacc atggtgatgc ggttttggca gtacatcaat gggcgtggat        420
agcggtttga ctcacgggga tttccaagtc tccaccccat tgacgtcaat gggagtttgt        480
tttggcacca aaatcaacgg gactttccaa aatgtcgtaa caactccgcc ccattgacgc        540
aaatgggcgg taggcgtgta cggtgggagg tctatataag cagagctct                    589
```

```
<210> SEQ ID NO 8
<211> LENGTH: 543
<212> TYPE: DNA
<213> ORGANISM: Unknown
<220> FEATURE:
<223> OTHER INFORMATION: Description of Unknown:
      Ef1-alpha promoter sequence

<400> SEQUENCE: 8
gatctgcgat cgctccggtg cccgtcagtg ggcagagcgc acatcgccca cagtccccga         60
gaagttgggg ggaggggtcg gcaattgaac cggtgcctag agaaggtggc gcggggtaaa        120
ctgggaaagt gatgtcgtgt actggctccg cctttttccc gagggtgggg gagaaccgta        180
tataagtgca gtagtcgccg tgaacgttct ttttcgcaac gggtttgccg ccagaacaca        240
gctgaagctt cgaggggctc gcatctctcc ttcacgcgcc cgccgcccta cctgaggccg        300
ccatccacgc cggttgagtc gcgttctgcc gcctcccgcc tgtggtgcct cctgaactgc        360
gtccgccgtc taggtaagtt taaagctcag gtcgagaccg ggcctttgtc cggcgctccc        420
ttggagccta cctagactca gccggctctc cacgctttgc ctgaccctgc ttgctcacct        480
ctacgtcttt gtttcgtttt ctgttctgcg ccgttacaga tccaagctgt gaccggcgcc        540
tac                                                                      543
```

```
<210> SEQ ID NO 9
<211> LENGTH: 515
<212> TYPE: DNA
<213> ORGANISM: Unknown
<220> FEATURE:
<223> OTHER INFORMATION: Description of Unknown:
      PGK promoter sequence

<400> SEQUENCE: 9
ccacggggtt ggggttgcgc cttttccaag gcagccctgg gtttgcgcag ggacgcggct         60
```

```
gctctgggcg tggttccggg aaacgcagcg gcgccgaccc tgggtctcgc acattcttca    120
cgtccgttcg cagcgtcacc cggatcttcg ccgctaccct tgtgggcccc ccggcgacgc    180
ttcctgctcc gcccctaagt cgggaaggtt ccttgcggtt cgcggcgtgc cggacgtgac    240
aaacggaagc cgcacgtctc actagtaccc tcgcagacgg acagcgccag ggagcaatgg    300
cagcgcgccg accgcgatgg gctgtggcca atagcggctg ctcagcgggc gcgccgagag    360
cagcggccgg gaaggggcgg tgcgggaggc ggggtgtggg gcggtagtgt gggccctgtt    420
cctgcccgcg cggtgttccg cattctgcaa gcctccggag cgcacgtcgg cagtcggctc    480
cctcgttgac cgaatcaccg acctctctcc ccagg                               515
```

```
<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
actaagagtc gacccatctt gacggcagcg ata                                  33
```

```
<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tagttctgct agccgctgag acgatctcgg aaa                                  33
```

```
<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
actaagagtc gaccgctgag acgatctcgg aaa                                  33
```

```
<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tagttctgct agcccatctt gacggcagcg ata                                  33
```

```
<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
```

```
actaagagtc gactcaccct cacggttagc tact                                  34

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tagttctgct agccaacgta caacgcagca ctc                                   33

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
actaagagtc gaccagaccg atctgattca ctgg                                  34

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
actaagagtc gacacttttc cacacactac ttccctc                               37

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tagttctgct agctctgtct ttccagcagc gtt                                   33

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
actaagagtc gacgcacacg accacaattc cac                                   33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
```

```
tagttctgct agcgaccacc tacgggttct tgg                                  33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
actaagagtc gacgaccacc tacgggttct tgg                                  33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tagttctgct agcgcacacg accacaattc cac                                  33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
actaagagtc gacaagcaca cggccctaga aat                                  33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tagttctgct agctggagag gaaaactacc ggc                                  33

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
actaagagtc gacgtcctgc ccacgtatct acc                                  33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tagttctgct agcctagcga ggagttagca cgg                                  33
```

```
<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
actaagagtc gacctagcga ggagttagca cgg                                  33

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tagttctgct agcgtcctgc ccacgtatct acc                                  33

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
actaagagtc gaccaagttc actgtgtgct gtgtatt                              37

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tagttctgct agcgtcttcg ttgccaacag gct                                  33

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
actaagagtc gacgaggggt tgggggtaaa attagt                               36

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tagttctgct agcaggttcc ttagtgggca aca                                  33
```

-continued

```
<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
actaagagtc gacagcaggg aaagcgagag aac                                 33

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tagttctgct agcaaaggcc ttcccactga tcg                                 33

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
actaagagtc gacaaaggcc ttcccactga tcg                                 33

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tagttctgct agcagcaggg aaagcgagag aac                                 33

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
actaagagtc gacttcaaag tgcagggcag aca                                 33

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
actaagagtc gacttctgcg agcggcttcc                                     30
```

-continued

```
<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tagttctgct agcttccctc tcctcccctg atc                                    33

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tagttctgct agccggtcgc ataggccgag                                        30
```